(12) United States Patent
Cirpus et al.

(10) Patent No.: US 8,049,064 B2
(45) Date of Patent: Nov. 1, 2011

US008049064B2

(54) METHOD FOR PRODUCING POLYUNSATURATED $C_{20}$- AND $C_{22}$-FATTY ACIDS WITH AT LEAST FOUR DOUBLE BONDS IN TRANSGENIC PLANTS

(75) Inventors: Petra Cirpus, Mannheim (DE); Jörg Bauer, Ludwigshafen (DE)

(73) Assignee: BASF Plant Science GmbH (DE)

( * ) Notice: Subject to any disclaimer, the term of this patent is extended or adjusted under 35 U.S.C. 154(b) by 959 days.

(21) Appl. No.: 11/886,857

(22) PCT Filed: Mar. 21, 2006

(86) PCT No.: PCT/EP2006/060913
§ 371 (c)(1),
(2), (4) Date: Sep. 21, 2007

(87) PCT Pub. No.: WO2006/100241
PCT Pub. Date: Sep. 28, 2006

(65) Prior Publication Data
US 2009/0158462 A1    Jun. 18, 2009

(30) Foreign Application Priority Data
Mar. 22, 2005  (DE) .......................... 10 2005 013 779

(51) Int. Cl.
*A01H 5/00* (2006.01)
*C12N 15/82* (2006.01)
*C07H 21/04* (2006.01)

(52) U.S. Cl. .... 800/281; 800/298; 536/23.2; 435/320.1; 435/419

(58) Field of Classification Search .................. None
See application file for complete search history.

(56) References Cited

U.S. PATENT DOCUMENTS

| | | | |
|---|---|---|---|
| 5,614,393 A | 3/1997 | Thomas et al. | |
| 6,075,183 A * | 6/2000 | Knutzon et al. | ............ 800/281 |
| 7,179,647 B2 | 2/2007 | Lerchl et al. | |
| 2004/0111763 A1 | 6/2004 | Heinz et al. | |

FOREIGN PATENT DOCUMENTS

| | | |
|---|---|---|
| CA | 2180154 | 7/1995 |
| CA | 2455163 A1 | 2/2003 |
| CA | 2533613 A1 | 2/2005 |
| EP | 0550162 A1 | 7/1993 |
| EP | 0616644 B1 | 9/1994 |
| EP | 0794250 A1 | 9/1997 |
| WO | WO-91/13972 A1 | 9/1991 |
| WO | WO-93/06712 A1 | 4/1993 |
| WO | WO-93/11245 A1 | 6/1993 |
| WO | WO-94/11516 A1 | 5/1994 |
| WO | WO-94/18337 A1 | 8/1994 |
| WO | WO-95/18222 A1 | 7/1995 |
| WO | WO-96/21022 A2 | 7/1996 |
| WO | WO-97/21340 A1 | 6/1997 |
| WO | WO-97/30582 A1 | 8/1997 |
| WO | WO-98/46763 A1 | 10/1998 |
| WO | WO-98/46764 A1 | 10/1998 |
| WO | WO-98/46765 A1 | 10/1998 |
| WO | WO-98/46776 A2 | 10/1998 |
| WO | WO-99/27111 A1 | 6/1999 |
| WO | WO-99/64616 A2 | 12/1999 |
| WO | WO-00/21557 A1 | 4/2000 |
| WO | WO-01/59128 A2 | 8/2001 |
| WO | WO-02/08401 A2 | 1/2002 |
| WO | WO-02/26946 A2 | 4/2002 |
| WO | WO-02/44320 A2 | 6/2002 |
| WO | WO-02/077213 A2 | 10/2002 |
| WO | WO-03/012092 A1 | 2/2003 |
| WO | WO-03/064638 A2 | 8/2003 |
| WO | WO-03/093482 A2 | 11/2003 |
| WO | WO-2005/007845 A2 | 1/2005 |
| WO | WO-2005/012316 A2 | 2/2005 |

OTHER PUBLICATIONS

Drexler et al, J. Plant Physiol 160: 779-802. 2003.*
Parker-Barnes et al, PNAS, USA 97(15): 8284-8289, Jul. 18, 2000.*
Beaudoin et al, PNAS, USA 97(12): 6421-6426, Jun. 6, 2000.*
Broun et al, Science 282: 1315-1317, Nov. 13, 1998.*
Van de Loo et al, PNAS USA 92: 6743-6747, Jul. 1995.*
Doerks, TIG 14(6) 248-250, Jun. 1998.*
Brenner, S.E., TIG 15(4): 132-133, Apr. 1999.*
Bork et al TIG 12(10): 425-427, Oct. 1996.*
Voelker, Ann Rev Plant Physiol and Plant Mol Biol 52: 335-361, 2001.*
Sequence search results 1-9, for SEQ ID No. 25, dated Aug. 17, 2010.*
Poulos, A., "Very long chain fatty acids in higher animals—A review", Lipids, 1995, vol. 30, No. 1, pp. 1-14.
Horrocks, L. A., et al., "Health benefits of docosahexaenoic acid (DHA)", Pharmacolofical Research, 1999, vol. 40, No. 3, pp. 211-225.
Stukey, J. E., et al., "The OLE1 gene of *Saccharomyces cerevisiae* encodes the Δ9 fatty acid desaturase and can be functionally replaced by the rat stearoyl-CoA desaturase gene", The Journal of Biological Chemistry, 1990, vol. 265, No. 33, pp. 20144-20149.
Wada, H., et al., "Enhancement of chilling tolerance of a cyanobacterium by genetic manipulation of fatty acid desaturation", Nature, 1990, vol. 347, pp. 200-203.

(Continued)

*Primary Examiner* — Elizabeth McElwain
(74) *Attorney, Agent, or Firm* — Connolly Bove Lodge & Hutz LLP

(57) ABSTRACT

The present invention relates to a process for the production of polyunsaturated fatty acids in transgenic plants, by introducing, into the plant, the nucleic acids which code for polypeptides with Δ6-desaturase, Δ6-elongase, a Δ5-desaturase, Δ5-elongase, Δ4-desaturase, Δ12-desaturase and/or ω3-desaturase activity. These desaturases and elongases are advantageously derived from *Phytophthora sojae*. The invention furthermore relates to the nucleic acid sequence, nucleic acid constructs, vectors and organisms comprising the nucleic acid sequences according to the invention, vectors comprising the nucleic acid sequence and/or the nucleic acid constructs and to transgenic plants comprising the abovementioned nucleic acid sequence, nucleic acid constructs and/or vectors. A further part of the invention relates to fatty acid compositions produced by the process according to the invention and to their use.

30 Claims, 1 Drawing Sheet

OTHER PUBLICATIONS

Huang, Y-S., et al., "Cloning of Δ2- and Δ6-desaturases from *Mortierella alpina* and recombinant production of γ-linolenic acid in *Saccharomyces cerevisiae*", Lipids, 1999, vol. 34, No. 7, pp. 649-659.

McKeon T., et al., "[34] Stearoyl-acyl carrier protein desaturase from safflower seeds", in "Methods in Enzymology, vol. 71, Lipids, Part C", Lowenstein, J. M., ed., Academic Press, pp. 275-281.

Wang, X. M., et al., "Biosynthesis and regulation of linolenc acid in higher plants", Plant Physiol. Biochem., 1988, vol. 26, No. 6, pp. 777-792.

Millar, A. A., et al., "Very-long-chain fatty acid biosynthesis is controlled through the expression and specificity of the condensing enzyme", The Plant Journal, 1997, vol. 12, No. 1, pp. 121-131.

Millar, A. A., "*CUT1*, an Arabidopsis gene required for cuticular wax biosynthesis and pollen fertility, encodes a very-long-chain fatty acid condensing enzyme", The Plant Cell, 1999, vol. 11, pp. 825-838.

Tvrdik, P., et al., "Role of a new mammalian gene family in the biosynthesis of very long chain fatty acids and sphingolipids", The Journal of Cell Biology, 2000, vol. 149, No. 3, pp. 707-717.

Vazhappilly, R., et al., "Heterotrophic production potential of omega-3 polyunsaturated fatty acids by microalgae and algae-like microorganisms", Botanica Marina, 1998, vol. 41, pp. 553-558.

Totani, N., et al., "The filamentous fungus *Mortierella alpina*, high in arachidonic acid", Lipids, 1987, vol. 22, No. 12, pp. 1060-1062.

Akimoto, M., et al., "Carbon dioxide fixation and polyunsaturated fatty acid production by the red alga *Porphyridium cruentum*", Applied Biochemistry and Biotechnology, 1998, vol. 73, pp. 269-278.

Tocher, D. R., et al., "Recent advances in the biochemistry and molecular biology of fatty acyl desaturases", Prog. Lipid Res., 1998, vol. 37, No. 2/3, pp. 73-117.

Takeyama, H., et al., "Expression of the eicosapentaenoic acid synthesis gene cluster from *Shewanella* sp. in a transgenic marine cyanobacterium, *Synechococcus* sp.", Microbiology, 1997, vol. 143, pp. 2725-2731.

Zank, T. K., "Cloning and functional characterisation of an enzyme involved in the elongation of Δ6-polyunsaturated fatty acids from the moss *Physcomitrella patens*", The Plant Journal, 2002, vol. 31, No. 3, pp. 255-268.

Sakuradani, E., et al, "Δ6-Fatty acid desaturase from an arachidonic acid-producing *Mortierella* fungus—gene cloning and its heterologous expression in a fungus, *Aspergillus*", Gene, 1999, vol. 238, pp. 445-453.

Sprecher, H., "Metabolism of highly unsaturated *n*-3 and *n*-6 fatty acids", Biochimica et Biophysica Acta, 2000, vol. 1486, vol. 219-231.

Domergue, F., et al., "Cloning and functional characterization of *Phaeodactylum tricornutum* front-end desaturases involved in eicosapentaenoic acid biosynthesis", Eur. J. Biochem., 2002, vol. 269, pp. 4105-4113.

Calder, P. C., "Dietary modification of inflammation with lipids", Proceedings of the Nutrition Society, 2002, vol. 61, pp. 345-358.

"Delta-12 desaturase", UniProtKB/TrEMBL Database, Accession No. Q6UB74, Jul. 5, 2004.

Cleland, L. G., et al., "Fish oil and rheumatoid arthritis: Antiinflammatory and collateral health benefits", The Journal of Rheumatology, 2000, vol. 27, No. 10, pp. 2305-2307.

Ucciani, E., "Nouveau Dictionnaire des Huiles Végétales", Technique & Documentation—Lavoisier, 1995, pp. 577, 578, and 582.

Pereira, S.L., et al., "A Novel ωβ-fatty Acid Desaturase Involved in the Biosynthesis of Eicosapentaenoic Acid", Biochem. J., vol. 378, No. 2, (2004), pp. 665-671.

Shimokawa, H., "Beneficial Effects of Eicosapentaenoic Acid on Endothelial Vasodilator Functions in Animals and Humans", World Rev. Nutr. Diet, vol. 88, (2001), pp. 100-108.

Yu, R., et al., "Production of Eicosapentaenoic Acid by a Recombinant Marine Cyanobacterium, *Synechococcus* sp.", Lipids, vol. 35, No. 10, (2000), pp. 1061-1064.

\* cited by examiner

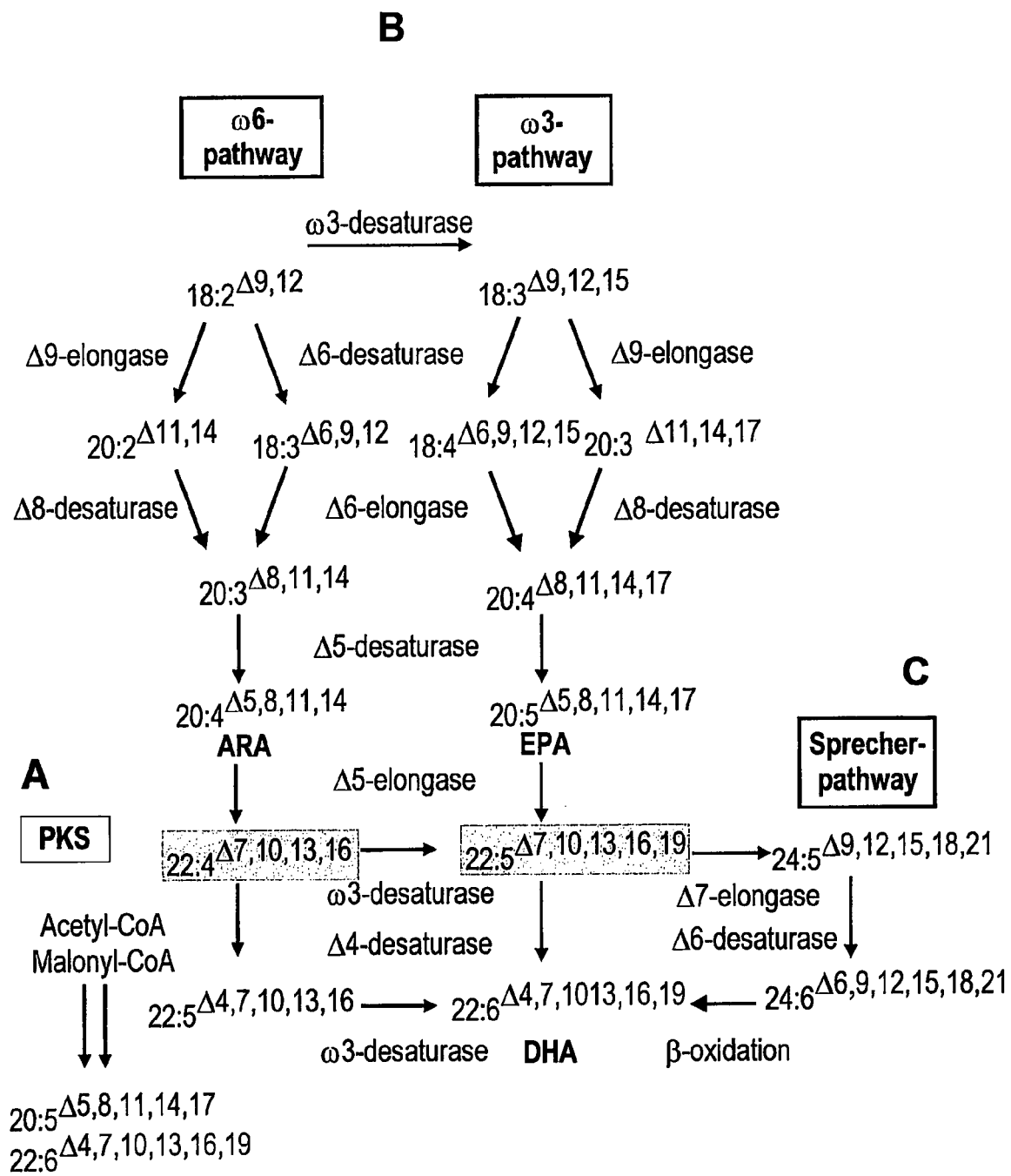

METHOD FOR PRODUCING POLYUNSATURATED $C_{20}$- AND $C_{22}$-FATTY ACIDS WITH AT LEAST FOUR DOUBLE BONDS IN TRANSGENIC PLANTS

RELATED APPLICATIONS

This application is a national stage application (under 35 U.S.C. 371) of PCT/EP2006/060913 filed Mar. 21, 2006, which claims benefit of German application 10 2005 013 779.2 filed Mar. 22, 2005.

Submission on Compact Disc

The contents of the following submission on compact discs are incorporated herein by reference in its entirety: two copies of the Sequence Listing (COPY 1 and COPY 2) and a computer readable form copy of the Sequence Listing (CRF COPY), all on compact disc, each containing: file name: Sequence List-13987-00069-US, date recorded: Sep. 21, 2007, size: 129 KB.

The present invention relates to a process for the production of polyunsaturated fatty acids in transgenic plants, by introducing, into the plant, the nucleic acids which code for polypeptides with Δ6-desaturase, Δ6-elongase, a Δ5-desaturase, Δ5-elongase, Δ4-desaturase, Δ12-desaturase and/or ω3-desaturase activity. These desaturases and elongases are advantageously derived from *Phytophthora sojae*.

The invention furthermore relates to the nucleic acid sequences, nucleic acid constructs, vectors and organisms comprising the nucleic acid sequences according to the invention, vectors comprising the nucleic acid sequences and/or the nucleic acid constructs and to transgenic plants comprise the abovementioned nucleic acid sequences, nucleic acid constructs and/or vectors.

A further part of the invention relates to fatty acid compositions produced by the process according to the invention and to their use.

Fatty acids and triacylglycerides have a multiplicity of applications in the food industry, in animal nutrition, in cosmetics and in the pharmacological sector. Depending on whether they are free saturated or unsaturated fatty acids or else triacylglycerides with an elevated content of saturated or unsaturated fatty acids, they are suitable for very different applications. Polyunsaturated fatty acids such as linoleic acid and linolenic acid are essential for mammals, since they cannot be produced by the latter. Polyunsaturated ω3-fatty acids and ω6-fatty acids are therefore an important constituent in animal and human nutrition.

Polyunsaturated long-chain ω3-fatty acids such as eicosapentaenoic acid (=EPA, $C20:5^{\Delta5,8,11,14,17}$) or docosahexaenoic acid (=DHA, $C22:6^{\Delta4,7,10,13,16,19}$) are important components in human nutrition owing to their various roles in health aspects, including the development of the child brain, the functionality of the eyes, the synthesis of hormones and other signal substances, and the prevention of cardiovascular disorders, cancer and diabetes (Poulos, A Lipids 30:1-14, 1995; Horrocks, L A and Yeo Y K Pharmacol Res 40:211-225, 1999). This is why there is a demand for the production of polyunsaturated long-chain fatty acids.

Owing to the present-day composition of human food, an addition of polyunsaturated ω3-fatty acids, which are preferentially found in fish oils, to the food is particularly important. Thus, for example, polyunsaturated fatty acids such as docosahexaenoic acid (=DHA, $C22:6^{\Delta4,7,10,13,16,19}$) or eicosapentaenoic acid (=EPA, $C20:5^{\Delta5,8,11,14,17}$) are added to infant formula to improve the nutritional value. The unsaturated fatty acid DHA is said to have a positive effect on the development and maintenance of brain functions.

Hereinbelow, polyunsaturated fatty acids are referred to as PUFA, PUFAs, LCPUFA or LCPUFAs (poly unsaturated fatty acids, PUFA, long chain poly unsaturated fatty acids, LCPUFA).

The various fatty acids and triglycerides are mainly obtained from microorganisms such as *Mortierella* and *Schizochytrium* or from oil-producing plants such as soybean, oilseed rape, algae such as *Crypthecodinium* or *Phaeodactylum* and others, where they are obtained, as a rule, in the form of their triacylglycerides (=triglycerides=triglycerols). However, they can also be obtained from animals, such as, for example, fish. The free fatty acids are advantageously prepared by hydrolysis. Very long-chain polyunsaturated fatty acids such as DHA, EPA, arachidonic acid (=ARA, $C20:4^{\Delta5,8,11,14}$), dihomo-γ-linolenic acid ($C20:3^{\Delta8,11,14}$) or docosapentaenoic acid (DPA, $C22:5^{\Delta7,10,13,16,19}$) are not synthesized in oil crop plants such as oilseed rape, soybean, sunflower or safflower. Conventional natural sources of these fatty acids are fish such as herring, salmon, sardine, redfish, eel, carp, trout, halibut, mackerel, zander or tuna, or algae.

Depending on the intended use, oils with saturated or unsaturated fatty acids are preferred. In human nutrition, for example, lipids with unsaturated fatty acids, specifically polyunsaturated fatty acids, are preferred. The polyunsaturated ω3-fatty acids are said to have a positive effect on the cholesterol level in the blood and thus on the possibility of preventing heart disease. The risk of heart disease, stroke or hypertension can be reduced markedly by adding these ω3-fatty acids to the food. Also, ω3-fatty acids have a positive effect on inflammatory, specifically on chronically inflammatory, processes in association with immunological diseases such as rheumatoid arthritis. They are therefore added to foodstuffs, specifically to dietetic foodstuffs, or are employed in medicaments. ω6-Fatty acids such as arachidonic acid tend to have a negative effect on these disorders in connection with these rheumatic diseases on account of our usual dietary intake.

ω3- and ω6-fatty acids are precursors of tissue hormones, known as eicosanoids, such as the prostaglandins, which are derived from dihomo-γ-linolenic acid, arachidonic acid and eicosapentaenoic acid, and of the thromboxanes and leukotrienes, which are derived from arachidonic acid and eicosapentaenoic acid. Eicosanoids (known as the $PG_2$ series) which are formed from ω6-fatty acids generally promote inflammatory reactions, while eicosanoids (known as the $PG_3$ series) from ω3-fatty acids have little or no proinflammatory effect.

Owing to the positive characteristics of the polyunsaturated fatty acids, there has been no lack of attempts in the past to make available genes which are involved in the synthesis of these fatty acids or triglycerides for the production of oils in various organisms with a modified content of unsaturated fatty acids. Thus, WO 91/13972 and its US equivalent describes a Δ9-desaturase. WO 93/11245 claims a Δ15-desaturase and WO 94/11516 a Δ12-desaturase. Further desaturases are described, for example, in EP-A-0 550 162, WO 94/18337, WO 97/30582, WO 97/21340, WO 95/18222, EP-A-0 794 250, Stukey et al., J. Biol. Chem., 265, 1990: 20144-20149, Wada et al., Nature 347, 1990: 200-203 or Huang et al., Lipids 34, 1999: 649-659. However, the biochemical characterization of the various desaturases has been insufficient to date since the enzymes, being membrane-bound proteins, present great difficulty in their isolation and characterization (McKeon et al., Methods in Enzymol. 71, 1981: 12141-12147, Wang et al., Plant Physiol. Biochem., 26, 1988: 777-792). As a rule, membrane-bound desaturases are characterized by being introduced into a suitable organism which is subsequently analyzed for enzyme activity by analyzing the starting materials and the products. Δ6-Desaturases are described in WO 93/06712, U.S. Pat. No. 5,614,393, U.S. Pat. No. 5,614,393, WO 96/21022, WO 00/21557 and WO 99/27111 and the application for the production in transgenic organisms is described in WO 98/46763, WO 98/46764 and WO 98/46765. In this context, the expression of various desaturases and the formation of polyunsaturated fatty acids is also described and claimed in WO 99/64616 or WO 98/46776. As regards the expression efficacy of desaturases and its effect on the formation of polyunsaturated fatty acids, it must be noted that the expression of a single desaturase as described to date has only resulted in low contents of unsaturated fatty acids/lipids such as, for example, γ-linolenic acid and stearidonic acid. Moreover, a mixture of ω3- and ω6-fatty acids was obtained, as a rule.

A large number of attempts have been made in the past of obtaining elongase genes. Millar and Kunst, 1997 (Plant Journal 12:121-131) and Millar et al. 1999, (Plant Cell 11:825-838) describe the characterization of elongases from plants for the synthesis of monounsaturated long-chain fatty acids (C22:1) and for the synthesis of very long-chain fatty acids for the production of wax in plants ($C_{28}$-$C_{32}$), respectively. Descriptions on the synthesis of arachidonic acid and EPA are found, for example, in WO0159128, WO0012720, WO02077213 and WO0208401. The synthesis of polyunsaturated C24-fatty acids is described for example in Tvrdik et al 2000, JCB 149:707-717 or WO0244320.

Especially suitable microorganisms for the production of PUFAs are microalgae such as *Phaeodactylum tricornutum*, *Porphiridium* species, *Thraustochytrium* species, *Schizochytrium* species or *Crypthecodinium* species, ciliates such as *Stylonychia* or *Colpidium*, fungae such as *Mortierella*, *Entomophthora* or *Mucor* and/or mosses such as *Physcomitrella*, *Ceratodon* and *Marchantia* (R. Vazhappilly & F. Chen (1998) Botanica Marina 41: 553-558; K. Totani & K. Oba (1987) Lipids 22: 1060-1062; M. Akimoto et al. (1998) Appl. Biochemistry and Biotechnology 73: 269-278). Strain selection has resulted in the development of a number of mutant strains of the microorganisms in question which produce a series of desirable compounds including PUFAs. However, the mutation and selection of strains with an improved production of a particular molecule such as the polyunsaturated fatty acids is a time-consuming and difficult process. This is why recombinant methods as described above are preferred whenever possible. However, only limited amounts of the desired polyunsaturated fatty acids such as DPA, EPA or ARA can be produced with the aid of the abovementioned microorganisms, and, depending on the microorganism used, these are generally obtained as fatty acid mixtures of, for example, EPA, DPA and ARA.

A variety of synthetic pathways is being discussed for the synthesis of arachidonic acid, eicosapentaenoic acid (EPA) and docosahexaenoic acid (DHA) (FIG. 1). Thus, EPA or DHA are produced in marine bacteria such as *Vibrio* sp. or *Shewanella* sp. via the polyketide pathway (Yu, R. et al. Lipids 35:1061-1064, 2000; Takeyama, H. et al. Microbiology 143:2725-2731, 1997).

An alternative strategy is the alternating activity of desaturases and elongases (Zank, T. K. et al. Plant Journal 31:255-268, 2002; Sakuradani, E. et al. Gene 238:445-453, 1999). A modification of the above-described pathway by Δ6-desaturase, Δ6-elongase, Δ5-desaturase, Δ5-elongase and Δ4-desaturase is the Sprecher synthetic pathway (Sprecher 2000, Biochim. Biophys. Acta 1486:219-231) in mammals. Instead of the Δ4-desaturation, a further elongation step is effected here to give $C_{24}$, followed by a further Δ6-desaturation and finally β-oxidation to give the $C_{22}$ chain length. Thus what is known as Sprecher synthetic pathway (see FIG. 1) is, however, not suitable for the production in plants and microorganisms since the regulatory mechanisms are not known.

As can be seen from FIG. 1, the production of longer-chain polyunsaturated fatty acids such as arachidonic acid, EPA or in particular DHA (C22:6 n−3) require, besides the desaturases, also elongases, which elongate unsaturated fatty acids with double bonds, for example in delta-9, delta-6 or delta-5 position by at least two carbon atoms. One distinguishes between two different types of elongase, depending on their function. The type I-elongases, which are widespread in the animal kingdom, only have poor substrate specificity, that is to say they elongate a series of different unsaturated fatty acids. Type II-elongases are distinguished by a much higher substrate specificity. They convert only few fatty acids with double bonds in specific positions.

WO 2005/012316 describes some of the abovementioned desaturases and elongases. Specifically, WO 2005/012316 discloses first type II-elongases which specifically elongate fatty acids with a double bond in the delta-5 position.

Depending on their desaturation pattern, the polyunsaturated fatty acids can be divided into two large classes, viz. ω6- or ω3-fatty acids, which differ with regard to their metabolic and functional activities (FIG. 1).

The starting material for the ω6-metabolic pathway is the fatty acid linoleic acid ($18:2^{\Delta9,12}$) while the ω3-pathway proceeds via linolenic acid ($18:3^{\Delta9,12,15}$). Linolenic acid is formed by the activity of an ω3-desaturase (Tocher et al. 1998, Prog. Lipid Res. 37, 73-117; Domergue et al. 2002, Eur. J. Biochem. 269, 4105-4113).

Mammals, and thus also humans, have no corresponding desaturase activity (Δ12- and ω3-desaturase) and must take up these fatty acids (essential fatty acids) via the food. Starting with these precursors, the physiologically important polyunsaturated fatty acids arachidonic acid (=ARA, $20:4^{\Delta5,8,11,14}$), an ω6-fatty acid and the two ω3-fatty acids eicosapentaenoic acid (=EPA, $20:5^{\Delta5,8,11,14,17}$) and docosahexaenoic acid (DHA, $22:6^{\Delta4,7,10,13,17,19}$) are then synthesized via the sequence of desaturase and elongase reactions. The application of ω3-fatty acids shows the therapeutic activity described above in the treatment of cardiovascular diseases (Shimikawa 2001, World Rev. Nutr. Diet. 88, 100-108), inflammations (Calder 2002, Proc. Nutr. Soc. 61, 345-358) and arthritis (Cleland and James 2000, J. Rheumatol. 27, 2305-2307).

Higher plants comprise polyunsaturated fatty acids such as linoleic acid (C18:2) and linolenic acid (C18:3). ARA, EPA and DHA are found not at all in the seed oil of higher plants, or only in miniscule amounts (E. Ucciani: Nouveau Dictionnaire des Huiles Végétales [New Dictionary of Vegetable Oils]. Technique & Documentation-Lavoisier, 1995. ISBN: 2-7430-0009-0). However, the production of LCPUFAs in higher plants, preferably in oil crops such as oilseed rape, linseed, sunflower and soybeans, would be advantageous since large amounts of high-quality LCPUFAs for the food industry, animal nutrition and pharmaceutical purposes might be obtained economically in this way. To this end, it is advantageous to introduce, into oil crops, genes which code for enzymes of the LCPUFA biosynthesis via recombinant methods and to express them therein. WO 2005/012316 describes such an approach. However, the disadvantage of the path described in WO 2005/012316 is that the yield of the desired fatty acids is still too low to be exploited industrially. In addition, not only the desired fatty acids such as ARA, EPA or DHA are generated, but undesired secondary reactions also give rise to fatty acids which further reduce the yield and contaminate the product formed.

An advantageous process for the production of polyunsaturated fatty acids should therefore combine in itself as many as possible of the following properties:
- high specificity of the desaturases and elongases used for the production of polyunsaturated fatty acids,
- high synthesis rate of the desaturases and elongases used,
- synthesis of, if possible, only one polyunsaturated fatty acids such as ARA, EPA or DHA,
- high yield of polyunsaturated fatty acids such as ARA, EPA or DHA or their mixtures,
- the lowest possible amount of undesired secondary products, if any,
- no production of unnatural fatty acids, i.e. fatty acids which do not occur naturally,
- synthesis of the polyunsaturated fatty acids advantageously only in the triglycerides.

In order to make possible a fortification of the food and of the feed with these polyunsaturated fatty acids, there is therefore a great demand for a simple, inexpensive process for the production of these polyunsaturated fatty acids, specifically in eukaryotic systems.

BRIEF DESCRIPTION OF THE DRAWINGS

FIG. 1 depicts various synthetic pathways for the biosynthesis of DHA (docosahexaenoic acid).

DETAILED DESCRIPTION

It was therefore an object to develop a simple, inexpensive process which has as many as possible of the abovementioned advantageous properties. This object was achieved by the process according to the invention for the production of polyunsaturated $C_{20}$- or $C_{22}$-fatty acids with at least four double bonds in transgenic plants with a content of at least 15% by weight based on the total triglyceride content of the transgenic plants, which comprises the following process steps:
   a) introducing, into the transgenic plant, a nucleic acid construct which comprises nucleic acid sequences which codes for a Δ6-desaturase, a Δ6-elongase and a Δ5-desaturase, or
   b) introducing, into the transgenic plant, a nucleic acid construct which comprises nucleic acid sequences which codes for a Δ6-desaturase, a Δ6-elongase, a Δ5-desaturase, a Δ12-desaturase and ω3-desaturase, or
   c) introducing, into the transgenic plant, a nucleic acid construct which comprises nucleic acid sequences which codes for a Δ6-desaturase, a Δ6-elongase, a Δ5-desaturase, a Δ5-elongase and Δ4-desaturase, or
   d) introducing, into the transgenic plant, a nucleic acid construct which comprises nucleic acid sequences which codes for a Δ6-desaturase, a Δ6-elongase, a Δ5-desaturase, a Δ5-elongase, Δ4-desaturase, a Δ12-desaturase and ω3-desaturase, and
   e) obtaining the oils or lipids from the plants.

The $C_{20}$- and $C_{22}$-polyunsaturated fatty acids produced in the process according to the invention advantageously comprise at least four, five or six double bonds. The fatty acids especially advantageously comprise five or six double bonds. Saturated fatty acids are advantageously converted to a minor degree, or not at all, by the nucleic acids used in the process. To a minor degree is to be understood as meaning that the saturated fatty acids are reacted with less than 5% of the activity, advantageously less than 3%, especially advantageously with less than 2%, very especially preferably with less than 1, 0.5, 0.25 or 0.125% of the activity in comparison with polyunsaturated fatty acids. These fatty acids which have been produced can be produced in the process as a single product or be present in a fatty acid mixture.

The nucleic acid sequences used in the process according to the invention are isolated nucleic acid sequences which code for polypeptides with Δ6-desaturase, Δ6-elongase, Δ5-desaturase, Δ5-elongase, Δ4-desaturase, Δ12-desaturase and/or ω3-desaturase activity.

Nucleic acid sequences which are advantageously used in the process according to the invention are those which code for polypeptides with Δ6-desaturase, Δ6-elongase, Δ5-desaturase, Δ5-elongase, Δ4-desaturase, Δ12-desaturase and/or ω3-desaturase activity, selected from the group consisting of:
SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23 or SEQ ID NO: 25.

The polyunsaturated $C_{20}$- or $C_{22}$-fatty acids with at least four double bonds which are produced in the process are especially advantageously the fatty acids arachidonic acid (=ARA), eicosapentaenoic acid (=EPA) or docosahexaenoic acid (=DHA). In an advantageous embodiment of the process, the polyunsaturated $C_{20}$- or $C_{22}$-fatty acids with at least four double bonds is arachidonic acid. In another advantageous embodiment, the polyunsaturated $C_{20}$- or $C_{22}$-fatty acids with at least four double bonds which are produced are eicosapentaenoic acid or docosahexaenoic acid or their mixtures. Mixtures of ARA, EPA and DHA can also be produced by the process according to the invention.

Advantageously, arachidonic acid or eicosapentaenoic acid with a content of at least 15, 16, 17, 18, 19 or 20% by weight, preferably 25, 30, 35 or 40% by weight, especially preferably 45, 50, 55 or 60% by weight, based on the total triglyceride content, are produced in the transgenic plant in the process according to the invention.

In another advantageous embodiment of the process, docosahexaenoic acid with a content of at least 4, 5 or 6% by weight, advantageously with a content of 7, 8, 9 or 10% by weight, based on the total triglyceride content, is produced in the transgenic plant.

It is especially advantageous that, in the process according to the invention, less than 0.5, 0.4, 0.3, 0.2 or 0.1% by weight, advantageously less than 0.09, 0.08, 0.07, 0.06 or 0.05% by weight, especially advantageously less than 0.04, 0.03, 0.02 or 0.01% by weight, based on the total fatty acid content of the triglycerides, of a polyunsaturated fatty acid selected from the group consisting of the $C22:4^{\Delta7,10,13,16}$-, $C22:5^{\Delta4,7,10,13,16}$- or $C22:5^{\Delta7,10,13,16,19}$-fatty acid should be present in the triglycerides.

The polyunsaturated fatty acids produced in the process are advantageously bound in triacylglycerides, but may also occur in the organisms as free fatty acids or else bound in the form of other fatty acid esters. In this context, they may be present as "pure products" or else advantageously in the form of mixtures of various fatty acids or mixtures of different glycerides.

The process according to the invention advantageously yields fatty acid esters with polyunsaturated $C_{20}$- and/or $C_{22}$-fatty acid molecules with at least four double bonds in the fatty acid ester, advantageously with at least five or six double bonds in the fatty acid ester. This leads to the synthesis of ω3-eicosatetraenoic acid (=ETA, $C20:4^{\Delta5,8,11,14}$), arachidonic acid (ARA, $C20:4^{\Delta5,8,11,14}$), eicosapentaenoic acid (EPA, $C20:5^{\Delta5,8,11,14,17}$), ω6-docosapentaenoic acid ($C22:5^{\Delta4,7,10,13,16}$), ω6-docosatetraenoic acid ($C22:4^{\Delta7,10,13,16}$), ω3-docosapentaenoic acid (=DPA, $C22:5^{\Delta7,10,13,16,19}$), docosahexaenoic acid (=DHA, C22:6$^{\Delta 4,7,10,13,16,19}$) or mixtures of these ARA, EPA and/or DHA are preferably produced. In an especially preferred embodiment of the process, ω6-fatty acids, advantageously arachidonic acid, are produced. In another especially preferred embodiment of the process, ω3-fatty acids such as EPA and/or DHA are produced.

The process according to the invention, as described above, especially advantageously yields polyunsaturated fatty acids selected from the group consisting of ω6-docosa-tetraenoic acid C22:4$^{\Delta 7,10,13,16}$, ω6-docosapentaenoic acid C22:5$^{\Delta 4,7,10,13,16}$ or ω3-docosapentaenoic acid C22:5$^{\Delta 7,10,13,16,19}$ in the triglycerides with less than 0.5% by weight based on the total fatty acid content of the triglycerides.

The fatty acid esters with polyunsaturated $C_{20}$- and/or $C_{22}$-fatty acid molecules can be isolated in the form of an oil or lipid, for example in the form of compounds such as sphingolipids, phosphoglycerides, lipids, glycolipids such as glycosphingolipids, phospholipids such as phosphatidylethanolamine, phosphatidylcholine, phosphatidyl-serine, phosphatidylglycerol, phosphatidylinositol or diphosphatidylglycerol, monoacyl-glycerides, diacylglycerides, triacylglycerides or other fatty acid esters such as the acetyl-coenzyme A esters which comprise the polyunsaturated fatty acids with at least four, five or six, preferably five or six double bonds, from the organisms which have been used for the preparation of the fatty acid esters; advantageously, they are isolated in the form of their diacylglycerides, triacylglycerides and/or in the form of phosphatidylcholine, especially preferably in the form of the triacylglycerides. In addition to these esters, the polyunsaturated fatty acids are also present in the organisms, advantageously the plants as free fatty acids or bound in other compounds. As a rule, the various abovementioned compounds (fatty acid esters and free fatty acids) are present in the organisms with an approximate distribution of 80 to 90% by weight of triglycerides, 2 to 5% by weight of diglycerides, 5 to 10% by weight of monoglycerides, 1 to 5% by weight of free fatty acids, 2 to 8% by weight of phospholipids, the total of the various compounds amounting to 100% by weight.

The process according to the invention yields the LCPUFAs, such as arachidonic acid and eicosapentaenoic acid produced in a content of at least 15% by weight, advantageously at least 16 or 17% by weight, preferably at least 18, 19 or 20% by weight, especially preferably at least 21, 22, 23, 24 or 25% by weight, most preferably at least 26, 27, 28, 29 or 30% by weight based on the total fatty acids in the transgenic organisms, advantageously in a transgenic plant. In this context, it is advantageous to convert $C_{18}$- and/or $C_{20}$-fatty acids which are present in the host organisms to at least 10%, preferably to at least 20%, especially preferably to at least 30%, most preferably to at least 40% to give the corresponding products such as ARA, EPA and/or DHA. The fatty acids are advantageously produced in bound form. These unsaturated fatty acids can, with the aid of the nucleic acids used in the process according to the invention, be positioned at the sn1, sn2 and/or sn3 position of the advantageously produced triglycerides. Since a plurality of reaction steps are performed by the starting compounds linoleic acid (C18:2) and linolenic acid (C18:3) in the process according to the invention, the end products of the process such as, for example, arachidonic acid (ARA), eicosapentaenoic acid (EPA) or docosapentaenoic acid (DHA) are not obtained as absolutely pure products; minor traces of the precursors are always present in the end product. If, for example, both linoleic acid and linolenic acid are present in the starting organism and the starting plant, the end products such as ARA, EPA or DHA are generally present as mixtures. The precursors linoleic acid and/or linolenic acid should advantageously not amount to more than 20% by weight, preferably not to more than 15% by weight, especially preferably not to more than 10% by weight, most preferably not to more than 5% by weight, based on the amount of the end product in question. Advantageously, only ARA, ARA and EPA, EPA and DHA or only DHA, bound or as free acids, are produced as end products in a transgenic plant owing to the process according to the invention. If the compounds ARA, EPA and DHA are produced simultaneously, they are advantageously produced in a ratio of at least 1:1:2 (EPA:ARA:DHA), advantageously of at least 1:1:3, preferably 1:1:4, especially preferably 1:1:5. If ARA and EPA are produced in the process, they are advantageously produced in a ratio of at least 5:1 to at least 1:5. If EPA and DHA are produced in the process, they are advantageously produced in a ratio of at least 5:1 to at least 1:5.

Fatty acid esters or fatty acid mixtures produced by the process according to the invention advantageously comprise 6 to 15% of palmitic acid, 1 to 6% of stearic acid, 7-85% of oleic acid, 0.5 to 8% of vaccenic acid, 0.1 to 1% of arachic acid, 7 to 25% of saturated fatty acids, 8 to 85% of monounsaturated fatty acids and 60 to 85% of polyunsaturated fatty acids, in each case based on 100% and on the total fatty acid content of the organisms. Advantageous polyunsaturated fatty acids which are present in the fatty acid esters or fatty acid mixtures are preferably at least 0.1, 0.2, 0.3, 0.4, 0.5, 0.6, 0.7, 0.8, 0.9 or 1% of arachidonic acid, based on the total fatty acid content. Moreover, the fatty acid esters or fatty acid mixtures which have been produced by the process of the invention advantageously comprise fatty acids selected from the group of the fatty acids erucic acid (13-docosaenoic acid), sterulic acid (9,10-methylene-octadec-9-enoic acid), malvalic acid (8,9-methyleneheptadec-8-enoic acid), chaulmoogric acid (cyclopentenedodecanoic acid), furan fatty acid (9,12-epoxy-octadeca-9,11-dienoic acid), vernolic acid (9,10-epoxyoctadec-12-enoic acid), tariric acid (6-octadecynoic acid), 6-nonadecynoic acid, santalbic acid (t11-octadecen-9-ynoic acid), 6,9-octadecenynoic acid, pyrulic acid (t10-heptadecen-8-ynoic acid), crepenyninic acid (9-octadecen-12-ynoic acid), 13,14-dihydrooropheic acid, octadecen-13-ene-9,11-diynoic acid, petroselenic acid (cis-6-octadecenoic acid), 9c,12t-octa-decadienoic acid, calendulic acid (8t10t12c-octadecatrienoic acid), catalpic acid (9t11t13c-octadecatrienoic acid), eleostearic acid (9c11t13t-octadecatrienoic acid), jacaric acid (8c10t12c-octadecatrienoic acid), punicic acid (9c11t13c-octadecatrienoic acid), parinaric acid (9c11t13t15c-octadecatetraenoic acid), pinolenic acid (all-cis-5,9,12-octadecatrienoic acid), laballenic acid (5,6-octadecadienallenic acid), ricinoleic acid (12-hydroxyoleic acid) and/or coriolic acid (13-hydroxy-9c,11t-octadecadienoic acid). The abovementioned fatty acids are, as a rule, advantageously only found in traces in the fatty acid esters or fatty acid mixtures produced by the process according to the invention, that is to say that, based on the total fatty acids, they occur to less than 30%, preferably to less than 25%, 24%, 23%, 22% or 21%, especially preferably to less than 20%, 15%, 10%, 9%, 8%, 7%, 6% or 5%, very especially preferably to less than 4%, 3%, 2% or 1%. The fatty acid esters or fatty acid mixtures produced by the process according to the invention advantageously comprise less than 0.1%, based on the total fatty acids, or no butyric acid, no cholesterol, no clupanodonic acid (=docosapentaenoic acid, C22:5$^{\Delta 4,8,12,15,21}$) and no nisinic acid (tetracosahexaenoic acid, C23:6$^{\Delta 3,8,12,15,18,21}$).

Owing to the nucleic acid sequences according to the invention, or the nucleic acid sequences used in the process according to the invention, an increase in the yield of polyunsaturated fatty acids of at least 50%, advantageously of at least 80%, especially advantageously of at least 100%, very especially advantageously of at least 150%, in comparison with the nontransgenic plant such as *Arabidopsis*, linseed, oilseed rape, soybean or *Camelina* can be obtained when compared by GC analysis.

Chemically pure polyunsaturated fatty acids or fatty acid compositions can also be synthesized by the processes described above. To this end, the fatty acids or the fatty acid compositions are isolated from the plant, in a known manner, for example via extraction, distillation, crystallization, chromatography or a combination of these methods. These chemically pure fatty acids or fatty acid compositions are advantageous for applications in the food industry sector, the cosmetic sector and especially the pharmacological industry sector.

Suitable organisms for the production in the process according to the invention are, in principle, all plants. Oil crop plants or useful plants are advantageously used in the process.

Plants which are suitable are, in principle, all those plants which are capable of synthesizing fatty acids, such as all dicotyledonous or monocotyledonous plants, algae or mosses. Advantageous plants are selected from the group of the plant families Adelotheciaceae, Anacardiaceae, Asteraceae, Apiaceae, Betulaceae, Boraginaceae, Brassicaceae, Bromeliaceae, Caricaceae, Cannabaceae, Convolvulaceae, Chenopodiaceae, Crypthecodiniaceae, Cucurbitaceae, Ditrichaceae, Elaeagnaceae, Ericaceae, Euphorbiaceae, Fabaceae, Geraniaceae, Gramineae, Juglandaceae, Lauraceae, Leguminosae, Linaceae, Prasinophyceae or vegetable plants or ornamentals such as *Tagetes*.

Examples which may be mentioned are the following plants selected from the group consisting of: Adelotheciaceae such as the genera *Physcomitrella*, for example the genus and species *Physcomitrella patens*, Anacardiaceae such as the genera *Pistacia*, *Mangifera*, *Anacardium*, for example the genus and species *Pistacia vera* [pistachio], *Mangifer indica* [mango] or *Anacardium occidentale* [cashew], Asteraceae, such as the genera *Calendula, Carthamus, Centaurea, Cichorium, Cynara, Helianthus, Lactuca, Locusta, Tagetes, Valeriana*, for example the genus and species *Calendula officinalis* [common marigold], *Carthamus tinctorius* [safflower], *Centaurea cyanus* [cornflower], *Cichorium intybus* [chicory], *Cynara scolymus* [artichoke], *Helianthus annus* [sunflower], *Lactuca sativa, Lactuca crispa, Lactuca esculenta, Lactuca scariola* L. ssp. *sativa, Lactuca scariola* L. var. *integrate, Lactuca scariola* L. var. *integrifolia, Lactuca sativa* subsp. *romana, Locusta communis, Valeriana locusta* [salad vegetables], *Tagetes lucida, Tagetes erecta* or *Tagetes tenuifolia* [african or french marigold], Apiaceae, such as the genus *Daucus*, for example the genus and species *Daucus carota* [carrot], Betulaceae, such as the genus *Corylus*, for example the genera and species *Corylus avellana* or *Corylus colurna* [hazelnut], Boraginaceae, such as the genus *Borago*, for example the genus and species *Borago officinalis* [borage], Brassicaceae, such as the genera *Brassica, Camelina, Melanosinapis, Sinapis, Arabadopsis*, for example the genera and species *Brassica napus, Brassica rapa* ssp. [oilseed rape], *Sinapis arvensis Brassica juncea, Brassica juncea* var. *juncea, Brassica juncea* var. *crispifolia, Brassica juncea* var. *foliosa, Brassica nigra, Brassica sinapioides, Camelina sativa, Melanosinapis communis* [mustard], *Brassica oleracea* [fodder beet] or *Arabidopsis thaliana*, Bromeliaceae, such as the genera *Anana, Bromelia* (pineapple), for example the genera and species *Anana comosus, Ananas ananas* or *Bromelia comosa* [pineapple], Caricaceae, such as the genus *Carica*, such as the genus and species *Carica papaya* [pawpaw], Cannabaceae, such as the genus *Cannabis*, such as the genus and species *Cannabis sative* [hemp], Convolvulaceae, such as the genera *Ipomea, Convolvulus*, for example the genera and species *Ipomoea batatus, Ipomoea pandurata, Convolvulus batatas, Convolvulus tiliaceus, Ipomoea fastigiata, Ipomoea tiliacea, Ipomoea triloba* or *Convolvulus panduratus* [sweet potato, batate], Chenopodiaceae, such as the genus *Beta*, such as the genera and species *Beta vulgaris, Beta vulgaris* var. *altissima, Beta vulgaris* var. *Vulgaris, Beta maritima, Beta vulgaris* var. *perennis, Beta vulgaris* var. *conditiva* or *Beta vulgaris* var. *esculenta* [sugarbeet], Crypthecodiniaceae, such as the genus *Crypthecodinium*, for example the genus and species *Crypteodinium cohni*, Cucurbitaceae, such as the genus *Cucubita*, for example the genera and species *Cucurbita maxima, Cucurbita mixta, Cucurbita pepo* or *Cucurbita moschata* [pumpkin/squash], Cymbellaceae, such as the genera *Amphora, Cymbella, Okedenia, Phaeodactylum, Reimeria*, for example the genus and species *Phaeodactylum tricornutum*, Ditrichaceae, such as the genera Ditrichaceae, *Astomiopsis, Ceratodon, Chrysoblastella, Ditrichum, Distichium, Eccremidium, Lophidion, Philibertiella, Pleuridium, Saelania, Trichodon, Skottsbergia*, for example the genera and species *Ceratodon antarcticus, Ceratodon columbiae, Ceratodon heterophyllus, Ceratodon purpurascens, Ceratodon purpureus, Ceratodon purpureus* ssp. *convolutus, Ceratodon purpureus* ssp. *stenocarpus, Ceratodon purpureus* var. *rotundifolius, Ceratodon ratodon, Ceratodon stenocarpus, Chrysoblastella chilensis, Ditrichum ambiguum, Ditrichum brevisetum, Ditrichum crispatissimum, Ditrichum difficile, Ditrichum falcifolium, Ditrichum flexicaule, Ditrichum giganteum, Ditrichum heteromallum, Ditrichum lineare, Ditrichum lineare, Ditrichum montanum, Ditrichum montanum, Ditrichum pallidum, Ditrichum punctulatum, Ditrichum pusillum, Ditrichum pusillum* var. *tortile, Ditrichum rhynchostegium, Ditrichum schimperi, Ditrichum tortile, Distichium capillaceum, Distichium hagenii, Distichium inclinatum, Distichium macounii, Eccremidium floridanum, Eccremidium whiteleggei, Lophidion strictus, Pleuridium acuminatum, Pleuridium alternifolium, Pleuridium holdridgei, Pleuridium mexicanum, Pleuridium ravenelii, Pleuridium subulatum, Saelania glaucescens, Trichodon borealis, Trichodon cylindricus* or *Trichodon cylindricus* var. *oblongus*, Elaeagnaceae, such as the genus *Elaeagnus*, for example the genus and species *Olea europaea* [olive], Ericaceae, such as the genus *Kalmia*, for example the genera and species *Kalmia latifolia, Kalmia angustifolia, Kalmia microphylla, Kalmia polifolia, Kalmia occidentalis, Cistus chamaerhodendros* or *Kalmia lucida* [mountain laurel], Euphorbiaceae, such as the genera *Manihot, Janipha, Jatropha, Ricinus*, for example the genera and species *Manihot utilissima, Janipha manihot, Jatropha manihot, Manihot aipil, Manihot dulcis, Manihot manihot, Manihot melanobasis, Manihot esculenta* [cassava] or *Ricinus communis* [castor-oil plant], Fabaceae, such as the genera *Pisum, Albizia, Cathormion, Feuillea, Inga, Pithecolobium, Acacia, Mimosa, Medicajo, Glycine, Dolichos, Phaseolus*, soybean, for example the genera and species *Pisum sativum, Pisum arvense, Pisum humile* [pea], *Albizia berteriana, Albizia julibrissin, Albizia lebbeck, Acacia berteriana, Acacia littoralis, Albizia berteriana, Albizzia berteriana, Cathormion berteriana, Feuillea berteriana, Inga fragrans, Pithecellobium berterianum, Pithecellobium fragrans, Pithecolobium berterianum, Pseudalbizzia berteriana, Acacia julibrissin, Acacia nemu, Albizia nemu, Feuilleea julibrissin, Mimosa julibrissin, Mimosa speciosa, Sericanrda julibrissin, Acacia lebbeck, Acacia macrophylla, Albizia lebbeck, Feuilleea lebbeck, *Mimosa lebbeck*, *Mimosa speciosa* [siris tree], *Medicago sativa*, *Medicago falcata*, *Medicago varia* [alfalfa] *Glycine max Dolichos soja*, *Glycine gracilis*, *Glycine hispida*, *Phaseolus max*, *Soja hispida* or *Soja max* [soybean], Funariaceae, such as the genera *Aphanorrhegma*, *Entosthodon*, *Funaria*, *Physcomitrella*, *Physcomitrium*, for example the genera and species *Aphanorrhegma serratum*, *Entosthodon attenuatus*, *Entosthodon bolanderi*, *Entosthodon bonplandii*, *Entosthodon californicus*, *Entosthodon drummondii*, *Entosthodon jamesonii*, *Entosthodon leibergii*, *Entosthodon neoscoticus*, *Entosthodon rubrisetus*, *Entosthodon spathulifolius*, *Entosthodon tucsoni*, *Funaria americana*, *Funaria bolanderi*, *Funaria calcarea*, *Funaria californica*, *Funaria calvescens*, *Funaria convoluta*, *Funaria flavicans*, *Funaria groutiana*, *Funaria hygrometrica*, *Funaria hygrometrica* var. *arctica*, *Funaria hygrometrica* var. *calvescens*, *Funaria hygrometrica* var. *convoluta*, *Funaria hygrometrica* var. *muralis*, *Funaria hygrometrica* var. *utahensis*, *Funaria microstoma*, *Funaria microstoma* var. *obtusifolia*, *Funaria muhlenbergii*, *Funaria orcuttii*, *Funaria plano-convexa*, *Funaria polaris*, *Funaria ravenelii*, *Funaria rubriseta*, *Funaria serrata*, *Funaria sonorae*, *Funaria sublimbatus*, *Funaria tucsoni*, *Physcomitrella californica*, *Physcomitrella patens*, *Physcomitrella readeri*, *Physcomitrium australe*, *Physcomitrium californicum*, *Physcomitrium collenchymatum*, *Physcomitrium coloradense*, *Physcomitrium cupuliferum*, *Physcomitrium drummondii*, *Physcomitrium eurystomum*, *Physcomitrium flexifolium*, *Physcomitrium hookeri*, *Physcomitrium hookeri* var. *serratum*, *Physcomitrium immersum*, *Physcomitrium kellermanii*, *Physcomitrium megalocarpum*, *Physcomitrium pyriforme*, *Physcomitrium pyriforme* var. *serratum*, *Physcomitrium rufipes*, *Physcomitrium sandbergii*, *Physcomitrium subsphaericum*, *Physcomitrium washingtoniense*, Geraniaceae, such as the genera *Pelargonium*, *Cocos*, *Oleum*, for example the genera and species *Cocos nucifera*, *Pelargonium grossularioides* or *Oleum cocois* [coconut], Gramineae, such as the genus *Saccharum*, for example the genus and species *Saccharum officinarum*, Juglandaceae, such as the genera *Juglans*, *Wallia*, for example the genera and species *Juglans regia*, *Juglans ailanthifolia*, *Juglans sieboldiana*, *Juglans cinerea*, *Wallia cinerea*, *Juglans bixbyi*, *Juglans californica*, *Juglans hindsii*, *Juglans intermedia*, *Juglans jamaicensis*, *Juglans major*, *Juglans microcarpa*, *Juglans nigra* or *Wallia nigra* [walnut], Lauraceae, such as the genera *Persea*, *Laurus*, for example the genera and species *Laurus nobilis* [bay], *Persea americana*, *Persea gratissima* or *Persea persea* [avocado], Leguminosae, such as the genus *Arachis*, for example the genus and species *Arachis hypogaea* [peanut], Linaceae, such as the genera *Adenolinum*, for example the genera and species *Linum usitatissimum*, *Linum humile*, *Linum austriacum*, *Linum bienne*, *Linum angustifolium*, *Linum catharticum*, *Linum flavum*, *Linum grandiflorum*, *Adenolinum grandiflorum*, *Linum lewisii*, *Linum narbonense*, *Linum perenne*, *Linum perenne* var. *lewisii*, *Linum pratense* or *Linum trigynum* [linseed], Lythrarieae, such as the genus *Punica*, for example the genus and species *Punica granatum* [pomegranate], Malvaceae, such as the genus *Gossypium*, for example the genera and species *Gossypium hirsutum*, *Gossypium arboreum*, *Gossypium barbadense*, *Gossypium herbaceum* or *Gossypium thurberi* [cotton], Marchantiaceae, such as the genus *Marchantia*, for example the genera and species *Marchantia berteroana*, *Marchantia foliacea*, *Marchantia macropora*, Musaceae, such as the genus *Musa*, for example the genera and species *Musa nana*, *Musa acuminata*, *Musa paradisiaca*, *Musa* spp. [banana], Onagraceae, such as the genera *Camissonia*, *Oenothera*, for example the genera and species *Oenothera biennis* or *Camissonia brevipes* [evening primrose], Palmae, such as the genus *Elacis*, for example the genus and species *Elaeis guineensis* [oil palm], Papaveraceae, such as the genus *Papaver*, for example the genera and species *Papaver orientale*, *Papaver rhoeas*, *Papaver dubium* [poppy], Pedaliaceae, such as the genus *Sesamum*, for example the genus and species *Sesamum indicum* [sesame], Piperaceae, such as the genera *Piper*, *Artanthe*, *Peperomia*, *Steffensia*, for example the genera and species *Piper aduncum*, *Piper amalago*, *Piper angustifolium*, *Piper auritum*, *Piper betel*, *Piper cubeba*, *Piper longum*, *Piper nigrum*, *Piper retrofractum*, *Artanthe adunca*, *Artanthe elongata*, *Peperomia elongata*, *Piper elongatum*, *Steffensia elongata* [cayenne pepper], Poaceae, such as the genera *Hordeum*, *Secale*, *Avena*, *Sorghum*, *Andropogon*, *Holcus*, *Panicum*, *Oryza*, *Zea* (maize), *Triticum*, for example the genera and species *Hordeum vulgare*, *Hordeum jubatum*, *Hordeum murinum*, *Hordeum secalinum*, *Hordeum distichon Hordeum aegiceras*, *Hordeum hexastichon*, *Hordeum hexastichum*, *Hordeum irregulare*, *Hordeum sativum*, *Hordeum secalinum*[barley], *Secale cereale* [rye], *Avena sativa*, *Avena fatua*, *Avena byzantina*, *Avena fatua* var. *sativa*, *Avena hybrida* [oats], *Sorghum bicolor*, *Sorghum halepense*, *Sorghum saccharatum*, *Sorghum vulgare*, *Andropogon drummondii*, *Holcus bicolor*, *Holcus sorghum*, *Sorghum aethiopicum*, *Sorghum arundinaceum*, *Sorghum caffrorum*, *Sorghum cernuum*, *Sorghum dochna*, *Sorghum drummondii*, *Sorghum durra*, *Sorghum guineense*, *Sorghum lanceolatum*, *Sorghum nervosum*, *Sorghum saccharatum*, *Sorghum subglabrescens*, *Sorghum verticilliflorum*, *Sorghum vulgare*, *Holcus halepensis*, *Sorghum miliaceum*, *Panicum militaceum* [millet], *Oryza sativa*, *Oryza latifolia* [rice], *Zea mays* [maize] *Triticum aestivum*, *Triticum durum*, *Triticum turgidum*, *Triticum hybernum*, *Triticum macha*, *Triticum sativum* or *Triticum vulgare* [wheat], Porphyridiaceae, such as the genera *Chroothece*, *Flintiella*, *Petrovanella*, *Porphyridium*, *Rhodella*, *Rhodosorus*, *Vanhoeffenia*, for example the genus and species *Porphyridium cruentum*, Proteaceae, such as the genus *Macadamia*, for example the genus and species *Macadamia intergrifolia* [macadamia], Prasinophyceae, such as the genera *Nephroselmis*, *Prasinococcus*, *Scherffelia*, *Tetraselmis*, *Mantoniella*, *Ostreococcus*, for example the genera and species *Nephroselmis olivacea*, *Prasinococcus capsulatus*, *Scherffelia dubia*, *Tetraselmis chui*, *Tetraselmis suecica*, *Mantoniella squamata*, *Ostreococcus tauri*, Rubiaceae, such as the genus *Cofea*, for example the genera and species *Cofea* spp., *Coffea arabica*, *Coffea canephora* or *Coffea liberica* [coffee], Scrophulariaceae, such as the genus *Verbascum*, for example the genera and species *Verbascum blattaria*, *Verbascum chaixii*, *Verbascum densiflorum*, *Verbascum lagurus*, *Verbascum longifolium*, *Verbascum lychnitis*, *Verbascum nigrum*, *Verbascum olympicum*, *Verbascum phlomoides*, *Verbascum phoenicum*, *Verbascum pulverulentum* or *Verbascum thapsus* [verbascum], Solanaceae, such as the genera *Capsicum*, *Nicotiana*, *Solanum*, *Lycopersicon*, for example the genera and species *Capsicum annuum*, *Capsicum annuum* var *glabriusculum*, *Capsicum frutescens* [pepper], *Capsicum annuum* [paprika], *Nicotiana tabacum*, *Nicotiana alata*, *Nicotiana attenuata*, *Nicotiana glauca*, *Nicotiana langsdorffii*, *Nicotiana obtusifolia*, *Nicotiana quadrivalvis*, *Nicotiana repanda*, *Nicotiana rustica*, *Nicotiana sylvestris* [tobacco], *Solanum tuberosum* [potato], *Solanum melongena* [eggplant] *Lycopersicon esculentum*, *Lycopersicon lycopersicum*, *Lycopersicon pyriforme*, *Solanum integrifolium* or *Solanum lycopersicum* [tomato], Sterculiaceae, such as the genus *Theobroma*, for example the genus and species *Theobroma cacao* [cacao] or Theaceae, such as the genus *Camellia*, for example the genus and species *Camellia sinensis* [tea].

Transgenic plants such as dicotyledonous or monocotyledonous plants are employed in the process according to the invention. Those which are especially advantageously employed in the process according to the invention are oil crop plants which comprise large amounts of lipid compounds, such as peanut, oilseed rape, canola, sunflower, safflower (*Carthamus tinctoria*), poppy, mustard, hemp, castor-oil plant, olive, sesame, *Calendula, Punica*, evening primrose, *verbascum*, thistle, wild roses, hazelnut, almond, *macadamia*, avocado, bay, pumpkin/squash, linseed, soybean, pistachios, borage, trees (oil palm, coconut or walnut) or arable crops such as maize, wheat, rye, oats, triticale, rice, barley, cotton, cassava, pepper, *Tagetes*, Solanaceae plants such as potato, tobacco, eggplant and tomato, *Vicia* species, pea, alfalfa or bushy plants (coffee, cacao, tea), *Salix* species. Preferred plants according to the invention are oil crop plants such as peanut, oilseed rape, canola, sunflower, safflower, poppy, mustard, hemp, castor-oil plant, olive, *Calendula, Punica*, evening primrose, pumpkin/squash, linseed, soybean, borage, trees (oil palm, coconut). Especially preferred are plants which are high in C18:2- and/or C18:3-fatty acids, such as sunflower, safflower, tobacco, *verbascum*, sesame, cotton, pumpkin/squash, poppy, evening primrose, walnut, linseed, hemp, thistle or safflower. Very especially preferred plants are plants such as safflower, sunflower, poppy, evening primrose, walnut, linseed or hemp.

In principle, all genes of the fatty acid or lipid metabolism can be used in the process for the production of polyunsaturated fatty acids, advantageously in combination with the Δ6-desaturase(s), Δ6-elongase(s), Δ5-desaturase(s), Δ5-elongase(s), Δ4-desaturase(s), Δ12-desaturase(s) and/or ω3-desaturase(s) [for the purposes of the present invention, the plural is understood as encompassing the singular and vice versa]. Genes of the fatty acid or lipid metabolism selected from the group consisting of acyl-CoA dehydrogenase(s), acyl-ACP [=acyl carrier protein] desaturase(s), acyl-ACP thioesterase(s), fatty acid acyl transferase(s), acyl-CoA:lysophospholipid acyl-transferases, fatty acid synthase(s), fatty acid hydroxylase(s), acetyl-coenzyme A carboxylase(s), acyl-coenzyme A oxidase(s), fatty acid desaturase(s), fatty acid acetylenases, lipoxygenases, triacylglycerol lipases, allenoxide synthases, hydro-peroxide lyases or fatty acid elongase(s) are advantageously used in combination with the Δ6-desaturase(s), Δ6-elongase(s), Δ5-desaturase(s), Δ5-elongase(s), Δ4-desaturase(s), Δ12-desaturase(s) and/or ω3-desaturase(s), it being possible to use individual genes or a plurality of genes in combination.

In addition to the production directly in the organism, of the starting fatty acids for the Δ6-desaturase, Δ6-elongase, Δ5-desaturase, Δ5-elongase, Δ4-desaturase, Δ12-desaturase and an ω3-desaturase used in the process of the invention, the fatty acids can also be fed externally. The production in the organism is preferred for reasons of economy. Preferred substrates are linoleic acid (C18:2$^{\Delta 9,12}$) and/or γ-linolenic acid (C18:3$^{\Delta 6,9,12}$).

To increase the yield in the above-described process for the production of oils and/or triglycerides with an advantageously elevated content of polyunsaturated fatty acids, it is advantageous to increase the amount of starting product for the synthesis of fatty acids; this can be achieved for example by introducing, into the organism, a nucleic acid which codes for a polypeptide with Δ12-desaturase. The Δ12-desaturase which is used in the process according to the invention advantageously converts oleic acid (C18:1$^{\Delta 9}$) into linoleic acid (C18:2$^{\Delta 9,12}$) or C18:2$^{\Delta 6,9}$ into C18:3$^{\Delta 6,9,12}$ (=GLA). This increasingly provides the starting materials linoleic acid (C18:2$^{\Delta 9,12}$) and γ-linolenic acid (C18:3$^{\Delta 6,9,12}$) for the synthesis of the polyunsaturated fatty acids. This is particularly advantageous in oil-producing organisms such as those from the family of the Brassicaceae, such as the genus *Brassica*, for example oilseed rape; the family of the Elaeagnaceae, such as the genus *Elaeagnus*, for example the genus and species *Olea europaea*, or the family Fabaceae, such as the genus *Glycine*, for example the genus and species *Glycine max*, which are high in oleic acid. Since these organisms are only low in linoleic acid (Mikoklajczak et al., Journal of the American Oil Chemical Society, 38, 1961, 678-681), the use of the abovementioned Δ12-desaturases for producing the starting material linoleic acid is advantageous.

Nucleic acids used in the process according to the invention are advantageously derived from plants such as algae, for example algae of the family of the Prasinophyceae such as the genera *Heteromastix, Mammella, Mantoniella, Micromonas, Nephroselmis, Ostreococcus, Prasinocladus, Prasinococcus, Pseudoscourfielda, Pycnococcus, Pyramimonas, Scherffelia* or *Tetraselmis* such as the genera and species *Heteromastix longifillis, Mamiella gilva, Mantoniella squamata, Micromonas pusilla, Nephroselmis olivacea, Nephroselmis pyriformis, Nephroselmis rotunda, Ostreococcus tauri, Ostreococcus* sp. *Prasinocladus ascus, Prasinocladus lubricus, Pycnococcus provasolii, Pyramimonas amylifera, Pyramimonas disomata, Pyramimonas obovata, Pyramimonas orientalis, Pyramimonas parkeae, Pyramimonas spinifera, Pyramimonas* sp., *Tetraselmis apiculata, Tetraselmis carteriaformis, Tetraselmis chui, Tetraselmis convolutae, Tetraselmis desikacharyl, Tetraselmis gracilis, Tetraselmis hazeni, Tetraselmis impellucida, Tetraselmis inconspicua, Tetraselmis levis, Tetraselmis maculata, Tetraselmis marina, Tetraselmis striata, Tetraselmis subcordiformis, Tetraselmis suecica, Tetraselmis tetrabrachia, Tetraselmis tetrathele, Tetraselmis verrucosa, Tetraselmis verrucosa* fo. *Rubens* or *Tetraselmis* sp. The nucleic acids used are advantageously derived from algae of the genus *Ostreococcus*. Further advantageous organisms are diatoms such as *Thalassiosira, Phaeodactylum* or *Thraustochytrium* or fungi such as *Thraustochytrium* or *Phytophthora*.

In the process according to the invention advantageously the abovementioned nucleic acid sequences or their derivatives or homologues which code for polypeptides which retain the enzymatic activity of the proteins code ford by nucleic acid sequences. These sequences, individually or in combination with the nucleic acid sequences which code for Δ6-desaturase, Δ6-elongase, Δ5-desaturase, Δ5-elongase, Δ4-desaturase, Δ12-desaturase and/or ω3-desaturase, are cloned into expression constructs and used for the introduction into, and expression in, plants. Owing to their construction, these expression constructs make possible an advantageous optimal synthesis of the polyunsaturated fatty acids produced in the process according to the invention.

In a preferred embodiment, the process furthermore comprises the step of obtaining a cell or an intact organism which comprises the nucleic acid sequences used in the process, where the cell and/or the plant is transformed with a nucleic acid sequence according to the invention which codes for the Δ6-desaturase, Δ6-elongase, Δ5-desaturase, Δ5-elongase, Δ4-desaturase, Δ12-desaturase and/or ω3-desaturase, a gene construct or a vector as described below, alone or in combination with further nucleic acid sequences which code for proteins of the fatty acid or lipid metabolism. In a further preferred embodiment, this process furthermore comprises the step of obtaining the oils, lipids or free fatty acids from the cell or plant. The culture can, for example, take the form of a fermentation culture, for example in the case of the cultivation of plant cells, or a greenhouse- or field-grown culture of a plant. The cell or the plant produced thus is advantageously a cell of an oil-producing organism, such as an oil crop, such as, for example, peanut, oilseed rape, canola, linseed, hemp, peanut, soybean, safflower, hemp, sunflowers or borage.

In the case of plant cells, plant tissue or plant organs, "growing" is understood as meaning, for example, the cultivation on or in a nutrient medium, or of the intact plant on or in a substrate, for example in a hydroponic culture, potting compost or on arable land.

For the purposes of the invention, "transgenic" or "recombinant" means with regard to, for example, a nucleic acid sequence, an expression cassette (=gene construct) or a vector comprising the nucleic acid sequence according to the invention or an organism transformed with the nucleic acid sequences, expression cassettes or vectors according to the invention, all those constructions brought about by recombinant methods in which either a) the nucleic acid sequence according to the invention, or
b) a genetic control sequence which is operably linked with the nucleic acid sequence according to the invention, for example a promoter, or
c) (a) and (b)

are not located in their natural genetic environment or have been modified by recombinant methods, it being possible for the modification to take the form of, for example, a substitution, addition, deletion, inversion or insertion of one or more nucleotide residues. The natural genetic environment is understood as meaning the natural genomic or chromosomal locus in the original organism or the presence in a genomic library. In the case of a genomic library, the natural genetic environment of the nucleic acid sequence is preferably retained, at least in part. The environment flanks the nucleic acid sequence at least on one side and has a sequence length of at least 50 bp, preferably at least 500 bp, especially preferably at least 1000 bp, most preferably at least 5000 bp. A naturally occurring expression cassette—for example the naturally occurring combination of the natural promoter of the nucleic acid sequences according to the invention with the corresponding Δ6-desaturase, Δ6-elongase, Δ5-desaturase, Δ5-elongase, Δ4-desaturase, Δ12-desaturase and/or ω3-desaturase—becomes a transgenic expression cassette when this expression cassette is modified by non-natural, synthetic ("artificial") methods such as, for example, mutagenic treatment. Suitable methods are described, for example, in U.S. Pat. No. 5,565,350 or WO 00/15815.

A transgenic plant for the purposes of the invention is therefore understood as meaning, as above, that the nucleic acids used in the process are not at their natural locus in the genome of the plant, it being possible for the nucleic acids to be expressed homologously or heterologously. However, as mentioned, transgenic also means that, while the nucleic acids according to the invention are at their natural position in the genome of the plant, the sequence has been modified with regard to the natural sequence, and/or that the regulatory sequences of the natural sequences have been modified. Transgenic is preferably understood as meaning the expression of the nucleic acids according to the invention at an unnatural locus in the genome, i.e. homologous or, preferably, heterologous expression of the nucleic acids takes place.

Host organisms for the nucleic acids, the expression cassette or the vector used in the process according to the invention are, in principle, advantageously all plants which are capable of synthesizing fatty acids, specifically unsaturated fatty acids, and/or which are suitable for the expression of recombinant genes. Examples which may be are plants such as *Arabidopsis*, Asteraceae such as *Calendula* or crop plants such as soybean, peanut, castor-oil plant, sunflower, maize, cotton, flax, oilseed rape, coconut, oil palm, safflower (*Carthamus tinctorius*) or cacao bean. Preferred plants are those which are naturally capable of synthesizing substantial amounts of oil, such as soybean, oilseed rape, coconut, oil palm, safflower, flax, hemp, castor-oil plant, *Calendula*, peanut, cacao bean or sunflower.

Plants for the purpose of the present invention include plant cells and certain tissues, organs and parts of plants in all their phenotypic forms such as anthers, fibers, root hairs, stalks, embryos, calli, cotyledons, petioles, harvested material, plant tissue, reproductive tissue and cell cultures which are derived from the actual transgenic plant and/or can be used for bringing about the transgenic plant.

Transgenic plants which comprise the polyunsaturated fatty acids synthesized in the process according to the invention can advantageously be marketed directly without there being any need for the oils, lipids or fatty acids synthesized to be isolated. Plants for the process according to the invention are listed as meaning intact plants and all plant parts, plant organs or plant parts such as leaf, stem, seeds, root, tubers, anthers, fibers, root hairs, stalks, embryos, calli, cotyledons, petioles, harvested material, plant tissue, reproductive tissue and cell cultures which are derived from the actual transgenic plant and/or can be used for bringing about the transgenic plant. In this context, the seed comprises all parts of the seed such as the seed coats, epidermal cells, seed cells, endosperm or embryonic tissue. However, the compounds produced in the process according to the invention can also be isolated from the organisms, advantageously plants, in the form of their oils, fats, lipids and/or free fatty acids. Polyunsaturated fatty acids produced by this process can be obtained by harvesting the organisms, either from the culture in which they grow, or from the field. This can be done via pressing or extraction of the plant parts, preferably the plant seeds. In this context, the oils, fats, lipids and/or free fatty acids can be obtained by pressing by what is known as cold-beating or cold-pressing without applying heat. To allow for greater ease of disruption of the plant parts, specifically the seeds, they are previously comminuted, steamed or roasted. The seeds which have been pretreated in this manner can subsequently be pressed or extracted with solvents such as warm hexane. The solvent is subsequently removed again. In this manner, more than 96% of the compounds produced in the process can be isolated. Thereafter, the resulting products are processed further, i.e. refined. In this process, substances such as the plant mucilages and suspended matter are first removed again. What is known as desliming can be effected enzymatically or, for example, chemico-physically by addition of acid such as phosphoric acid. Thereafter, the free fatty acids are removed by treatment with a base, for example sodium hydroxide solution. The resulting product is washed thoroughly with water to remove the alkali remaining in the product and then dried. To remove the pigment remaining in the product, the products are subjected to bleaching, for example using filler's earth or active charcoal. At the end, the product is deodorized, for example using steam.

An embodiment according to the invention is the use of the oils, lipids, the fatty acids and/or the fatty acid composition which have been produced by the process according to the invention or by mixing these oils, lipids and/or fatty acids with animal, microbial or vegetable oils, lipids or fatty acids in feedstuffs, foodstuffs, cosmetics or pharmaceuticals. The oils, lipids or fatty acids produced in the process of the invention can be used in the manner with which the skilled worker is familiar for mixing with other oils, lipids, fatty acids or fatty acid mixtures of animal origin, such as, for example, fish oils.

The term "oil", "lipid" or "fat" is understood as meaning a fatty acid mixture comprising unsaturated, saturated, preferably esterified, fatty acid(s), advantageously bound in triglycerides. The oil, lipid or fat is preferably high in polyunsaturated free or, advantageously, esterified fatty acid(s), in particular linoleic acid, γ-linolenic acid, dihomo-γ-linolenic acid, arachidonic acid, α-linolenic acid, stearidonic acid, eicosatetraenoic acid, eicosapentaenoic acid, docosapentaenoic acid or docosahexaenoic acid, especially advantageously arachidonic acid, eicosapentaenoic acid or docosahexaenoic acid. The amount of unsaturated esterified fatty acids preferably amounts to approximately 30%, a content of 50% is more preferred, a content of 60%, 70%, 80% or more is even more preferred. For the analysis, the fatty acid content can, for example, be determined by gas chromatography after converting the fatty acids into the methyl esters by transesterification. The oil, lipid or fat can comprise various other saturated or unsaturated fatty acids, for example calendulic acid, palmitic acid, palmitoleic acid, stearic acid, oleic acid and the like. The content of the various fatty acids in the oil or fat can vary, in particular depending on the starting organism.

The polyunsaturated fatty acids with advantageously at least four double bonds which are produced in the process are, as described above, for example sphingolipids, phosphoglycerides, lipids, glycolipids, phospholipids, monoacylglycerol, diacylglycerol, triacylglycerol or other fatty acid esters, preferably triacylglycerides.

Starting from the polyunsaturated fatty acids with advantageously at least five or six double bonds, which acids have been prepared in the process according to the invention, the polyunsaturated fatty acids which are present can be liberated for example via treatment with alkali, for example aqueous KOH or NaOH, or acid hydrolysis, advantageously in the presence of an alcohol such as methanol or ethanol, or via enzymatic cleavage, and isolated via, for example, phase separation and subsequent acidification via, for example, $H_2SO_4$. The fatty acids can also be liberated directly without the above-described processing step.

After their introduction into an organism, advantageously a plant cell or plant, the nucleic acids used in the process can either be present on a separate plasmid or, advantageously, integrated into the genome of the host cell. In the case of integration into the genome, integration can be random or else be effected by recombination such that the native gene is replaced by the copy introduced, whereby the production of the desired compound by the cell is modulated, or by the use of a gene in trans, so that the gene is linked operably with a functional expression unit which comprises at least one sequence which ensures the expression of a gene and at least one sequence which ensures the polyadenylation of a functionally transcribed gene. The nucleic acids are advantageously introduced into the organisms via multiexpression cassettes or constructs for multiparallel expression, advantageously into the plants for the multiparallel seed-specific expression of genes.

Mosses and algae are the only known plant systems which produce substantial amounts of polyunsaturated fatty acids such as arachidonic acid (ARA) and/or eicosapentaenoic acid (EPA) and/or docosahexaenoic acid (DHA). Mosses comprise PUFAs in membrane lipids, while algae, organisms which are related to algae and a few fungi also accumulate substantial amounts of PUFAs in the triacylglycerol fraction. This is why nucleic acid molecules which are isolated from such strains which also accumulate PUFAs in the triacylglycerol fraction are particularly advantageous for the process according to the invention and thus for the modification of the lipid and PUFA production system in a host, in particular plants such as oil crop plants, for example oilseed rape, canola, linseed, hemp, soybeans, sunflowers and borage. They can therefore be used advantageously in the process according to the invention.

Substrates which are advantageously suitable for the nucleic acids which are used in the process according to the invention and which code for polypeptides with Δ6-desaturase, Δ6-elongase, Δ5-desaturase, Δ5-elongase, Δ4-desaturase, Δ12-desaturase and ω3-desaturase activity and/or the further nucleic acids used, such as the nucleic acids which code for polypeptides of the fatty acid or lipid metabolism selected from the group acyl-CoA dehydrogenase(s), acyl-ACP [=acyl carrier protein] desaturase(s), acyl-ACP thioesterase(s), fatty acid acyltransferase(s), acyl-CoA:lysophospholipid acyltransferase(s), fatty acid synthase(s), fatty acid hydroxylase(s), acetyl-coenzyme A carboxylase(s), acyl-coenzyme A oxidase(s), fatty acid desaturase(s), fatty acid acetylenases, lipoxygenases, triacylglycerol lipases, allenoxide synthases, hydroperoxide lyases or fatty acid elongase(s) are advantageously $C_{16}$-, $C_{18}$- or $C_{20}$-fatty acids. The fatty acids converted as substrates in the process are preferably converted in the form of their acyl-CoA esters and/or their phospholipid esters.

To produce the long-chain PUFAs according to the invention, the polyunsaturated $C_{18}$-fatty acids must first be desaturated by the enzymatic activity of a desaturase and subsequently be elongated by at least two carbon atoms via an elongase. After one elongation cycle, this enzyme activity gives $C_{20}$-fatty acids and after two elongation cycles $C_{22}$-fatty acids. The activity of the desaturases and elongases used in the process according to the invention preferably leads to $C_{20}$- and/or $C_{22}$-fatty acids with at least four double bonds in the fatty acid molecule, preferably to give $C_{20}$-fatty acids with at least four double bonds, especially preferably to give $C_{20}$- and/or $C_{22}$-fatty acids with at least five or six double bonds, very specially preferably with six double bonds in the molecule. Produces of the process according to the invention which are especially preferred are arachidonic acid, eicosapentaenoic acid and/or docosahesaenoic acid. The $C_{20}$- and/or $C_{22}$-fatty acids with at least four double bonds in the fatty acid can be elongated by the enzymatic activity according to the invention in the form of the free fatty acid or in the form of the esters, such as phospholipids, glycolipids, sphingolipids, phosphoglycerides, monoacylglycerol, diacylglycerol or triacylglycerol.

The preferred biosynthesis site of the fatty acids, oils, lipids or fats in the plants which are advantageously used is, for example, in general the seed or cell strata of the seed, so that seed-specific expression of the nucleic acids used in the process makes sense. However, it is obvious that the biosynthesis of fatty acids, oils or lipids need not be limited to the seed tissue, but can also take place in a tissue-specific manner in all the other parts of the plant, for example in epidermal cells or in the tubers.

Owing to the use of the nucleic acids according to the invention which code for a Δ6-desaturase, Δ6-elongase, Δ5-desaturase, Δ12-desaturase and ω3-desaturase, the polyunsaturated fatty acids produced in the process can be increased by at least 5%, preferably by at least 10%, especially preferably by at least 20%, very especially preferably by at least 50% in comparison with the wild types of the plants which do not comprise the nucleic acids recombinantly.

In principle, the polyunsaturated fatty acids produced by the process according to the invention can be increased in the plants used in the process in two different ways. Advantageously, the pool of free polyunsaturated fatty acids and/or the content of the esterified polyunsaturated fatty acids produced via the process can be enlarged. Advantageously, the pool of esterified polyunsaturated fatty acids in the transgenic plants is enlarged by the process according to the invention.

The fatty acids obtained in the process are also suitable as starting material for the chemical synthesis of the products of value. They can be used, for example, in combination with one another or alone for the production of pharmaceuticals, foodstuffs, animal feed or cosmetics.

The invention furthermore relates to isolated nucleic acid sequences which code for polypeptides with Δ6-desaturase activity, selected from the group consisting of:
a) a nucleic acid sequence with the sequence shown in SEQ ID NO: 1,
b) nucleic acid sequences which code for a protein with the sequence shown in SEQ ID NO: 2, or
c) derivatives of the nucleic acid sequence shown in SEQ ID NO: 1 which code for polypeptides with at least 70% identity at the amino acid level with SEQ ID NO: 2 and which have a Δ6-desaturase activity.

The invention furthermore relates to isolated nucleic acid sequences which code for polypeptides with Δ6-elongase activity, selected from the group consisting of:
a) a nucleic acid sequence with the sequence shown in SEQ ID NO: 3, SEQ ID NO: 5 or SEQ ID NO: 7,
b) nucleic acid sequences which code for a protein with the sequence shown in SEQ ID NO: 4, SEQ ID NO: 6 or SEQ ID NO: 8, or
c) derivatives of the nucleic acid sequence shown in SEQ ID NO: 3, SEQ ID NO: 5 or SEQ ID NO: 7 which code for polypeptides with at least 70% identity at the amino acid level with SEQ ID NO: 4, SEQ ID NO: 6 or SEQ ID NO: 8 and which have a Δ6-elongase activity.

The invention furthermore relates to isolated nucleic acid sequences which code for polypeptides with Δ5-desaturase activity, selected from the group consisting of:
a) a nucleic acid sequence with the sequence shown in SEQ ID NO: 9,
b) nucleic acid sequences which code for a protein with the sequence shown in SEQ ID NO: 10, or
c) derivatives of the nucleic acid sequence shown in SEQ ID NO: 9 which code for polypeptides with at least 40% identity at the amino acid level with SEQ ID NO: 10 and which have a Δ5-desaturase activity.

The invention furthermore relates to isolated nucleic acid sequences which code for polypeptides with ω3-desaturase activity, selected from the group consisting of:
a) a nucleic acid sequence with the sequence shown in SEQ ID NO: 23,
b) nucleic acid sequences which code for a protein with the sequence shown in SEQ ID NO: 24, or
c) derivatives of the nucleic acid sequence shown in SEQ ID NO: 23 which code for polypeptides with at least 40% identity at the amino acid level with SEQ ID NO: 24 and which have a ω3-desaturase activity.

The invention furthermore relates to isolated nucleic acid sequences which code for polypeptides with Δ12-desaturase activity, selected from the group consisting of:
a) a nucleic acid sequence with the sequence shown in SEQ ID NO: 25, or
b) nucleic acid sequences which code for a protein with the sequence shown in SEQ ID NO: 26, or
c) derivatives of the nucleic acid sequence shown in SEQ ID NO: 25 which code for polypeptides with at least 40% identity at the amino acid level with SEQ ID NO: 26 and which have a Δ12-desaturase activity.

The invention furthermore relates to gene constructs which comprise the nucleic acid sequences SEQ ID NO: 1, SEQ ID NO: 3, SEQ ID NO: 5, SEQ ID NO: 7, SEQ ID NO: 9, SEQ ID NO: 23 or SEQ ID NO: 25 according to the invention, wherein the nucleic acid is linked operably with one or more regulatory signals. In addition, additional biosynthesis genes of the fatty acid or lipid metabolism comprises selected from the group acyl-CoA dehydrogenase(s), acyl-ACP [=acyl carrier protein] desaturase(s), acyl-ACP thioesterase(s), fatty acid acyltransferase(s), acyl-CoA:lysophospholipid acyltransferase(s), fatty acid synthase(s), fatty acid hydroxylase(s), acetyl-coenzyme A carboxylase(s), acyl-coenzyme A oxidase(s), fatty acid desaturase(s), fatty acid acetylenases, lipoxygenases, triacylglycerol lipases, allenoxide synthases, hydroperoxide lyases or fatty acid elongase(s) may be present in the gene construct. Advantageously, biosynthesis genes of the fatty acid or lipid metabolism selected from the group Δ4-desaturase, Δ8-desaturase, Δ9-elongase or Δ5-elongase are additionally present.

All of the nucleic acid sequences used in the process according to the invention are advantageously derived from an organism such as a plant or a microorganism. The nucleic acid sequences are preferably derived from algae such as *Ostreococcus*, fungi such as *Phytophthora* or from diatoms such as *Thalassiosira*.

The nucleic acid sequences used in the process which code for proteins with Δ6-desaturase, Δ6-elongase, Δ5-desaturase, Δ5-elongase, Δ4-desaturase, Δ12-desaturase and/or ω3-desaturase activity are advantageously introduced alone or, preferably, in combination in an expression cassette (=nucleic acid construct) which makes possible the expression of the nucleic acids in a plant. The nucleic acid construct can comprise more than one nucleic acid sequence of an enzymatic activity, such as, for example, of a Δ6-desaturase, Δ6-elongase, Δ5-desaturase, Δ5-elongase, Δ4-desaturase, Δ12-desaturase and/or ω3-desaturase.

To introduce the nucleic acids used in the process, the latter are advantageously amplified and ligated in the known manner. Preferably, a procedure following the protocol for Pfu DNA polymerase or a Pfu/Taq DNA polymerase mixture is followed. The primer(s) are selected taking into consideration the sequence to be amplified. The primers should advantageously be chosen in such a way that the amplificate comprises the entire codogenic sequence from the start codon to the stop codon. After the amplification, the amplificate is expediently analyzed. For example, a gel-electrophoretic separation can be carried out, which is followed by a quantitative and a qualitative analysis. Thereafter, the amplificate can be purified following a standard protocol (for example Qiagen). An aliquot of the purified amplificate is then available for the subsequent cloning step. Suitable cloning vectors are generally known to the skilled worker. These include, in particular, vectors which are capable of replication in microbial systems, that is to say mainly vectors which ensure efficient cloning in yeasts or fungi and which make possible the stable transformation of plants. Those which must be mentioned in particular are various binary and cointegrated vector systems which are suitable for the T-DNA-mediated transformation. Such vector systems are, as a rule, characterized in that they comprise at least the vir genes required for the *Agrobacterium*-mediated transformation and the T-DNA-delimiting sequences (T-DNA border). These vector systems advantageously also comprise further cis-regulatory regions such as promoters and terminator sequences and/or selection markers, by means of which suitably transformed organisms can be identified. While in the case of cointegrated vector systems vir genes and T-DNA sequences are arranged on the same vector, binary systems are based on at least two vectors, one of which bears vir genes, but no T-DNA, while a second one bears T-DNA, but no vir gene. Owing to this fact, the last-mentioned vectors are relatively small, easy to manipulate and to replicate both in *E. coli* and in *Agrobacterium*. These binary vectors include vectors from the series pBIB-HYG, pPZP, pBecks, pGreen. In accordance with the invention, Bin19, pBI101, pBinAR, pGPTV and pCAMBIA are used by preference. An overview of the binary vectors and their use is found in Hellens et al, Trends in Plant Science (2000) 5, 446-451. In order to prepare the vectors, the vectors can first be linearized with restriction endonuclease(s) and then modified enzymatically in a suitable manner. Thereafter, the vector is purified, and an aliquot is employed for the cloning step. In the cloning step, the enzymatically cleaved and, if appropriate, purified amplificate is cloned with vector fragments which have been prepared in a similar manner, using ligase. In this context, a particular nucleic acid construct, or vector or plasmid construct, can have one or else more than one codogenic gene segments. The codogenic gene segments in these constructs are preferably linked operably with regulatory sequences. The regulatory sequences include, in particular, plant sequences such as the above-described promoters and terminator sequences. The constructs can advantageously be stably propagated in microorganisms, in particular in *E. coli* and *Agrobacterium tumefaciens*, under selective conditions and make possible the transfer of heterologous DNA into plants or microorganisms.

The nucleic acids used in the process, the inventive nucleic acids and nucleic acid constructs, can be introduced into organisms such as microorganisms or advantageously plants, advantageously using cloning vectors, and thus be used in the transformation of plants such as those which are published and cited in: Plant Molecular Biology and Biotechnology (CRC Press, Boca Raton, Fla.), Chapter 6/7, p. 71-119 (1993); F. F. White, Vectors for Gene Transfer in Higher Plants; in: Transgenic Plants, Vol. 1, Engineering and Utilization, Ed.: Kung and R. Wu, Academic Press, 1993, 15-38; B. Jenes et al., Techniques for Gene Transfer, in: Transgenic Plants, Vol. 1, Engineering and Utilization, Ed.: Kung and R. Wu, Academic Press (1993), 128-143; Potrykus, Annu. Rev. Plant Physiol. Plant Molec. Biol. 42 (1991), 205-225. Thus, the nucleic acids, the inventive nucleic acids and nucleic acid constructs, and/or vectors used in the process can be used for the recombinant modification of a broad spectrum of organisms, advantageously plants, so that the latter become better and/or more efficient PUFA producers.

A series of mechanisms by which a modification of the Δ6-desaturase, Δ6-elongase, Δ5-desaturase, Δ12-desaturase and ω3-desaturase protein and of the further proteins used in the process, such as Δ5-elongase or Δ4-desaturase protein, is possible exist, so that the yield, production and/or production efficiency of the advantageous polyunsaturated fatty acids in a plant, preferably in an oil crop plant, can be influenced directly owing to this modified protein. The number or activity of the Δ6-desaturase, Δ6-elongase, Δ5-desaturase, Δ5-elongase, Δ4-desaturase, Δ12-desaturase and ω3-desaturase proteins or genes can be increased, so that greater amounts of the gene products and, ultimately, greater amounts of the polyunsaturated fatty acids with at least four double bonds produced in the process according to the invention are produced. A de novo synthesis in a plant which has lacked the activity and ability to biosynthesize the compounds prior to introduction of the corresponding gene(s) is also possible. This applies analogously to the combination with further desaturases or elongases or further enzymes of the fatty acid and lipid metabolism. The use of various divergent sequences, i.e. sequences which differ at the DNA sequence level, may also be advantageous in this context, or else the use of promoters for gene expression which make possible a different gene expression in the course of time, for example as a function of the degree of maturity of a seed or an oil-storing tissue.

Owing to the introduction of a Δ6-desaturase, Δ6-elongase, Δ5-desaturase, Δ5-elongase, Δ4-desaturase, Δ12-desaturase and/or ω3-desaturase gene into a plant, alone or in combination with other genes in a cell, it is not only possible to increase biosynthesis flux towards the end product, but also to increase, or to create de novo the corresponding triacylglycerol composition. Likewise, the number or activity of other genes which are involved in the import of nutrients which are required for the biosynthesis of one or more fatty acids, oils, polar and/or neutral lipids, can be increased, so that the concentration of these precursors, cofactors or intermediates within the cells or within the storage compartment is increased, whereby the ability of the cells to produce PUFAs as described below is enhanced further. By optimizing the activity or increasing the number of one or more Δ6-desaturase, Δ6-elongase, Δ5-desaturase, Δ5-elongase, Δ4-desaturase, Δ12-desaturase and/or ω3-desaturase genes which are involved in the biosynthesis of these compounds, or by destroying the activity of one or more genes which are involved in the degradation of these compounds, an enhanced yield, production and/or efficiency of production of fatty acid and lipid molecules in plants, is made possible.

The isolated nucleic acid molecules used in the process according to the invention code for proteins or parts of these, where the proteins or the individual protein or parts thereof comprise(s) an amino acid sequence with sufficient homology to an amino acid sequence which is shown in the sequences SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24 or SEQ ID NO: 26, so that the proteins or parts thereof retain Δ6-desaturase, Δ6-elongase, Δ5-desaturase, Δ5-elongase, Δ4-desaturase, Δ12-desaturase and/or ω3-desaturase activity. The proteins or parts thereof which is/are code ford by the nucleic acid molecule(s) preferably retain their essential enzymatic activity and the ability of participating in the metabolism of compounds required for the synthesis of cell membranes or lipid bodies in plants, or in the transport of molecules across these membranes. Advantageously, the proteins code ford by the nucleic acid molecules have at least approximately 40%, preferably at least approximately 50% or 60% and more preferably at least approximately 70%, 80% or 90% and most preferably at least approximately 85%, 86%, 87%, 88%, 89%, 90%, 91%, 92%, 93%, 94%, 95%, 96%, 97%, 98%, 99% or more identity with the amino acid sequences shown in SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24 or SEQ ID NO: 26. For the purposes of the invention, homology or homologous is understood as meaning identity or identical, respectively.

The homology was calculated over the entire amino acid or nucleic acid sequence region. The skilled worker has available a series of programs which are based on various algorithms for the comparison of various sequences. Here, the algorithms of Needleman and Wunsch or Smith and Waterman give particularly reliable results. The program PileUp (J. Mol. Evolution., 25, 351-360, 1987, Higgins et al., CABIOS, 5 1989: 151-153) or the programs Gap and BestFit [Needleman and Wunsch (J. Mol. Biol. 48; 443-453 (1970) and Smith and Waterman (Adv. Appl. Math. 2; 482-489 (1981)], which are comprised in the GCG software packet [Genetics Computer Group, 575 Science Drive, Madison, Wis., USA 53711 (1991)], were used for the sequence alignment. The sequence homology values which are indicated above as a percentage were determined over the entire sequence region using the program GAP and the following settings: Gap Weight: 50, Length Weight: 3, Average Match: 10.000 and Average Mismatch: 0.000. Unless otherwise specified, these settings were always used as standard settings for the sequence alignments.

Essential enzymatic activity of the Δ6-desaturase, Δ6-elongase, Δ5-desaturase, Δ5-elongase, Δ4-desaturase, Δ12-desaturase and/or ω3-desaturase used in the process according to the invention is understood as meaning that they retain at least an enzymatic activity of at least 10%, preferably 20%, especially preferably 30% and very especially 40% in comparison with the proteins/enzymes code ford by the sequence SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23 or SEQ ID NO: 25 and their derivatives and can thus participate in the metabolism of compounds required for the synthesis of fatty acids, fatty acid esters such as diacylglycerides and/or triacylglycerides in a plant or a plant cell, or in the transport of molecules across membranes, meaning $C_{20}$- or $C_{22}$-carbon chains in the fatty acid molecule with double bonds at least four, five or six positions.

Nucleic acids which can advantageously be used in the process are derived from bacteria, fungi, diatoms, animals such as *Caenorhabditis* or *Oncorhynchus* or plants such as algae or mosses, such as the genera *Shewanella, Physcomitrella, Thraustochytrium, Fusarium, Phytophthora, Ceratodon, Mantoniella, Ostreococcus, Isochrysis, Aleurita, Muscarioides, Mortierella, Borago, Phaeodactylum, Crypthecodinium,* specifically from the genera and species *Oncorhynchus mykiss, Thalassiosira pseudonona, Mantoniella squamata, Ostreococcus* sp., *Ostreococcus tauri, Euglena gracilis, Physcomitrella patens, Phytophthora infestans, Phytophthora sojae, Fusarium graminaeum, Cryptocodinium cohnii, Ceratodon purpureus, Isochrysis galbana, Aleurita farinosa, Thraustochytrium* sp., *Muscarioides viallii, Mortierella alpina, Borago officinalis, Phaeodactylum tricornutum, Caenorhabditis elegans* or particularly advantageously from *Oncorhynchus mykiss, Thalassiosira pseudonona* or *Crypthecodinium cohnii*.

Alternatively, nucleotide sequences which code for a Δ6-desaturase, Δ6-elongase, Δ5-desaturase, Δ5-elongase, Δ4-desaturase, Δ12-desaturase and/or ω3-desaturase and which advantageously hybridize under stringent conditions with a nucleotide sequence as shown in SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23 or SEQ ID NO: 25 can be used in the process according to the invention.

The nucleic acid sequences used in the process are advantageously introduced into an expression cassette which makes possible the expression of the nucleic acids in organisms such as microorganisms or plants.

In doing so, the nucleic acid sequences which code for Δ6-desaturase, Δ6-elongase, Δ5-desaturase, Δ5-elongase, Δ4-desaturase, Δ12-desaturase and/or ω3-desaturase are linked operably with one or more regulatory signals, advantageously for enhancing gene expression. These regulatory sequences are intended to make possible the specific expression of the genes and proteins. Depending on the host organism, this may mean, for example, that the gene is expressed and/or overexpressed only after induction has taken place, or else that it is expressed and/or overexpressed immediately.

For example, these regulatory sequences take the form of sequences to which inductors or repressors bind, thus controlling the expression of the nucleic acid. In addition to these novel regulatory sequences, or instead of these sequences, the natural regulation of these sequences may still be present before the actual structural genes and, if appropriate, may have been genetically modified in such a way that their natural regulation is eliminated and the expression of the genes is enhanced. However, the expression cassette (=expression construct=gene construct) can also be simpler in construction, that is to say no additional regulatory signals have been inserted before the nucleic acid sequence or its derivatives, and the natural promoter together with its regulation was not removed. Instead, the natural regulatory sequence has been mutated in such a way that regulation no longer takes place and/or gene expression is enhanced. These modified promoters can also be positioned on their own before the natural gene in the form of part-sequences (=promoter with parts of the nucleic acid sequences used in accordance with the invention) in order to enhance the activity. Moreover, the gene construct may advantageously also comprise one or more what are known as enhancer sequences in operable linkage with the promoter, which make possible an enhanced expression of the nucleic acid sequence. Additional advantageous sequences, such as further regulatory elements or terminator sequences, may also be inserted at the 3' end of the DNA sequences. The Δ6-desaturase, Δ6-elongase, Δ5-desaturase, Δ5-elongase, Δ4-desaturase, Δ12-desaturase and/or ω3-desaturase genes may be present in one or more copies of the expression cassette (=gene construct). Preferably, only one copy of the genes is present in each expression cassette. This gene construct or the gene constructs can be expressed together in the host organism. In this context, the gene construct(s) can be inserted in one or more vectors and be present in the cell in free form, or else be inserted in the genome. It is advantageous for the insertion of further genes in the host genome when the genes to be expressed are present together in one gene construct.

In this context, the regulatory sequences or factors can, as described above, preferably have a positive effect on the gene expression of the genes introduced, thus enhancing it. Thus, an enhancement of the regulatory elements, advantageously at the transcriptional level, may take place by using strong transcription signals such as promoters and/or enhancers. In addition, however, enhanced translation is also possible, for example by improving the stability of the mRNA.

A further embodiment of the invention is one or more gene constructs which comprise one or more sequences which are defined by SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23 or SEQ ID NO: 25 or its derivatives and which code for polypeptides as shown in SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24 or SEQ ID NO: 26. The abovementioned Δ6-desaturase, Δ6-elongase, Δ5-desaturase, Δ5-elongase, Δ4-desaturase, Δ12-desaturase and/or ω3-desaturase proteins lead advantageously to a desaturation or elongation of fatty acids, the substrate advantageously having one, two, three, four, five or six double bonds and advantageously 18, 20 or 22 carbon atoms in the fatty acid molecule. The same applies to their homologs, derivatives or analogs, which are linked operably with one or more regulatory signals, advantageously for enhancing gene expression.

Advantageous regulatory sequences which can be employed for the preparation of the nucleic acid sequences employed in novel process and their subsequent introduction into plants are present for example in promoters such as the cos, tac, trp, tet, trp-tet, lpp, lac, lpp-lac, lacIq, T7, T5, T3, gal, trc, ara, SP6, λ-PR or λ-PL promoter and are advantageously employed in Gram-negative bacteria. Further advantageous regulator sequences are, for example, present in the Gram-positive promoters amy and SPO2, in the yeast or fungal promoters ADC1, MFα, AC, P-60, CYC1, GAPDH, TEF, rp28, ADH or in the plant promoters CaMV/35S [Franck et al., Cell 21 (1980) 285-294], PRP1 [Ward et al., Plant. Mol. Biol. 22 (1993)], SSU, OCS, lib4, usp, STLS1, B33, nos or in the ubiquitin or phaseolin promoter. Advantageous in this context are also inducible promoters, such as the promoters described in EP-A-0 388 186 (benzenesulfonamide-inducible), Plant J. 2, 1992:397-404 (Gatz et al., tetracycline-inducible), EP-A-0 335 528 (abscissic acid-inducible) or WO 93/21334 (ethanol- or cyclohexenol-inducible) promoters. Further suitable plant promoters are the cytosolic FBPase promoter or the ST-LSI promoter of potato (Stockhaus et al., EMBO J. 8, 1989, 2445), the *glycine max* phosphoribosylpyrophosphate amidotransferase promoter (Genbank Accession No. U87999) or the node-specific promoter described in EP-A-0 249 676. Especially advantageous promoters are promoters which make possible the expression in tissues which are involved in the biosynthesis of fatty acids. Very especially advantageous are seed-specific promoters, such as the USP promoter as described, but also other promoters such as the LeB4, DC3, phaseolin or napin promoter. Further especially advantageous promoters are seed-specific promoters which can be used for monocotyledonous or dicotyledonous plants and which are described in U.S. Pat. No. 5,608,152 (oilseed rape napin promoter), WO 98/45461 (Arabidopsis oleosin promoter), U.S. Pat. No. 5,504,200 (*Phaseolus vulgaris* phaseolin promoter), WO 91/13980 (Brassica Bce4 promoter), by Baeumlein et al., Plant J., 2, 2, 1992:233-239 (LeB4 promoter from a legume), these promoters being suitable for dicots. Examples of promoters which are suitable for monocots are the barley Ipt-2 or Ipt-1 promoter (WO 95/15389 and WO 95/23230), the barley hordein promoter and other suitable promoters described in WO 99/16890.

In principle, it is possible to use all natural promoters together with their regulatory sequences, such as those mentioned above, for the novel process. It is also possible and advantageous to use synthetic promoters, either in addition or alone, in particular when they mediate seed-specific expression, such as those described in WO 99/16890.

In order to achieve a particularly high PUFA content, before in transgenic plants, the PUFA biosynthesis genes should advantageously be expressed in oil crops in a seed-specific manner. To this end, seed-specific promoters can be used, or those promoters which are active in the embryo and/or in the endosperm. In principle, seed-specific promoters can be isolated both from dicotyledonous and from monocotyledonous plants. Advantageous preferred promoters are listed hereinbelow: USP (=unknown seed protein) and vicilin (*Vicia faba*) [Bäumlein et al., Mol. Gen. Genet., 1991, 225 (3)], napin (oilseed rape) [U.S. Pat. No. 5,608,152], acyl carrier protein (oilseed rape) [U.S. Pat. No. 5,315,001 and WO 92/18634], oleosin (*Arabidopsis thaliana*) [WO 98/45461 and WO 93/20216], phaseolin (*Phaseolus vulgaris*) [U.S. Pat. No. 5,504,200], Bce4 [WO 91/13980], leguminous B4 (LegB4 promoter) [Bäumlein et al., Plant J., 2,2, 1992], Lpt2 and lpt1 (barley) [WO 95/15389 and WO95/23230], seed-specific promoters from rice, maize and wheat [WO 99/16890], Amy32b, Amy 6-6 and aleurain [U.S. Pat. No. 5,677,474], Bce4 (oilseed rape) [U.S. Pat. No. 5,530,149], glycinin (soybean) [EP 571 741], phosphoenol pyruvate carboxylase (soybean) [JP 06/62870], ADR12-2 (soybean) [WO 98/08962], isocitrate lyase (oilseed rape) [U.S. Pat. No. 5,689,040] or α-amylase (barley) [EP 781 849].

Plant gene expression can also be facilitated via a chemically inducible promoter (see review in Gatz 1997, Annu. Rev. Plant Physiol. Plant Mol. Biol., 48:89-108). Chemically inducible promoters are particularly suitable when it is desired that gene expression should take place in a time-specific manner. Examples of such promoters are a salicylic-acid-inducible promoter (WO 95/19443), a tetracycline-inducible promoter (Gatz et al. (1992) Plant J. 2, 397-404) and an ethanol-inducible promoter.

To ensure the stable integration of the biosynthesis genes into the transgenic plant over a plurality of generations, each of the nucleic acids which code for Δ6-desaturase, Δ6-elongase, Δ5-desaturase, Δ5-elongase, Δ4-desaturase, Δ12-desaturase and/or ω3-desaturase and which are used in the process should be expressed under the control of a separate promoter, preferably a promoter which differs from the other promoters, since repeating sequence motifs can lead to instability of the T-DNA, or to recombination events. In this context, the expression cassette is advantageously constructed in such a way that a promoter is followed by a suitable cleavage site, advantageously in a polylinker, for insertion of the nucleic acid to be expressed and, if appropriate, a terminator sequence is positioned behind the polylinker. This sequence is repeated several times, preferably three, four or five times, so that up to five genes can be combined in one construct and introduced into the transgenic plant in order to be expressed. Advantageously, the sequence is repeated up to three times, or as many times as required. To express the nucleic acid sequences, the latter are inserted behind the promoter via a suitable cleavage site, for example in the polylinker. Advantageously, each nucleic acid sequence has its own promoter and, if appropriate, its own terminator sequence. Such advantageous constructs are disclosed, for example, in DE 101 02 337 or DE 101 02 338. However, it is also possible to insert a plurality of nucleic acid sequences behind a promoter and, if appropriate, before a terminator sequence. Here, the insertion site, or the sequence, of the inserted nucleic acids in the expression cassette is not of critical importance, that is to say a nucleic acid sequence can be inserted at the first or last position in the cassette without its expression being substantially influenced thereby. Advantageously, different promoters such as, for example, the USP, LegB4 or DC3 promoter, and different terminator sequences can be used in the expression cassette. However, it is also possible to use only one type of promoter in the cassette. This, however, may lead to undesired recombination events.

As described above, the transcription of the genes which have been introduced should advantageously be terminated by suitable terminator sequences at the 3' end of the biosynthesis genes which have been introduced (behind the stop codon). An example of a sequence which can be used in this context is the OCS1 terminator sequence. As is the case with the promoters, different terminator sequences should be used for each gene.

As described above, the gene construct can also comprise further genes to be introduced into the organisms. It is possible and advantageous to introduce into the host plants, and to express therein, regulatory genes such as genes for inductors, repressors or enzymes which, owing to their enzyme activity, engage in the regulation of one or more genes of a biosynthesis pathway. These genes can be of heterologous or of homologous origin. Moreover, further biosynthesis genes of the fatty acid or lipid metabolism can advantageously be present in a nucleic acid construct, or gene construct; however, these genes can also be positioned on one or more further nucleic acid constructs. Biosynthesis genes of the fatty acid or lipid metabolism which are advantageously used is a gene selected from the group consisting of acyl-CoA dehydrogenase(s), acyl-ACP [=acyl carrier protein] desaturase(s), acyl-ACP thioesterase(s), fatty acid acyltransferase(s), acyl-CoA:lysophospholipid acyltransferases, fatty acid synthase(s), fatty acid hydroxylase(s), acetyl-coenzyme A carboxylase(s), acyl-coenzyme A oxidase(s), fatty acid desaturase(s), fatty acid acetylenase(s), lipoxygenase(s), triacylglycerol lipase(s), allenoxide synthase(s), hydroperoxide lyase(s) or fatty acid elongase(s) or combinations thereof. Especially advantageous nucleic acid sequences are biosynthesis genes of the fatty acid or lipid metabolism selected from the group of the acyl-CoA:lysophospholipid acyltransferase, Δ4-desaturase, Δ8-desaturase, Δ5-elongase and/or Δ9-elongase.

In this context, the abovementioned nucleic acids or genes can be cloned into expression cassettes, like those mentioned above, in combination with other elongases and desaturases and used for transforming plants with the aid of *Agrobacterium*.

Here, the regulatory sequences or factors can, as described above, preferably have a positive effect on, and thus enhance, the expression of the genes which have been introduced. Thus, enhancement of the regulatory elements can advantageously take place at the transcriptional level by using strong transcription signals such as promoters and/or enhancers. However, an enhanced translation is also possible, for example by improving the stability of the mRNA. In principle, the expression cassettes can be used directly for introduction into the plants or else be introduced into a vector.

These advantageous vectors, preferably expression vectors, comprise the nucleic acids which code for the Δ6-desaturase, Δ6-elongase, Δ5-desaturase, Δ5-elongase, Δ4-desaturase, Δ12-desaturase and/or ω3-desaturase and which are used in the process, or else a nucleic acid construct which comprises the nucleic acid used either alone or in combination with further biosynthesis genes of the fatty acid or lipid metabolism such as the acyl-CoA:lysophospholipid acyltransferases, Δ4-desaturase, Δ8-desaturase, Δ5-elongase and/or Δ9-elongase. As used in the present context, the term "vector" refers to a nucleic acid molecule which is capable of transporting another nucleic acid to which it is bound. One type of vector is a "plasmid", a circular double-stranded DNA loop into which additional DNA segments can be ligated. A further type of vector is a viral vector, it being possible for additional DNA segments to be ligated into the viral genome. Certain vectors are capable of autonomous replication in a host cell into which they have been introduced (for example bacterial vectors with bacterial replication origin). Other vectors are advantageously integrated into the genome of a host cell when they are introduced into the host cell, and thus replicate together with the host genome. Moreover, certain vectors can govern the expression of genes with which they are in operable linkage. These vectors are referred to in the present context as "expression vectors". Usually, expression vectors which are suitable for DNA recombination techniques take the form of plasmids. In the present description, "plasmid" and "vector" can be used exchangeably since the plasmid is the form of vector which is most frequently used. However, the invention is also intended to cover other forms of expression vectors, such as viral vectors, which exert similar functions. Furthermore, the term "vector" is also intended to encompass other vectors with which the skilled worker is familiar, such as phages, viruses such as SV40, CMV, TMV, transposons, IS elements, phasmids, phagemids, cosmids, linear or circular DNA.

The recombinant expression vectors advantageously used in the process comprise the nucleic acids described below or the above-described gene construct in a form which is suitable for expressing the nucleic acids used in a host cell, which means that the recombinant expression vectors comprise one or more regulatory sequences, selected on the basis of the host cells used for the expression, which regulatory sequence(s) is/are linked operably with the nucleic acid sequence to be expressed. In a recombinant expression vector, "linked operably" means that the nucleotide sequence of interest is bound to the regulatory sequence(s) in such a way that the expression of the nucleotide sequence is possible and they are bound to each other in such a way that both sequences carry out the predicted function which is ascribed to the sequence (for example in an in-vitro transcription/translation system, or in a host cell if the vector is introduced into the host cell). The term "regulatory sequence" is intended to comprise promoters, enhancers and other expression control elements (for example polyadenylation signals). These regulatory sequences are described, for example, in Goeddel: Gene Expression Technology: Methods in Enzymology 185, Academic Press, San Diego, Calif. (1990), or see: Gruber and Crosby, in: Methods in Plant Molecular Biology and Biotechnology, CRC Press, Boca Raton, Fla., Ed.: Glick and Thompson, Chapter 7, 89-108, including the references cited therein. Regulatory sequences comprise those which govern the constitutive expression of a nucleotide sequence in many types of host cell and those which govern the direct expression of the nucleotide sequence only in specific host cells under specific conditions. The skilled worker knows that the design of the expression vector can depend on factors such as the choice of host cell to be transformed, the expression level of the desired protein and the like.

The recombinant expression vectors used can be designed for the expression of Δ6-desaturases, Δ6-elongases, Δ5-desaturases, Δ5-elongaseas, Δ4-desaturases, Δ12-desaturases and/or ω3-desaturases in prokaryotic or eukaryotic cells. This is advantageous since intermediate steps of the vector construction are frequently carried out in microorganisms for the sake of simplicity. For example, the Δ6-desaturase, Δ6-elongase, Δ5-desaturase, Δ5-elongase, Δ4-desaturase, Δ12-desaturase and/or ω3-desaturase genes can be expressed in bacterial cells (using Baculovirus expression vectors), yeast and other fungal cells (see Romanos, M. A., et al. (1992) "Foreign gene expression in yeast: a review", Yeast 8:423-488; van den Hondel, C. A. M. J. J., et al. (1991) "Heterologous gene expression in filamentous fungi", in: More Gene Manipulations in Fungi, J. W. Bennet & L. L. Lasure, Ed., pp. 396-428: Academic Press: San Diego; and van den Hondel, C. A. M. J. J., & Punt, P. J. (1991) "Gene transfer systems and vector development for filamentous fungi, in: Applied Molecular Genetics of Fungi, Peberdy, J. F., et al., Ed., pp. 1-28, Cambridge University Press: Cambridge), algae (Falciatore et al., 1999, Marine Biotechnology. 1, 3:239-251), using vectors in a transformation method as described in WO 98/01572 and, preferably, in cells of multicelled plants (see Schmidt, R. and Willmitzer, L. (1988) "High efficiency *Agrobacterium tumefaciens*-mediated transformation of *Arabidopsis thaliana* leaf and cotyledon explants" Plant Cell Rep. 583-586; Plant Molecular Biology and Biotechnology, C Press, Boca Raton, Fla., Chapter 6/7, pp. 71-119 (1993); F. F. White, B. Jenes et al., Techniques for Gene Transfer, in: Transgenic Plants, Vol. 1, Engineering and Utilization, Ed.: Kung and R. Wu, Academic Press (1993), 128-43; Potrykus, Annu. Rev. Plant Physiol. Plant Molec. Biol. 42 (1991), 205-225 (and references cited therein)). Suitable host cells are furthermore discussed in Goeddel, Gene Expression Technology: Methods in Enzymology 185, Academic Press, San Diego, Calif. (1990). As an alternative, the recombinant expression vector can be transcribed and translated in vitro, for example using T7-promoter regulatory sequences and T7-polymerase.

In most cases, the expression of proteins in prokaryotes involves the use of vectors comprising constitutive or inducible promoters which govern the expression of fusion or nonfusion proteins. Typical fusion expression vectors are, inter alia, pGEX (Pharmacia Biotech Inc; Smith, D. B., and Johnson, K. S. (1988) Gene 67:31-40), pMAL (New England Biolabs, Beverly, Mass.) und pRIT5 (Pharmacia, Piscataway, N.J.), where glutathione S-transferase (GST), maltose-E binding protein and protein A, respectively, is fused with the recombinant target protein.

Examples of suitable inducible nonfusion E. coli expression vectors are, inter alia, pTrc (Amann et al. (1988) Gene 69:301-315) and pET 11d (Studier et al., Gene Expression Technology: Methods in Enzymology 185, Academic Press, San Diego, Calif. (1990) 60-89). The target gene expression from the pTrc vector is based on the transcription from a hybrid trp-lac fusion promoter by the host RNA polymerase. The target gene expression from the vector pET 11d is based on the transcription of a T7-gn10-lac fusion promoter, which is mediated by a viral RNA polymerase (T7 gn1), which is coexpressed. This viral polymerase is provided by the host strains BL21 (DE3) or HMS174 (DE3) from a resident λ-prophage which harbors a T7 gn1 gene under the transcriptional control of the lacUV 5 promoter.

Other vectors which are suitable for prokaryotic organisms are known to the skilled worker, these vectors are, for example in E. coli pLG338, pACYC184, the pBR series such as pBR322, the pUC series such as pUC18 or pUC19, the M113 mp series, pKC30, pRep4, pHS1, pHS2, pPLc236, pMBL24, pLG200, pUR290, pIN-III113-B1, λgt11 or pBdCI, in Streptomyces pIJ101, pIJ364, pIJ702 or pIJ361, in Bacillus pUB110, pC194 or pBD214, in Corynebacterium pSA77 or pAJ667.

In a further embodiment, the expression vector is a yeast expression vector. Examples for vectors for expression in the yeast S. cerevisiae comprise pYeDesaturasec1 (Baldari et al. (1987) Embo J. 6:229-234), pMFa (Kurjan and Herskowitz (1982) Cell 30:933-943), pJRY88 (Schultz et al. (1987) Gene 54:113-123) and pYES2 (Invitrogen Corporation, San Diego, Calif.). Vectors and processes for the construction of vectors which are suitable for use in other fungi, such as the filamentous fungi, comprise those which are described in detail in: van den Hondel, C. A. M. J. J., & Punt, P. J. (1991) "Gene transfer systems and vector development for filamentous fungi, in: Applied Molecular Genetics of fungi, J. F. Peberdy et al., Ed., pp. 1-28, Cambridge University Press: Cambridge, or in: More Gene Manipulations in Fungi [J. W. Bennet & L. L. Lasure, Ed., pp. 396-428: Academic Press: San Diego]. Further suitable yeast vectors are, for example, pAG-1, YEp6, YEp13 or pEMBLYe23.

As an alternative, Δ6-desaturase, Δ6-elongase, Δ5-desaturase, Δ5-elongase, Δ4-desaturase, Δ12-desaturase and/or ω3-desaturase can be expressed in insect cells using Baculovirus expression vectors. Baculovirus vectors which are available for the expression of proteins in cultured insect cells (for example Sf9 cells) comprise the pAc series (Smith et al. (1983) Mol. Cell. Biol. 3:2156-2165) and the pVL series (Lucklow and Summers (1989) Virology 170:31-39).

The abovementioned vectors are only a small overview over suitable vectors which are possible. Further plasmids are known to the skilled worker and are described, for example, in: Cloning Vectors (Ed. Pouwels, P. H., et al., Elsevier, Amsterdam-New York-Oxford, 1985, ISBN 0 444 904018). For further suitable expression systems for prokaryotic and eukaryotic cells, see the Chapters 16 and 17 in Sambrook, J., Fritsch, E. F., and Maniatis, T., Molecular Cloning: A Laboratory Manual, 2nd edition, Cold Spring Harbor Laboratory, Cold Spring Harbor Laboratory Press, Cold Spring Harbor, N.Y., 1989.

Finally, the Δ6-desaturase, Δ6-elongase, Δ5-desaturase, Δ5-elongase, Δ4-desaturase, Δ12-desaturase and/or ω3-desaturase gene can be expressed in plant cells or intact plants (for example spermatophytes such as arable crops). Examples of plant expression vectors comprise those which are described in detail in: Becker, D., Kemper, E., Schell, J., and Masterson, R. (1992) "New plant binary vectors with selectable markers located proximal to the left border", Plant Mol. Biol. 20:1195-1197; and Bevan, M. W. (1984) "Binary Agrobacterium vectors for plant transformation", Nucl. Acids Res. 12:8711-8721; Vectors for Gene Transfer in Higher Plants; in: Transgenic Plants, Vol. 1, Engineering and Utilization, Ed.: Kung and R. Wu, Academic Press, 1993, p. 15-38.

A plant expression cassette preferably comprises regulatory sequences which are capable of governing the expression of genes in plant cells and which are linked operably so that each sequence can fulfill its function, such as transcriptional termination, for example polyadenylation signals. Preferred polyadenylation signals are those which are derived from Agrobacterium tumefaciens T-DNA, such as gene 3 of the Ti plasmid pTiACH5 (Gielen et al., EMBO J. 3 (1984) 835 et seq.), which is known as octopine synthase, or functional equivalents thereof, but all other terminator sequences which are functionally active in plants are also suitable.

Since plant gene expression is very often not limited to the transcriptional level, a plant expression cassette preferably comprises other sequences which are linked operably, such as translation enhancers, for example the overdrive sequence, which enhances the tobacco mosaic virus 5'-untranslated leader sequence, which increases the protein/RNA ratio (Gallie et al., 1987, Nucl. Acids Research 15:8693-8711).

As described above, plant gene expression must be linked operably with a suitable promoter which triggers gene expression with the correct timing or in a cell- or tissue-specific manner. Utilizable promoters are constitutive promoters (Benfey et al., EMBO J. 8 (1989) 2195-2202), such as those which are derived from plant viruses, such as 35S CaMV (Franck et al., Cell 21 (1980) 285-294), 19S CaMV (see also U.S. Pat. No. 5,352,605 and WO 84/02913), or plant promoters, such as the promoter of the small Rubisco subunit, which is described in U.S. Pat. No. 4,962,028.

Other preferred sequences for use in operable linkage in plant gene expression cassettes are targeting sequences, which are required for steering the gene product into its corresponding cell compartment (see a review in Kermode, Crit. Rev. Plant Sci. 15, 4 (1996) 285-423 and references cited therein), for example into the vacuole, into the nucleus, all types of plastids, such as amyloplasts, chloroplasts, chromoplasts, the extracellular space, the mitochondria, the endoplasmid reticulum, elaioplasts, peroxisomes and other compartments of plant cells.

As described above, plant gene expression can also be facilitated via a chemically inducible promoter (see review in Gatz 1997, Annu. Rev. Plant Physiol. Plant Mol. Biol., 48:89-108). Chemically inducible promoters are particularly suitable when it is desired that the gene expression takes place in a time-specific manner. Examples of such promoters are a salicylic-acid-inducible promoter (WO 95/19443), a tetracyclin-inducible promoter (Gatz et al. (1992) Plant J. 2, 397-404) and an ethanol-inducible promoter.

Promoters which respond to biotic or abiotic stress conditions are also suitable, for example the pathogen-induced PRP1 gene promoter (Ward et al., Plant. Mol. Biol. 22 (1993) 361-366), the heat-inducible tomato hsp80 promoter (U.S. Pat. No. 5,187,267), the chill-inducible potato alpha-amylase promoter (WO 96/12814) or the wound-inducible pinII promoter (EP-A-0 375 091).

Especially preferred are those promoters which bring about the gene expression in tissues and organs in which the biosynthesis of fatty acids, lipids and oils takes place, in seed cells, such as cells of the endosperm and of the developing embryo. Suitable promoters are the oilseed rape napin gene promoter (U.S. Pat. No. 5,608,152), the *Vicia faba* USP promoter (Baeumlein et al., Mol Gen Genet, 1991, 225 (3):459-67), the *Arabidopsis* oleosin promoter (WO 98/45461), the *Phaseolus vulgaris* phaseolin promoter (U.S. Pat. No. 5,504,200), the *Brassica* Bce4 promoter (WO 91/13980) or the legumine B4 promoter (LeB4; Baeumlein et al., 1992, Plant Journal, 2 (2):233-9), and promoters which bring about the seed-specific expression in monocotyledonous plants such as maize, barley, wheat, rye, rice and the like. Suitable noteworthy promoters are the barley Ipt2 or Ipt1 gene promoter (WO 95/15389 and WO 95/23230) or the promoters from the barley hordein gene, the rice glutelin gene, the rice oryzin gene, the rice prolamin gene, the wheat gliadin gene, the wheat glutelin gene, the maize zein gene, the oat glutelin gene, the sorghum kasirin gene or the rye secalin gene, which are described in WO 99/16890.

In particular, it may be desired to bring about the multiparallel expression of the Δ6-desaturase, Δ6-elongase, Δ5-desaturase, Δ5-elongase, Δ4-desaturase, Δ12-desaturase and/or ω3-desaturase used in the process. Such expression cassettes can be introduced via a simultaneous transformation of a plurality of individual expression constructs or, preferably, by combining a plurality of expression cassettes on one construct. Also, a plurality of vectors can be transformed with in each case a plurality of expression cassettes and then transferred into the host cell.

Other promoters which are likewise especially suitable are those which bring about a plastid-specific expression, since plastids constitute the compartment in which the precursors and some end products of lipid biosynthesis are synthesized. Suitable promoters, such as the viral RNA polymerase promoter, are described in WO 95/16783 and WO 97/06250, and the cipP promoter from *Arabidopsis*, described in WO 99/46394.

Vector DNA can be introduced into prokaryotic or eukaryotic cells via conventional transformation or transfection techniques. The terms "transformation" and "transfection", conjugation and transduction, as used in the present context, are intended to comprise a multiplicity of methods known in the prior art for the introduction of foreign nucleic acid (for example DNA) into a host cell, including calcium phosphate or calcium chloride coprecipitation, DEAE-dextran-mediated transfection, lipofection, natural competence, chemically mediated transfer, electroporation or particle bombardment. Suitable methods for the transformation or transfection of host cells, including plant cells, can be found in Sambrook et al. (Molecular Cloning: A Laboratory Manual., 2nd ed., Cold Spring Harbor Laboratory, Cold Spring Harbor Laboratory Press, Cold Spring Harbor, N.Y., 1989) and other laboratory textbooks such as Methods in Molecular Biology, 1995, Vol. 44, *Agrobacterium* protocols, Ed.: Gartland and Davey, Humana Press, Totowa, N.J.

Host cells which are suitable in principle for taking up the nucleic acid according to the invention, the gene product according to the invention or the vector according to the invention are all prokaryotic or eukaryotic organisms. The host organisms which are advantageously used as intermediate hosts are microorganisms such as fungi or yeasts. Plants such as oil crop plants, which are high in lipid compounds, such as oilseed rape, evening primrose, hemp, thistle, peanut, canola, linseed, soybean, safflower, sunflower, borage, or plants such as maize, wheat, rye, oats, triticale, rice, barley, cotton, cassava, pepper, Tagetes, Solanacea plants such as potato, tobacco, eggplant and tomato, *Vicia* species, pea, alfalfa, bushy plants (coffee, cacao, tea), *Salix* species, trees (oil palm, coconut), and fodder crops. Especially preferred plants according to the invention are oil crop plants such as soybean, peanut, oilseed rape, canola, linseed, hemp, evening primrose, sunflower, safflower, trees (oil palm, coconut).

The invention furthermore relates to the nucleic acid sequences which are enumerated hereinbelow and which code for Δ6-desaturases, Δ6-elongases, Δ5-desaturases, ω3-desaturases and/or Δ12-desaturases.

Isolated nucleic acid sequences which code for polypeptides with Δ6-desaturase activity, selected from the group consisting of:
  a) a nucleic acid sequence with the sequence shown in SEQ ID NO: 1,
  b) nucleic acid sequences which code for a protein with the sequence shown in SEQ ID NO: 2, or
  c) derivatives of the nucleic acid sequence shown in SEQ ID NO: 1 which code for polypeptides with at least 70% identity at the amino acid level with SEQ ID NO: 2 and have a Δ6-desaturase activity.

Isolated nucleic acid sequences which code for polypeptides with Δ6-elongase activity, selected from the group consisting of:
  a) a nucleic acid sequence with the sequence shown in SEQ ID NO: 3, SEQ ID NO: 5 or SEQ ID NO: 7,
  b) nucleic acid sequences which code for a protein with the sequence shown in SEQ ID NO: 4, SEQ ID NO: 6 or SEQ ID NO: 8, or
  c) derivatives of the nucleic acid sequence shown in SEQ ID NO: 3, SEQ ID NO: 5 or SEQ ID NO: 7 which code for polypeptides with at least 70% identity at the amino acid level with SEQ ID NO: 4, SEQ ID NO: 6 or SEQ ID NO: 8 and which have a Δ6-elongase activity.

Isolated nucleic acid sequences which code for polypeptides with Δ5-desaturase activity, selected from the group consisting of:
  a) a nucleic acid sequence with the sequence shown in SEQ ID NO: 9,
  b) nucleic acid sequences which code for a protein with the sequence shown in SEQ ID NO: 10, or
  c) derivatives of the nucleic acid sequence shown in SEQ ID NO: 9 which code for polypeptides with at least 40% identity at the amino acid level with SEQ ID NO: 10 and which have a Δ5-desaturase activity.

Isolated nucleic acid sequences which code for polypeptides with ω3-desaturase activity, selected from the group consisting of:
  a) a nucleic acid sequence with the sequence shown in SEQ ID NO: 23,
  b) nucleic acid sequences which code for a protein with the sequence shown in SEQ ID NO: 24, or
  c) derivatives of the nucleic acid sequence shown in SEQ ID NO: 23 which code for polypeptides with at least 40% identity at the amino acid level with SEQ ID NO: 24 and which have a ω3-desaturase activity.

Isolated nucleic acid sequences which code for polypeptides with Δ12-desaturase activity, selected from the group consisting of:
- a) a nucleic acid sequence with the sequence shown in SEQ ID NO: 25, or
- b) nucleic acid sequences which code for a protein with the sequence shown in SEQ ID NO: 26, or
- c) derivatives of the nucleic acid sequence shown in SEQ ID NO: 25 which code for polypeptides with at least 40% identity at the amino acid level with SEQ ID NO: 26 and which have a Δ12-desaturase activity.

The abovementioned nucleic acids according to the invention are derived from organisms such as fungi, plants such as algae or diatoms which are capable of synthesizing PUFAs.

The isolated abovementioned nucleic acid sequences are advantageously derived from the diatom genus *Thalassiosira* or from the family Prasinophyceae such as the genus *Ostreococcus*, from the class Euglenophyceae such as the genus *Euglena* or Pythiaceae such as the genus *Phytophthora*.

Especially preferred nucleic acid sequences are derived from the genus and species *Phytophthora sojae*. In an advantageous embodiment, these nucleic acid sequences make possible the synthesis of EPA and/or ARA. The table which follows represents such advantageous nucleic acid sequences.

| Gene | Enzyme function | Protein sequence | SEQ ID |
|---|---|---|---|
| D6-Des(Ps) | Δ6-desaturase | 456 As | SEQ ID NO: 1 |
| D6-Elo(Ps) | Δ6-elongase | 304 As | SEQ ID NO: 3 |
| D6-Elo(Ps)_2 | Δ6-elongase | 278 As | SEQ ID NO: 5 |
| D6-Elo(Ps)_3 | Δ6-elongase | 278 As | SEQ ID NO: 7 |
| D5-Des(Ps) | Δ5-desaturase | 498 As | SEQ ID NO: 9 |
| D12-Des(Ps) | Δ12-desaturase | 398 As | SEQ ID NO: 25 |
| O3-Des(Ps) | ω3-desaturase | 363 As | SEQ ID NO: 23 |

As described above, the invention furthermore relates to isolated nucleic acid sequences which code for polypeptides with Δ6-desaturase, Δ6-elongase, Δ5-desaturase, ω3-desaturase and Δ12-desaturase activity where the Δ6-desaturase, Δ6-elongase, Δ5-desaturase, ω3-desaturase and/or Δ12-desaturase code ford by these nucleic acid sequences convert $C_{18}$- or $C_{20}$-fatty acids with one, two, three or four double bonds such as $C18:1^{\Delta 9}$, $C18:2^{\Delta 9,12}$ or $C18:3^{\Delta 9,12,15}$ polyunsaturated $C_{20}$-fatty acids with three or four double bonds such as $C20:3^{\Delta 8,11,14}$ or $C20:4^{\Delta 8,11,14,17}$. The fatty acids are advantageously desaturated in the phospholipids or CoA-fatty acid esters, advantageously in the CoA-fatty acid esters.

In an advantageous embodiment, the term "nucleic acid (molecule)" as used in the present context additionally comprises the untranslated sequence at the 3' and at the 5' end of the coding gene region: at least 500, preferably 200, especially preferably 100 nucleotides of the sequence upstream of the 5' end of the coding region and at least 100, preferably 50, especially preferably 20 nucleotides of the sequence downstream of the 3' end of the coding gene region. An "isolated" nucleic acid molecule is separate from other nucleic acid molecules which are present in the natural source of the nucleic acid. An "isolated" nucleic acid preferably has no sequences which naturally flank the nucleic acid in the genomic DNA of the organism from which the nucleic acid is derived (for example sequences which are located at the 5' and 3' ends of the nucleic acid). In various embodiments, the isolated Δ6-desaturase, Δ6-elongase, Δ5-desaturase, ω3-desaturase and Δ12-desaturase molecule can comprise for example fewer than approximately 5 kb, 4 kb, 3 kb, 2 kb, 1 kb, 0.5 kb or 0.1 kb of nucleotide sequences which naturally flank the nucleic acid molecule in the genomic DNA of the cell from which the nucleic acid is derived.

The nucleic acid molecules used in the process, for example a nucleic acid molecule with a nucleotide sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23 or SEQ ID NO: 25 or of a part thereof can be isolated using molecular-biological standard techniques and the sequence information provided herein. Also, for example a homologous sequence or homologous, conserved sequence regions can be identified at the DNA or amino acid level with the aid of comparative algorithms. They can be used as hybridization probe or standard hybridization techniques (such as, for example, those described in Sambrook et al., Molecular Cloning: A Laboratory Manual. 2nd ed., Cold Spring Harbor Laboratory, Cold Spring Harbor Laboratory Press, Cold Spring Harbor, N.Y., 1989) for isolating further nucleic acid sequences which can be used in the process. Moreover, a nucleic acid molecule comprising a complete sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23 or SEQ ID NO: 25 or a part thereof can be isolated by polymerase chain reaction, where oligonucleotide primers which on the basis of this sequence or on parts thereof are used (for example a nucleic acid molecule comprising the complete sequence or part thereof can be isolated by polymerase chain reaction using oligonucleotide primers which have been generated based on this same sequence). For example, mRNA can be isolated from cells (for example by means of the guanidinium thiocyanate extraction method of Chirgwin et al. (1979) Biochemistry 18:5294-5299) and cDNA by means of reverse transcriptase (for example Moloney MLV reverse transcriptase, available from Gibco/BRL, Bethesda, Md., or AMV reverse transcriptase, available from Seikagaku America, Inc., St. Petersburg, Fla.). Synthetic oligonucleotide primers for the amplification by means of polymerase chain reaction can be generated based on one of the sequences shown in SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23 or SEQ ID NO: 25 with the aid of the amino acid sequences detailed in SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24 or SEQ ID NO: 26. A nucleic acid according to the invention can be amplified by standard PCR amplification techniques using cDNA or, alternatively, genomic DNA as template and suitable oligonucleotide primers. The nucleic acid amplified thus can be cloned into a suitable vector and characterized by means of DNA sequence analysis. Oligonucleotides which correspond to a desaturase nucleotide sequence can be generated by standard synthetic methods, for example using an automatic DNA synthesizer.

Homologs of the Δ6-desaturase, Δ6-elongase, Δ5-desaturase, Δ5-elongase, Δ4-desaturase, Δ12-desaturase and/or ω3-desaturase nucleic acid sequences with the sequence SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23 or SEQ ID NO: 25 means, for example, allelic variants with at least approximately 40 or 50%, preferably at least approximately 60 or 70%, more preferably at least approximately 70 or 80%, 90% or 95% and even more preferably at least approximately 85%, 86%, 87%, 88%, 89%, 90%, 91%, 92%, 93%, 94%, 95%, 96%, 97%, 98%, 99% or more identity or homology with a nucleotide sequence shown in SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23 or SEQ ID NO: 25 or its homologs, derivatives or analogs or parts thereof. Furthermore, isolated nucleic acid molecules of a nucleotide sequence which hybridize with a nucleotide sequences shown in SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23 or SEQ ID NO: 25 or with a part thereof, for example hybridized under stringent conditions. A part thereof is understood as meaning, in accordance with the invention, that at least 25 base pairs (=bp), 50 bp, 75 bp, 100 bp, 125 bp or 150 bp, preferably at least 175 bp, 200 bp, 225 bp, 250 bp, 275 bp or 300 bp, especially preferably 350 bp, 400 bp, 450 bp, 500 bp or more base pairs are used for the hybridization. It is also possible and advantageous to use the full sequence. Allelic variants comprise in particular functional variants which can be obtained by deletion, insertion or substitution of nucleotides from/into the sequence detailed in SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23 or SEQ ID NO: 25 it being intended, however, that the enzyme activity of the resulting proteins which are synthesized is advantageously retained for the insertion of one or more genes. Proteins which retain the enzymatic activity of $\Delta 6$-desaturase, $\Delta 6$-elongase, $\Delta 5$-desaturase, $\Delta 5$-elongase, $\Delta 4$-desaturase, $\Delta 12$-desaturase and/or $\omega 3$-desaturase, i.e. whose activity is essentially not reduced, means proteins with at least 10%, preferably 20%, especially preferably 30%, very especially preferably 40% of the original enzyme activity in comparison with the protein code ford by SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23 or SEQ ID NO: 25. The homology was calculated over the entire amino acid or nucleic acid sequence region. The skilled worker has available a series of programs which are based on various algorithms for the comparison of various sequences. Here, the algorithms of Needleman and Wunsch or Smith and Waterman give particularly reliable results. The program PileUp (J. Mol. Evolution., 25, 351-360, 1987, Higgins et al., CABIOS, 5 1989: 151-153) or the programs Gap and BestFit [Needleman and Wunsch (J. Mol. Biol. 48; 443-453 (1970) and Smith and Waterman (Adv. Appl. Math. 2; 482-489 (1981)], which are comprised in the GCG software packet [Genetics Computer Group, 575 Science Drive, Madison, Wis., USA 53711 (1991)], were used for the sequence alignment. The sequence homology values which are indicated above as a percentage were determined over the entire sequence region using the program GAP and the following settings: Gap Weight: 50, Length Weight: 3, Average Match: 10.000 and Average Mismatch: 0.000. Unless otherwise specified, these settings were always used as standard settings for the sequence alignments.

Homologs of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23 or SEQ ID NO: 25 means for example also bacterial, fungal and plant homologs, truncated sequences, single-stranded DNA or RNA of the coding and noncoding DNA sequence.

Homologs of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23 or SEQ ID NO: 25 also means derivatives such as, for example, promoter variants. The promoters upstream of the nucleotide sequences detailed can be modified by one or more nucleotide exchanges, by insertion(s) and/or deletion(s) without the functionality or activity of the promoters being adversely affected, however. It is furthermore possible that the modification of the promoter sequence enhances their activity or that they are replaced entirely by more active promoters, including those from heterologous organisms.

Lipid synthesis can be divided into two sections: the synthesis of fatty acids and their binding to sn-glycerol-3-phosphate, and the addition or modification of a polar head group. Usual lipids which are used in membranes comprise phospholipids, glycolipids, sphingolipids and phosphoglycerides. Fatty acid synthesis starts with the conversion of acetyl-CoA into malonyl-CoA by acetyl-CoA carboxylase or into acetyl-ACP by acetyl transacylase. After condensation reaction, these two product molecules together form acetoacetyl-ACP, which is converted via a series of condensation, reduction and dehydratization reactions so that a saturated fatty acid molecule with the desired chain length is obtained. The production of the unsaturated fatty acids from these molecules is catalyzed by specific desaturases, either aerobically by means of molecular oxygen or anaerobically (regarding the fatty acid synthesis in microorganisms, see F. C. Neidhardt et al. (1996) *E. coli* and *Salmonella*. ASM Press: Washington, D.C., pp. 612-636 and references cited therein; Lengeler et al. (Ed.) (1999) Biology of Procaryotes. Thieme: Stuttgart, N.Y., and the references therein, and Magnuson, K., et al. (1993) Microbiological Reviews 57:522-542 and the references therein). To undergo the further elongation steps, the resulting phospholipid-bound fatty acids must be returned to the fatty acid CoA ester pool. This is made possible by acyl-CoA: lysophospholipid acyltransferases. Moreover, these enzymes are capable of transferring the elongated fatty acids from the CoA esters back to the phospholipids. If appropriate, this reaction sequence can be followed repeatedly.

Examples of precursors for the biosynthesis of PUFAs are oleic acid, linoleic acid and linolenic acid. The $C_{18}$-carbon fatty acids must be elongated to $C_{20}$ and $C_{22}$ in order to obtain fatty acids of the eicosa and docosa chain type. With the aid of the desaturases and/or elongases used in the process, arachidonic acid, eicosapentaenoic acid, and/or docosahexaenoic acid, advantageously eicosapentaenoic acid and/or docosahexaenoic acid, can be produced and subsequently employed in various applications regarding foodstuffs, feedstuffs, cosmetics or pharmaceuticals. $C_{20}$- and/or $C_{22}$-fatty acids with at least two, advantageously at least four, five or six, double bonds in the fatty acid molecule, preferably $C_{20}$- or $C_{22}$-fatty acids with advantageously five or six double bonds in the fatty acid molecule, can be prepared using the abovementioned enzymes. Substrates of the desaturases and elongases used in the process according to the invention are $C_{16}$-, $C_{18}$- or $C_{20}$-fatty acids such as, for example, linoleic acid, γ-linolenic acid, α-linolenic acid, dihomo-γ-linolenic acid, eicosatetraenoic acid or stearidonic acid. Preferred substrates are linoleic acid, γ-linolenic acid and/or α-linolenic acid, dihomo-γ-linolenic acid, arachidonic acid, eicosatetraenoic acid or eicosapentaenoic acid. The synthesized $C_{20}$- or $C_{22}$-fatty acids with at least four, five or six double bonds in the fatty acids are obtained in the process according to the invention in the form of the free fatty acid or in the form of their esters, for example in the form of their glycerides, advantageously their triglycerides.

The term "glyceride" is understood as meaning glycerol esterified with one, two or three carboxyl radicals (mono-, di- or triglyceride). "Glyceride" is also understood as meaning a mixture of various glycerides. The glyceride or glyceride mixture may comprise further additions, for example free fatty acids, antioxidants, proteins, carbohydrates, vitamins and/or other substances.

For the purposes of the invention, a "glyceride" is furthermore understood as meaning glycerol derivatives. In addition to the above-described fatty acid glycerides, these also include glycerophospholipids and glyceroglycolipids. Preferred examples which may be mentioned in this context are the glycerophospholipids such as lecithin (phosphatidylcholine), cardiolipin, phosphatidylglycerol, phosphatidylserine and alkylacylglycerophospholipids.

Furthermore, fatty acids must subsequently be translocated to various modification sites and incorporated into the triacylglycerol storage lipid. A further important step in lipid synthesis is the transfer of fatty acids to the polar head groups, for example by glycerol fatty acid acyltransferase (see Frentzen, 1998, Lipid, 100(4-5):161-166).

Publications on plant fatty acid biosynthesis and on the desaturation, the lipid metabolism and the membrane transport of lipidic compounds, on beta-oxidation, fatty acid modification and cofactors, triacylglycerol storage and triacylglycerol assembly, including the references therein, see the following papers: Kinney, 1997, Genetic Engineering, Ed.: J K Setlow, 19:149-166; Ohlrogge and Browse, 1995, Plant Cell 7:957-970; Shanklin and Cahoon, 1998, Annu. Rev. Plant Physiol. Plant Mol. Biol. 49:611-641; Voelker, 1996, Genetic Engineering, Ed.: J K Setlow, 18:111-13; Gerhardt, 1992, Prog. Lipid R. 31:397-417; Gühnemann-Schäfer & Kindl, 1995, Biochim. Biophys Acta 1256:181-186; Kunau et al., 1995, Prog. Lipid Res. 34:267-342; Stymne et al., 1993, in: Biochemistry and Molecular Biology of Membrane and Storage Lipids of Plants, Ed.: Murata and Somerville, Rockville, American Society of Plant Physiologists, 150-158, Murphy & Ross 1998, Plant Journal. 13(1):1-16.

The PUFAs produced in the process comprise a group of molecules which higher animals are no longer capable of synthesizing and must therefore take up, or which higher animals are no longer capable of synthesizing themselves in sufficient quantity and must therefore take up additional quantities, although they can be synthesized readily by other organisms such as bacteria; for example, cats are no longer capable of synthesizing arachidonic acid.

Phospholipids for the purposes of the invention are understood as meaning phosphatidylcholine, phosphatidylethanolamine, phosphatidylserine, phosphatidylglycerol and/or phosphatidylinositol, advantageously phosphatidylcholine. The terms production or productivity are known in the art and encompass the productivity within a plant cell or a plant, that is to say the content of the desired fatty acids produced in the process relative to the content of all fatty acids in this cell or plant. The terms biosynthesis or biosynthetic pathway are known in the art and comprise the synthesis of a compound, preferably an organic compound, by a cell from intermediates, for example in a multi-step and strongly regulated process. The terms catabolism or catabolic pathway are known in the art and comprise the cleavage of a compound, preferably of an organic compound, by a cell to give catabolites (in more general terms, smaller or less complex molecules), for example in a multi-step and strongly regulated process. The term metabolism is known in the art and comprises the totality of the biochemical reactions which take place in an organism. The metabolism of a certain compound (for example the metabolism of a fatty acid) thus comprises the totality of the biosynthetic pathways, modification pathways and catabolic pathways of this compound in the cell which relate to this compound.

In a further embodiment, derivatives of the nucleic acid molecule according to the invention represented in SEQ ID NO: 1, SEQ ID NO: 3, SEQ ID NO: 5, SEQ ID NO: 7, SEQ ID NO: 9, SEQ ID NO: 23 or SEQ ID NO: 25 code for proteins with at least 40%, advantageously approximately 50 or 60%, advantageously at least approximately 60 or 70% and more preferably at least approximately 70 or 80%, 80 to 90%, 90 to 95% and most preferably at least approximately 96%, 97%, 98%, 99% or more homology (=identity for the purpose of the invention) with a complete amino acid sequence of SEQ ID NO: 2, SEQ ID NO: 4, SEQ ID NO: 6, SEQ ID NO: 8, SEQ ID NO: 10, SEQ ID NO: 24 or SEQ ID NO: 26. The homology was calculated over the entire amino acid or nucleic acid sequence region. The program PileUp (J. Mol. Evolution., 25, 351-360, 1987, Higgins et al., CABIOS, 5 1989: 151-153) or the programs Gap and BestFit [Needleman and Wunsch (J. Mol. Biol. 48; 443-453 (1970) and Smith and Waterman (Adv. Appl. Math. 2; 482-489 (1981)], which are comprised in the GCG software packet [Genetics Computer Group, 575 Science Drive, Madison, Wis., USA 53711 (1991)], were used for the sequence alignment. The sequence homology values which are indicated above as a percentage were determined over the entire sequence region using the program BestFit and the following settings: Gap Weight: 50, Length Weight: 3, Average Match: 10.000 and Average Mismatch: 0.000. Unless otherwise specified, these settings were always used as standard settings for the sequence alignments.

Moreover, the invention comprises nucleic acid molecules which differ from one of the nucleotide sequences shown in SEQ ID NO: 1, SEQ ID NO: 3, SEQ ID NO: 5, SEQ ID NO: 7, SEQ ID NO: 9, SEQ ID NO: 23 or SEQ ID NO: 25 (and parts thereof) owing to the degeneracy of the genetic code and which thus code for the same Δ6-desaturase, Δ6-elongase, Δ5-desaturase, ω3-desaturase or Δ12-desaturase activity as those code ford by the nucleotide sequences shown in SEQ ID NO: 1, SEQ ID NO: 3, SEQ ID NO: 5, SEQ ID NO: 7, SEQ ID NO: 9, SEQ ID NO: 23 or SEQ ID NO: 25.

In addition to the Δ6-desaturases, Δ6-elongases, Δ5-desaturases, ω3-desaturases or Δ12-desaturases shown in SEQ ID NO: 1, SEQ ID NO: 3, SEQ ID NO: 5, SEQ ID NO: 7, SEQ ID NO: 9, SEQ ID NO: 23 or SEQ ID NO: 25 the skilled worker will recognize that DNA sequence polymorphisms which lead to changes in the amino acid sequences of the Δ6-desaturases, Δ6-elongases, Δ5-desaturases, ω3-desaturases and/or Δ12-desaturases may exist within a population. These genetic polymorphisms in the Δ6-desaturase, Δ6-elongase, Δ5-desaturase, ω3-desaturase and/or Δ12-desaturase gene may exist between individuals within a population owing to natural variation. These natural variants usually bring about a variance of 1 to 5% in the nucleotide sequence of the Δ6-desaturase, Δ6-elongase, Δ5-desaturase, ω3-desaturase and/or Δ12-desaturase gene. Each and every one of these nucleotide variations and resulting amino acid polymorphisms in the Δ6-desaturase, Δ6-elongase, Δ5-desaturase, ω3-desaturase and/or Δ12-desaturase which are the result of natural variation and do not modify the functional activity are to be encompassed by the invention.

Owing to their homology to the Δ6-desaturase, Δ6-elongase, Δ5-desaturase, Δ5-elongase, Δ4-desaturase, Δ12-desaturase and/or ω3-desaturase nucleic acids disclosed here, nucleic acid molecules which are advantageous for the process according to the invention can be isolated following standard hybridization techniques under stringent hybridization conditions, using the sequences or part thereof as hybridization probe. In this context it is possible, for example, to use isolated nucleic acid molecules which are at least 15 nucleotides in length and which hybridize under stringent conditions with the nucleic acid molecules which comprise a nucleotide sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23 or SEQ ID NO: 25. Nucleic acids with at least 25, 50, 100, 250 or more nucleotides can also be used. The term "hybridizes under stringent conditions" as used in the present context is intended to describe hybridization and washing conditions under which nucleotide sequences with at least 60% homology to one another usually remain hybridized with one another. Conditions are preferably such that sequences with at least approximately 65%, preferably at least approximately 70% and especially preferably at least approximately 75% or more homology to one another usually remain hybridized to one another. These stringent conditions are known to the skilled worker and described in Current Protocols in Molecular Biology, John Wiley & Sons, N.Y. (1989), 6.3.1-6.3.6. A preferred nonlimiting example of stringent hybridization conditions is hybridizations in 6× sodium chloride/sodium citrate (=SSC) at approximately 45° C., followed by one or more washing steps in 0.2×SSC, 0.1% SDS at 50 to 65° C. The skilled worker knows that these hybridization conditions differ depending on the type of nucleic acid and, for example when organic solvents are present, regarding temperature and buffer concentration. Under "standard hybridization conditions", for example, the hybridization temperature is, depending on the type of nucleic acid, between 42° C. and 58° C. in aqueous buffer with a concentration of 0.1 to 5×SSC (pH 7.2). If organic solvents, for example 50% formamide, are present in the abovementioned buffer, the temperature under standard conditions is approximately 42° C. The hybridization conditions for DNA:DNA hybrids, for example, are preferably 0.1×SSC and 20° C. to 45° C., preferably 30° C. to 45° C. The hybridization conditions for DNA:RNA hybrids are, for example, preferably 0.1×SSC and 30° C. to 55° C., preferably 45° C. to 55° C. The abovementioned hybridization conditions are determined by way of example for a nucleic acid with approximately 100 bp (=base pairs) in length and with a G+C content of 50% in the absence of formamide. The skilled worker knows how to determine the required hybridization conditions on the basis of the abovementioned textbooks or textbooks such as Sambrook et al., "Molecular Cloning", Cold Spring Harbor Laboratory, 1989; Hames and Higgins (Ed.) 1985, "Nucleic Acids Hybridization: A Practical Approach", IRL Press at Oxford University Press, Oxford; Brown (Ed.) 1991, "Essential Molecular Biology: A Practical Approach", IRL Press at Oxford University Press, Oxford.

In order to determine the percentage of homology (=identity) of two amino acid sequences (for example one of the sequences of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24 or SEQ ID NO: 26) or of two nucleic acids (for example SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23 or SEQ ID NO: 25) the sequences are written one under the other for an optimal comparison (for example, gaps may be introduced into the sequence of a protein or of a nucleic acid in order to generate an optimal alignment with the other protein or the other nucleic acid). Then, the amino acid residue or nucleotides at the corresponding amino acid positions or nucleotide positions are compared. If a position in a sequence is occupied by the same amino acid residue or the same nucleotide as the corresponding position in the other sequence, then the molecules are homologous at this position (i.e. amino acid or nucleic acid "homology" as used in the present context corresponds to amino acid or nucleic acid "identity"). The percentage of homology between the two sequences is a function of the number of identical positions which the sequences share (i.e. % homology=number of identical positions/total number of positions×100). The terms homology and identity are therefore to be considered as synonymous. The programs and algorithms used are described above.

An isolated nucleic acid molecule which codes for a Δ6-desaturase, Δ6-elongase, Δ5-desaturase, Δ5-elongase, Δ4-desaturase, Δ12-desaturase and/or ω3-desaturase which is homologous to a protein sequence of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24 or SEQ ID NO: 26 can be generated by introducing one or more nucleotide substitutions, additions or deletions in/into a nucleotide sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23 or SEQ ID NO: 25 so that one or more amino acid substitutions, additions or deletions are introduced in/into the protein which is code ford. Mutations in one of the sequences of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23 or SEQ ID NO: 25 can be introduced by standard techniques such as site-specific mutagenesis and PCR-mediated mutagenesis. It is preferred to generate conservative amino acid substitutions in one or more of the predicted nonessential amino acid residues. In a "conservative amino acid substitution", the amino acid residue is replaced by an amino acid residue with a similar side chain. Families of amino acid residues with similar side chains have been defined in the art. These families comprise amino acids with basic side chains (for example lysine, arginine, histidine), acidic side chains (for example aspartic acid, glutamic acid), uncharged polar side chains (for example glycine, asparagine, glutamine, serine, threonine, tyrosine, cysteine), unpolar side chains (for example alanine, valine, leucine, isoleucine, proline, phenylalanine, methionine, tryptophan), beta-branched side chains (for example threonine, valine, isoleucine) and aromatic side chains (for example tyrosine, phenylalanine, tryptophan, histidine). A predicted nonessential amino acid residue in a Δ6-desaturase, Δ6-elongase, Δ5-desaturase, Δ5-elongase, Δ4-desaturase, Δ12-desaturase or ω3-desaturase is thus preferably replaced by another amino acid residue from the same family of side chains. In another embodiment, the mutations can, alternatively, be introduced randomly over all or part of the sequence encoding the Δ6-desaturase, Δ6-elongase, Δ5-desaturase, Δ5-elongase, Δ4-desaturase, Δ12-desaturase or ω3-desaturase, for example by saturation mutagenesis, and the resulting mutants can be screened for the herein-described Δ6-desaturase, Δ6-elongase, Δ5-desaturase, Δ5-elongase, Δ4-desaturase, Δ12-desaturase and/or ω3-desaturase activity in order to identify mutants which have retained the Δ6-desaturase, Δ6-elongase, Δ5-desaturase, Δ5-elongase, Δ4-desaturase, Δ12-desaturase and/or ω3-desaturase activity. Following the mutagenesis of one of the sequences SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23 or SEQ ID NO: 25, the protein which is code ford can be expressed recombinantly, and the activity of the protein can be determined, for example using the tests described in the present text.

The invention furthermore relates to a transgenic nonhuman organism, preferably a transgenic plant, which comprises the nucleic acids SEQ ID NO: 1, SEQ ID NO: 3, SEQ ID NO: 5, SEQ ID NO: 7, SEQ ID NO: 9, SEQ ID NO: 23 or SEQ ID NO: 25 according to the invention or a gene construct or a vector which comprise these nucleic acid sequences according to the invention.

The present invention is illustrated in greater detail by the examples which follow, which are not to be construed as limiting.

EXAMPLES

Example 1

General Cloning Methods

The cloning methods such as, for example, restriction cleavages, agarose gel electrophoresis, purification of DNA fragments, transfer of nucleic acids to nitrocellulose and nylon membranes, linkage of DNA fragments, transformation of E. coli cells, bacterial cultures and the sequence analysis of recombinant DNA were carried out as described by Sambrook et al. (1989) (Cold Spring Harbor Laboratory Press: ISBN 0-87969-309-6).

Example 2

Sequence Analysis of Recombinant DNA

Recombinant DNA molecules were sequenced with an ABI laser fluorescence DNA sequencer by the method of Sanger (Sanger et al. (1977) Proc. Natl. Acad. Sci. USA74, 5463-5467). Fragments obtained by polymerase chain reaction were sequenced and verified to avoid polymerase errors in constructs to be expressed.

Example 3

Cloning of PUFA-specific Desaturases and Elongases from Phytophthora sojae

In order to search for novel genes with Δ6-, Δ5-, Δ12-, ω3-desaturase and Δ6-elongase activity, a genomic database of Phytophthora sojae (http:/genome.jgi-psf.org/sojae/sojae1.home.html). This database contains crude sequences which cover approximately 90% of the genomic DNA of the organism. Putative candidate genes were found for all the searched-for activities. By preparing and characterizing cDNA of these candidate genes, their correct coding open reading frames were found and the amino acid sequence was derived. It is as follows:

| Gene | Enzyme function | Protein sequence | SEQ ID |
|---|---|---|---|
| D6-Des(Ps) | Δ6-desaturase | 456 As | SEQ ID NO: 1 |
| D6-Elo(Ps) | Δ6-elongase | 304 As | SEQ ID NO: 3 |
| D6-Elo(Ps)_2 | Δ6-elongase | 278 As | SEQ ID NO: 5 |
| D6-Elo(Ps)_3 | Δ6-elongase | 278 As | SEQ ID NO: 7 |
| D5-Des(Ps) | Δ5-desaturase | 498 As | SEQ ID NO: 9 |
| D12-Des(Ps) | Δ12-desaturase | 398 As | SEQ ID NO: 25 |
| O3-Des(Ps) | ω3-desaturase | 363 As | SEQ ID NO: 23 |

To prepare cDNA, total RNA of Phytophthora sojae was isolated with the aid of the RNAeasy kit from Qiagen (Valencia, Calif., US). Poly-A+ RNA (mRNA) was isolated from the total RNA with the aid of oligo-dT cellulose (Sambrook et al., 1989). The RNA was subjected to reverse transcription using the Reverse Transcription System kit from Promega, and the synthesized cDNA was cloned into the lambda ZAP vector (lambda ZAP Gold, Stratagene). The cDNA was depackaged to give plasmid DNA, following the manufacturer's instructions. Then, the plasmid library was screened for the corresponding putative candidate genes (hybridization of bacterial clones, Sambrook et al. 1989), and positive clones were sequenced. The corresponding cDNA clones was then used for the PCR for cloning expression plasmids.

Example 4

Cloning of Expression Plasmids for the Heterologous Expression of Phytophthora sojae Genes in Yeasts For the heterologous expression in yeasts, the corresponding sequences are amplified via PCR with corresponding specific primers and cloned into the yeast expression vector pYES2.1-TOPO (Invitrogen) following the manufacturer's instructions. Here, only those open reading frames of the genes are amplified which code for the PUFA proteins. In addition, a Kozak sequence (Cell 1986, 44:283-292) is attached at 5':

| Gene | Base pairs | Primer | SEQ ID |
|---|---|---|---|
| D5-Des(Ps) | 1497 bp | Fwd: gccatggcccccatcgagaccgac | SEQ ID NO:27 |
| | | Rvs: ttagcccatgtggacggaca | SEQ ID NO:28 |
| D6-Des(Ps) | 1371 bp | Fwd: accatggtggatggccccaagacca | SEQ ID NO:29 |
| | | Rvs: ttacatggccgggaactcgagcagg | SEQ ID NO:30 |
| D12-Des(Ps) | 1197 bp | Fwd: gccatggcgatcctgaacccgg | SEQ ID NO:31 |
| | | Rvs: tagagcttgttcttgtaga | SEQ ID NO:32 |
| O3-Des(Ps) | 1092 bp | Fwd: gccatggcgtccaagcaggagca | SEQ ID NO:33 |
| | | Rvs: tcagttggccttagtcttggtcgcc | SEQ ID NO:34 |

-continued

| Gene | Base pairs | Primer | | SEQ ID |
|---|---|---|---|---|
| D6-Elo(Ps) | 915 bp | Fwd: | aagatggagacgaccttcgcgcgc | SEQ ID NO:35 |
| | | Rvs: | ttactgcgtcttcttggcgaccgcagcg | SEQ ID NO:36 |
| D6-Elo(Ps)_2 | 837 bp | Fwd: | gccatggcgtcggagctgctgca | SEQ ID NO:37 |
| | | Rvs: | ttagaggttcttcttggccgg | SEQ ID NO:38 |
| D6-Elo(Ps)_3 | 837 bp | Fwd: | accatgtcggccgacctgctgc | SEQ ID NO:39 |
| | | Rvs: | ttagagcttcttcttggc | SEQ ID NO:40 |

Composition of the PCR Mix (50 µl):
5.00 µl template cDNA
5.00 µl 10× buffer (Advantage polymerase)+25 mM $MgCl_2$
5.00 µl 2 mM dNTP
1.25 µl of each primer (10 µmol/µl of the 5'-ATG and of the 3'-stop primer)
0.50 µl Advantage polymerase
The Advantage polymerase from Clontech is employed.
PCR Reaction Conditions:
Annealing temperature: 1 min 55° C.
Denaturation temperature: 1 min 94° C.
Elongation temperature: 2 min 72° C.
Number of cycles: 35

The PCR products are incubated with the plasmid pYES2.1-TOPO (Invitrogen) following the manufacturer's instructions. Then, the incubation reactions are transformed into *E. coli* DH5α-cells (Invitrogen), following the manufacturer's instructions. Positive clones are identified by PCR (see reaction above), and the plasmid DNA is isolated (Qiagen Dneasy). The plasmids formed are verified by sequencing and transformed by electroporation (1500 V) into the *Saccharomyces* strain INVSc1 (invitrogen). As a control, pYES2.1 (blank vector) is transformed in parallel. The selection of the transformed yeast is carried out on Uracil drop out complete minimal medium (CMdum) agar plates with 2% glucose. After the selection, in each case three transformants are selected for the further functional expression.

To express the genes from *Phytophthora sojae*, precultures of in each case 5 ml Uracil drop out CMdum liquid medium with 2% (w/v) raffinose are first inoculated with the selected transformants and incubated for 2 days at 30° C., 200 rpm. Then, 5 ml CMdum liquid medium (without Uracil) with 2% raffinose and 300 µM various fatty acids are inoculated with the precultures to an $OD_{600}$ of 0.05. Expression is induced by the addition of 2% (w/v) galactose. The cultures are incubated for a further 96 h at 20° C.

Example 5

Cloning of Expression Plasmids for the Seed-Specific Expression in Plants

To transform plants, further transformation vectors based on pSUN-USP were generated. To this end, NotI cleavage sites were inserted at the 5' and 3' end of the coding sequences, using the following primer pairs (see the following table).
Composition of the PCR Mix (50 µl):
5.00 µl template cDNA
5.00 µl 10× buffer (Advantage polymerase)+25 mM $MgCl_2$
5.00 µl 2 mM dNTP
1.25 µl of each primer (10 µmol/µl)
0.50 µl Advantage polymerase
The Advantage polymerase from Clontech was employed.
PCR Reaction Conditions:
Annealing temperature: 1 min 55° C.
denaturing temperature: 1 min 94° C.
Elongation temperature: 2 min 72° C.
Number of cycles: 35

| Gene | Base pairs | Primer | | SEQ ID |
|---|---|---|---|---|
| D5-Des(Ps) | 1497 bp | Fwd: | gcggccgcgccatggcccccatcgagaccgac | SEQ ID NO:41 |
| | | Rvs: | gcggccgcttagcccatgtggacggaca | SEQ ID NO:42 |
| D6-Des(Ps) | 1371 bp | Fwd: | gcggccgcaccatggtggatggccccaagacca | SEQ ID NO:43 |
| | | Rvs: | gcggccgcttacatggccgggaactcgagcagg | SEQ ID NO:44 |
| D12-Des(Ps) | 1197 bp | Fwd: | gcggccgcgccatggcgatcctgaacccgg | SEQ ID NO:45 |
| | | Rvs: | gcggccgctagagcttgttcttgtaga | SEQ ID NO:46 |
| O3-Des(Ps) | 1092 bp | Fwd: | gcggccgcgccatggcgtccaagcaggagca | SEQ ID NO:47 |
| | | Rvs: | gcggccgctcagttggccttagtcttggtcgcc | SEQ ID NO:48 |
| D6-Elo(Ps) | 915 bp | Fwd: | gcggccgcaagatggagacgaccttcgcgcgc | SEQ ID NO:49 |
| | | Rvs: | gcggccgcttactgcgtcttcttggcgaccgcagcg | SEQ ID NO:50 |
| D6-Elo(Ps)_2 | 837 bp | Fwd: | gcggccgcgccatggcgtcggagctgctgca | SEQ ID NO:51 |
| | | Rvs: | gcggccgcttagaggttcttcttggccgg | SEQ ID NO:52 |
| D6-Elo(Ps)_3 | 837 bp | Fwd: | gcggccgcaccatgtcggccgacctgctgc | SEQ ID NO:53 |
| | | Rvs: | gcggccgcttagagcttcttcttggc | SEQ ID NO:54 |

The PCR products are incubated with the restriction enzyme NotI for 4 hours at 37° C. The plant expression vector pSUN300-USP is incubated in the same manner. Thereafter, the PCR products and the vector, which is 7624 bp in size, are separated by agarose gel electrophoresis and the corresponding DNA fragments are excised. The DNA is purified by means of the Qiagen Gel Purification Kit following the manufacturer's instructions. Thereafter, vector and PCR products are ligated. The Rapid Ligation Kit from Roche is used for this purpose. The resulting plasmids are verified by sequencing.

pSUN300 is a derivative of plasmid pPZP (Hajdukiewicz, P, Svab, Z, Maliga, P., (1994). The small versatile pPZP family of *Agrobacterium* binary vectors for plant transformation. Plant Mol Biol 25:989-994). pSUN-USP originated from pSUN300, by inserting a USP promoter into pSUN300 in the form of an EcoRI fragment. The polyadenylation signal is that of the *Ostreococcus* gene from the *A. tumefaciens* Ti plasmid (ocs-Terminator, Genbank Accession V00088) (De Greve, H., Dhaese, P., Seurinck, J., Lemmers, M., Van Montagu, M. and Schell, J. Nucleotide sequence and transcript map of the *Agrobacterium tumefaciens* Ti plasmid-code ford octopine synthase gene J. Mol. Appl. Genet. 1 (6), 499-511 (1982). The USP promoter corresponds to nucleotides 1 to 684 (Genbank Accession X56240), where part of the noncoding region of the USP gene is comprised in the promoter. The promoter fragment which is 684 base pairs in size was amplified by a PCR reaction following standard methods with the aid of a synthesized primer and by means of a commercially available T7 standard primer (Stratagene). (Primer sequence:

```
5'-GTCGACCCGCGGACTAGTGGGCCCTCTAGACCCGGGGGATCCGGATCTGCTGGCTATGAA-3'). [SEQ ID NO:55]
```

The PCR fragment was recut with EcoRI/SalI and inserted into the vector pSUN300 with OCS terminator. This gave rise to the plasmid with the name pSUN-USP, which can be employed for the transformation of plants by means of *Agrobacterium tumefaciens*.

Example 6

Expression of *Phytophthora sojae* Genes in Yeasts

Yeasts which had been transformed with the plasmid pYES2.1 or the plasmids pYES-d4Des(Ps), pYES-d5Des (Ps), pYES-d6Des(Ps), pYES-d12Des(Ps), pYES-o3Des (Ps), pYES-d6Elo(Ps), pYES-d6Elo-2(Ps) and pYES-d6Elo-3(Ps) as described in Example 4 were analyzed as follows:

The yeast cells from the main cultures were harvested by centrifugation (100×g, 5 min, 20° C.) and washed with 100 mM $NaHCO_3$, pH 8.0 to remove residual medium and fatty acids. Starting with the yeast cell sediments, fatty acid methyl esters (FAMEs) were prepared by acid methanolysis. To this end, the cell sediments were incubated for one hour at 80° C. together with 2 ml of 1 N methanolic sulfuric acid and 2% (v/v) of dimethoxypropane. The FAMEs were extracted twice with petroleum ether (PE). To remove nonderivatized fatty acids, the organic phases were washed in each case once with 2 ml of 100 mM $NaHCO_3$, pH 8.0 and 2 ml of distilled water. Thereafter, the PE phases were dried with $Na_2SO_4$, evaporated under argon and taken up in 100 μl of PE. The samples were separated on a DB-23 capillary column (30 m, 0.25 mm, 0.25 μm, Agilent) in a Hewlett-Packard 6850 gas chromatograph equipped with flame ionization detector. The conditions for the GLC analysis were as follows: the oven temperature was programmed from 50° C. to 250° C. with a rate of 5° C./min and finally 10 min at 250° C. (holding).

The signals were identified by comparing the retention times with corresponding fatty acid standards (Sigma). The methodology is described for example in Napier and Michaelson, 2001, Lipids. 36(8):761-766; Sayanova et al., 2001, Journal of Experimental Botany. 52(360):1581-1585, Sperling et al., 2001, Arch. Biochem. Biophys. 388(2):293-298 and Michaelson et al., 1998, FEBS Letters. 439(3):215-218.

Example 7

Functional Characterization of *Phytophthora sojae* Genes

The activity and substrate specificity of the individual genes can be determined after expression and feeding of various fatty acids. The substrates fed are present in large amounts in all transgenic yeasts, which demonstrate the uptake of these fatty acids into the yeasts. The transgenic yeasts reveal the synthesis of novel fatty acids, the products of the genes. This means that the genes from *Phytophtora sojae* can be expressed functionally.

The substrate specificity of desaturases and elongases can be determined after expression in yeast by feeding by means of various yeasts. Descriptions for the determination of the individual activities can be found in WO 93/11245 for o3-desaturases, WO 94/11516 for Δ12-desaturases, WO 93/06712, U.S. Pat. No. 5,614,393, U.S. Pat. No. 5,614,393, WO 96/21022, WO0021557 and WO 99/27111 for Δ6-desaturases, Qiu et al. 2001, J. Biol. Chem. 276, 31561-31566 for Δ4-desaturases, Hong et al. 2002, Lipids 37, 863-868 for Δ5-desaturases, for elongases in Zank, T. K. et al. Plant Journal 31:255-268, 2002.

The activity of the individual desaturases and elongases is calculated from the conversion rate using the formula [substrate/(substrate+product)*100].

Example 8

Generation of Transgenic Plants a) Generation of Transgenic Oilseed Rape Plants (Modified Method of Moloney et al., 1992, Plant Cell Reports, 8:238-242)

In order to generate transgenic oilseed rape plants, binary vectors such as the pSUN plasmids, generated as described in Example 5, with genes from *Phytophthora sojae* are transformed into *Agrobacterium tumefaciens* C58C1:pGV2260 (Deblaere et al, 1984, Nucl. Acids. Res. 13, 4777-4788). To transform oilseed rape plants (Var. *Drakkar*, NPZ Nordeutsche Pflanzenzucht, Hohenlieth, Germany), a 1:50 dilution of an overnight culture of a positively transformed agrobacterial colony in Murashige-Skoog medium (Murashige and Skoog 1962 Physiol. Plant. 15, 473) supplemented with 3% sucrose (3MS medium) is used. Petioles or hypocotyls of freshly germinated sterile oilseed rape plants (in each case approx. 1 cm$^2$) were incubated with a 1:50 agrobacterial dilution for 5-10 minutes in a Petri dish. This is followed by 3 days of coincubation in the dark at 25° C. on 3MS medium supplemented with 0.8% Bacto agar. The cultures were then grown on for 3 days at 16 hours light/8 hours dark, and then grown on in a weekly rhythm on MS medium supplemented with 500 mg/l Claforan (cefotaxim sodium), 50 mg/l kanamycin, 20 µM benzylaminopurine (BAP), now supplemented with 1.6 g/l of glucose. Growing shoots were transferred to MS medium supplemented with 2% sucrose, 250 mg/l Claforan and 0.8% Bacto agar. If no roots had developed after three weeks, 2-indolebutyric acid was added to the medium as growth hormone for rooting.

Regenerated shoots were obtained on 2MS medium supplemented with kanamycin and Claforan; after rooting, they were transferred to compost and, after growing on for two weeks in a controlled-environment cabinet or in the greenhouse, allowed to flower, and mature seeds were harvested and analyzed by lipid analysis for expression of the desaturase and/or elongase genes as described, for example, by Qiu et al. 2001, J. Biol. Chem. 276, 31561-31566.

b) Generation of Transgenic Linseed Plants

Transgenic linseed plants can be generated for example by the method of Bell et al., 1999, In Vitro Cell. Dev. Biol.-Plant. 35(6):456-465 by means of particle bombardment. *Agrobacteria*-mediated transformations can be generated for example by the method of Mlynarova et al. (1994), Plant Cell Report 13: 282-285.

Example 9

Lipid Extraction from Seeds

The effect of the genetic modification in plants, fungi, algae, ciliates or on the production of a desired compound (such as a fatty acid) can be determined by growing the modified microorganisms or the modified plant under suitable conditions (such as those described above) and analyzing the medium and/or the cellular components for the elevated production of desired product (i.e. of the lipids or a fatty acid). These analytical techniques are known to the skilled worker and comprise spectroscopy, thin-layer chromatography, various types of staining methods, enzymatic and microbiological methods and analytical chromatography such as high-performance liquid chromatography (see, for example, Ullman, Encyclopedia of Industrial Chemistry, Vol. A2, p. 89-90 and p. 443-613, VCH: Weinheim (1985); Fallon, A., et al., (1987) "Applications of HPLC in Biochemistry" in: Laboratory Techniques in Biochemistry and Molecular Biology, Vol. 17; Rehm et al. (1993) Biotechnology, Vol. 3, Chapter III: "Product recovery and purification", p. 469-714, VCH: Weinheim; Belter, P. A., et al. (1988) Bioseparations: downstream processing for Biotechnology, John Wiley and Sons; Kennedy, J. F., and Cabral, J. M. S. (1992) Recovery processes for biological Materials, John Wiley and Sons; Shaeiwitz, J. A., and Henry, J. D. (1988) Biochemical Separations, in: Ullmann's Encyclopedia of Industrial Chemistry, Vol. B3; Chapter 11, p. 1-27, VCH: Weinheim; and Dechow, F. J. (1989) Separation and purification techniques in biotechnology, Noyes Publications).

In addition to the abovementioned processes, plant lipids are extracted from plant material as described by Cahoon et al. (1999) Proc. Natl. Acad. Sci. USA 96 (22):12935-12940 and Browse et al. (1986) Analytic Biochemistry 152:141-145. The qualitative and quantitative analysis of lipids or fatty acids is described by Christie, William W., Advances in Lipid Methodology, Ayr/Scotland: Oily Press (Oily Press Lipid Library; 2); Christie, William W., Gas Chromatography and Lipids. A Practical Guide-Ayr, Scotland: Oily Press, 1989, Repr. 1992, IX, 307 pp. (Oily Press Lipid Library; 1); "Progress in Lipid Research, Oxford: Pergamon Press, 1 (1952)-16 (1977) under the title: Progress in the Chemistry of Fats and Other Lipids CODEN.

In addition to measuring the end product of the fermentation, it is also possible to analyze other components of the metabolic pathways which are used for the production of the desired compound, such as intermediates and by-products, in order to determine the overall production efficiency of the compound. The analytical methods comprise measuring the amount of nutrients in the medium (for example sugars, hydrocarbons, nitrogen sources, phosphate and other ions), measuring the biomass composition and the growth, analyzing the production of conventional metabolites of biosynthetic pathways and measuring gases which are generated during the fermentation. Standard methods for these measurements are described in Applied Microbial Physiology; A Practical Approach, P. M. Rhodes and P. F. Stanbury, Ed., IRL Press, p. 103-129; 131-163 and 165-192 (ISBN: 0199635773) and references cited therein.

One example is the analysis of fatty acids (abbreviations: FAME, fatty acid methyl ester; GC-MS, gas liquid chromatography/mass spectrometry; TAG, triacylglycerol; TLC, thin-layer chromatography).

The unambiguous detection for the presence of fatty acid products can be obtained by analyzing recombinant organisms using analytical standard methods: GC, GC-MS or TLC, as described on several occasions by Christie and the references therein (1997, in: Advances on Lipid Methodology, Fourth Edition: Christie, Oily Press, Dundee, 119-169; 1998, Gaschromatographie-Massenspektrometrie-Verfahren [Gas chromatography/mass spectrometric methods], Lipide 33:343-353).

The material to be analyzed can be disrupted by sonication, grinding in a glass mill, liquid nitrogen and grinding or via other applicable methods. After disruption, the material must be centrifuged. The sediment is resuspended in distilled water, heated for 10 minutes at 100° C., cooled on ice and recentrifuged, followed by extraction for one hour at 90° C. in 0.5 M sulfuric acid in methanol with 2% dimethoxypropane, which leads to hydrolyzed oil and lipid compounds, which give transmethylated lipids. These fatty acid methyl esters are extracted in petroleum ether and finally subjected to a GC analysis using a capillary column (Chrompack, WCOT Fused Silica, CP-Wax-52 CB, 25 µm, 0.32 mm) at a temperature gradient of between 170° C. and 240° C. for 20 minutes and 5 minutes at 240° C. The identity of the resulting fatty acid methyl esters must be defined using standards which are available from commercial sources (i.e. Sigma).

Plant material is initially homogenized mechanically by comminuting in a pestle and mortar to make it more amenable to extraction.

This is followed by heating at 100° C. for 10 minutes and, after cooling on ice, by resedimentation. The cell sediment is hydrolyzed for one hour at 90° C. with 1 M methanolic sulfuric acid and 2% dimethoxypropane, and the lipids are transmethylated. The resulting fatty acid methyl esters (FAMEs) are extracted in petroleum ether. The extracted FAMEs are analyzed by gas liquid chromatography using a capillary column (Chrompack, WCOT Fused Silica, CP-Wax-52 CB, 25 m, 0.32 mm) and a temperature gradient of from 170° C. to 240° C. in 20 minutes and 5 minutes at 240° C. The identity of the fatty acid methyl esters is confirmed by comparison with corresponding FAME standards (Sigma). The identity and position of the double bond can be analyzed further by suitable chemical derivatization of the FAME mixtures, for example to give 4,4-dimethoxyoxazoline derivatives (Christie, 1998) by means of GC-MS.

EQUIVALENTS

Many equivalents of the specific embodiments according to the invention described herein can be identified or found by the skilled worker resorting simply to routine experiments. These equivalents are intended to be within the scope of the patent claims.

We claim:

1. A process for the production of polyunsaturated $C_{20}$- or $C_{22}$-fatty acids with at least four double bonds in transgenic plants with a content of at least 15% by weight based on the total triglyceride content of the transgenic plants comprising:

a) introducing, into the transgenic plant, a nucleic acid construct which comprises nucleic acid sequences which code for a Δ6-desaturase, a Δ6-elongase and a Δ5-desaturase, or b) introducing, into the transgenic plant, a nucleic acid construct which comprises nucleic acid sequences which code for a Δ6-desaturase, a Δ6-elongase, a Δ5-desaturase, a Δ12-desaturase and ω3-desaturase, or c) introducing, into the transgenic plant, a nucleic acid construct which comprises nucleic acid sequences which code for a Δ6-desaturase, a Δ6-elongase, a Δ5-desaturase, a Δ5-elongase and Δ4-desaturase, or d) introducing, into the transgenic plant, a nucleic acid construct which comprises nucleic acid sequences which code for a Δ6-desaturase, a Δ6-elongase, a Δ5-desaturase, a Δ5-elongase, Δ4-desaturase, a Δ12-desaturase and ω3-desaturase, and e) obtaining the oils or lipids from the plants, wherein the oils or lipids comprise polyunsaturated $C_{20}$- or $C_{22}$-fatty acids with at least four double bonds with a content of at least 15% by weight based on the total triglyceride content; and wherein the nucleic acid construct comprises a nucleic acid sequence which comprises the sequence of SEQ ID NO: 25 or a nucleic acid sequence encoding a polypeptide comprising the amino acid sequence of SEQ ID NO: 26 or a nucleic acid sequence encoding a polypeptide comprising an amino acid sequence having at least 95% sequence identity with the sequence of SEQ ID NO: 26.

2. The process according to claim 1, wherein the nucleic acid construct comprises a nucleic acid sequence which comprises the sequence of SEQ ID NO: 25 or a nucleic acid sequence encoding a polypeptide comprising the amino acid sequence of SEQ ID NO: 26.

3. The process according to claim 1, wherein the polyunsaturated $C_{20}$- or $C_{22}$-fatty acid with at least four double bonds is arachidonic acid, eicosapentaenoic acid or docosahexaenoic acid.

4. The process according to claim 1, wherein the polyunsaturated $C_{20}$- or $C_{22}$-fatty acid with at least four double bonds is arachidonic acid.

5. The process according to claim 1, wherein the polyunsaturated $C_{20}$- or $C_{22}$-fatty acid with at least four double bonds is eicosapentaenoic acid or docosahexaenoic acid.

6. The process of claim 3, wherein the arachidonic acid or eicosapentaenoic acid is present in the transgenic plant with a content of at least 15% by weight based on the total triglyceride content.

7. The process according to claim 3, wherein the docosahexaenoic acid with a content of at least 4% by weight based on the total triglyceride content is present in the transgenic plant.

8. The process according to claim 1, wherein a polyunsaturated fatty acid selected from the group consisting of C22:4$^{\Delta7,10,13,16}$-, C22:5$^{\Delta4,7,10,13,16}$- or C22:5$^{\Delta7,10,13,16,19}$-fatty acid is present in the triglycerides in an amount of less than 0.5% by weight based on the total fatty acid content of the triglycerides.

9. The process according to claim 1, wherein the transgenic plant is an oil crop plant or useful plant.

10. The process according to claim 1, wherein the transgenic plant is selected from the group consisting of peanut, oilseed rape, canola, sunflower, safflower, *Carthamus tinctoria*, poppy, mustard, hemp, castor-oil plant, olive, sesame, Calendula, Punica, evening primrose, verbascum, thistle, hazelnut, almond, macadamia, avocado, bay, pumpkin, linseed, soya, pistachios, borage, oil palm, coconut, walnut, maize, wheat, rye, oats, triticale, rice, barley, cotton, cassava or pepper.

11. The process according to claim 1, wherein the polyunsaturated $C_{20}$- or $C_{22}$-fatty acids with at least four double bonds are isolated from the oils or lipids in the form of the free fatty acids.

12. An isolated nucleic acid comprising a nucleotide sequence selected from the group consisting of:
    a) the nucleotide sequence shown in SEQ ID NO: 25,
    b) a nucleotide sequence which encodes a protein comprising the polypeptide sequence shown in SEQ ID NO: 26, and
    c) a nucleotide sequence which encodes a polypeptide having at least 95% sequence identity at the amino acid level with SEQ ID NO: 26 and which has a Δ12-desaturase activity.

13. The isolated nucleic acid according to claim 12, where the nucleotide sequence is derived from a microorganism or a plant.

14. A gene construct comprising the isolated nucleic acid according to claim 12, wherein the nucleic acid is linked operably with one or more regulatory signals.

15. The gene construct according to claim 14, wherein the nucleic acid construct comprises additional biosynthesis genes of fatty acid or lipid metabolism selected from the group acyl-CoA dehydrogenase(s), acyl-ACP [=acyl carrier protein] desaturase(s), acyl-ACP thioesterase(s), fatty acid acyltransferase(s), acyl-CoA:lysophospholipid acyltransferase(s), fatty acid synthase(s), fatty acid hydroxylase(s), acetyl-coenzyme A carboxylase(s), acyl-coenzyme A oxidase(s), fatty acid desaturase(s), fatty acid acetylenases, lipoxygenases, triacylglycerol lipases, allenoxide synthases, hydroperoxide lyases or fatty acid elongase(s).

16. The gene construct as claimed in claim 14, wherein the nucleic acid construct comprises additional biosynthesis genes of fatty acid or lipid metabolism selected from the group of the Δ4-desaturases, Δ5-desaturases, Δ6-desaturases, Δ8-desaturases, Δ12-desaturases or Δ9-elongases.

17. A vector comprising the nucleic acid according to claim 12 or a gene construct comprising the nucleic acid.

18. A transgenic nonhuman organism, comprising at least one nucleic acid according to claim 12, a gene construct comprising the nucleic acid, or a vector comprising the nucleic acid, wherein the organism is a microorganism or a plant or part thereof.

19. The transgenic nonhuman organism according to claim 18, which organism is a plant.

20. An isolated nucleic acid comprising the nucleotide sequence shown in SEQ ID NO: 25, or a nucleotide sequence which encodes a protein comprising the polypeptide sequence of SEQ ID NO: 26.

21. A transgenic plant cell, plant or part thereof, comprising at least one isolated nucleic acid of claim 12 or a gene construct comprising said nucleic acid.

22. A transgenic plant cell, plant or part thereof, comprising at least one isolated nucleic acid of claim 20 or a gene construct comprising said nucleic acid.

23. The process of claim 1, wherein
    a) the nucleic acid sequence which codes for a Δ6-desaturase comprises the nucleic acid sequence of SEQ ID NO: 1, or a nucleic acid sequence encoding the polypeptide of SEQ ID NO: 2, or a nucleic acid having at least 95% identity at the amino acid level with SEQ ID NO: 2;
    b) the nucleic acid sequence which codes for a Δ6-elongase comprises the nucleic acid sequence of SEQ ID NO: 3, SEQ ID NO: 5, or SEQ ID NO: 7, or a nucleic acid sequence encoding the polypeptide of SEQ ID NO: 4, SEQ ID NO: 6, or SEQ ID NO: 8, or a nucleic acid having at least 95% identity at the amino acid level with SEQ ID NO: 4, SEQ ID NO: 6, or SEQ ID NO: 8;
    c) the nucleic acid sequence which codes for a Δ5-desaturase comprises the nucleic acid sequence of SEQ ID NO: 9, or a nucleic acid sequence encoding the polypeptide of SEQ ID NO: 10, or a nucleic acid having at least 95% identity at the amino acid level with SEQ ID NO: 10; and/or
    d) the nucleic acid sequence which codes for a ω3-desaturase comprises the nucleic acid sequence of SEQ ID NO: 23, or a nucleic acid sequence encoding the polypeptide of SEQ ID NO: 24, or a nucleic acid having at least 95% identity at the amino acid level with SEQ ID NO: 24.

24. The process of claim 1, wherein
    a) the nucleic acid sequence which codes for a Δ6-desaturase comprises the nucleic acid sequence of SEQ ID NO: 1, or a nucleic acid sequence encoding the polypeptide of SEQ ID NO: 2;
    b) the nucleic acid sequence which codes for a Δ6-elongase comprises the nucleic acid sequence of SEQ ID NO: 3, SEQ ID NO: 5, or SEQ ID NO: 7, or a nucleic acid sequence encoding the polypeptide of SEQ ID NO: 4, SEQ ID NO: 6, or SEQ ID NO: 8;
    c) the nucleic acid sequence which codes for a Δ5-desaturase comprises the nucleic acid sequence of SEQ ID NO: 9, or a nucleic acid sequence encoding the polypeptide of SEQ ID NO: 10; and/or
    d) the nucleic acid sequence which codes for a ω3-desaturase comprises the nucleic acid sequence of SEQ ID NO: 23, or a nucleic acid sequence encoding the polypeptide of SEQ ID NO: 24.

25. The gene construct of claim 14, further comprising one or more nucleic acid comprising
    a) a nucleic acid sequence which codes for a Δ6-desaturase which comprises the nucleic acid sequence of SEQ ID NO: 1, or a nucleic acid sequence encoding the polypeptide of SEQ ID NO: 2, or a nucleic acid having at least 95% identity at the amino acid level with SEQ ID NO: 2;
    b) a nucleic acid sequence which codes for a Δ6-elongase which comprises the nucleic acid sequence of SEQ ID NO: 3, SEQ ID NO: 5, or SEQ ID NO: 7, or a nucleic acid sequence encoding the polypeptide of SEQ ID NO: 4, SEQ ID NO: 6, or SEQ ID NO: 8, or a nucleic acid having at least 95% identity at the amino acid level with SEQ ID NO: 4, SEQ ID NO: 6, or SEQ ID NO: 8;

c) a nucleic acid sequence which codes for a Δ5-desaturase which comprises the nucleic acid sequence of SEQ ID NO: 9, or a nucleic acid sequence encoding the polypeptide of SEQ ID NO: 10, or a nucleic acid having at least 95% identity at the amino acid level with SEQ ID NO: 10; and/or d) a nucleic acid sequence which codes for a ω3-desaturase which comprises the nucleic acid sequence of SEQ ID NO: 23, or a nucleic acid sequence encoding the polypeptide of SEQ ID NO: 24, or a nucleic acid having at least 95% identity at the amino acid level with SEQ ID NO: 24.

26. The gene construct of claim 14, further comprising one or more nucleic acid comprising a) a nucleic acid sequence which codes for a Δ6-desaturase which comprises the nucleic acid sequence of SEQ ID NO: 1, or a nucleic acid sequence encoding the polypeptide of SEQ ID NO: 2;

b) a nucleic acid sequence which codes for a Δ6-elongase which comprises the nucleic acid sequence of SEQ ID NO: 3, SEQ ID NO: 5, or SEQ ID NO: 7, or a nucleic acid sequence encoding the polypeptide of SEQ ID NO: 4, SEQ ID NO: 6, or SEQ ID NO: 8;

c) a nucleic acid sequence which codes for a Δ5-desaturase which comprises the nucleic acid sequence of SEQ ID NO: 9, or a nucleic acid sequence encoding the polypeptide of SEQ ID NO: 10; and/or d) a nucleic acid sequence which codes for a ω3-desaturase which comprises the nucleic acid sequence of SEQ ID NO: 23, or a nucleic acid sequence encoding the polypeptide of SEQ ID NO: 24.

27. The transgenic plant cell, plant or part thereof of claim 21, further comprising one or more nucleic acid comprising a) a nucleic acid sequence which codes for a Δ6-desaturase which comprises the nucleic acid sequence of SEQ ID NO: 1, or a nucleic acid sequence encoding the polypeptide of SEQ ID NO: 2, or a nucleic acid having at least 95% identity at the amino acid level with SEQ ID NO: 2;

b) a nucleic acid sequence which codes for a Δ6-elongase which comprises the nucleic acid sequence of SEQ ID NO: 3, SEQ ID NO: 5, or SEQ ID NO: 7, or a nucleic acid sequence encoding the polypeptide of SEQ ID NO: 4, SEQ ID NO: 6, or SEQ ID NO: 8, or a nucleic acid having at least 95% identity at the amino acid level with SEQ ID NO: 4, SEQ ID NO: 6, or SEQ ID NO: 8;

c) a nucleic acid sequence which codes for a Δ5-desaturase which comprises the nucleic acid sequence of SEQ ID NO: 9, or a nucleic acid sequence encoding the polypeptide of SEQ ID NO: 10, or a nucleic acid having at least 95% identity at the amino acid level with SEQ ID NO: 10; and/or d) a nucleic acid sequence which codes for a ω3-desaturase which comprises the nucleic acid sequence of SEQ ID NO: 23, or a nucleic acid sequence encoding the polypeptide of SEQ ID NO: 24, or a nucleic acid having at least 95% identity at the amino acid level with SEQ ID NO: 24.

28. The transgenic plant cell, plant or part thereof of claim 21, further comprising one or more nucleic acid comprising a) a nucleic acid sequence which codes for a Δ6-desaturase which comprises the nucleic acid sequence of SEQ ID NO: 1, or a nucleic acid sequence encoding the polypeptide of SEQ ID NO: 2;

b) a nucleic acid sequence which codes for a Δ6-elongase which comprises the nucleic acid sequence of SEQ ID NO: 3, SEQ ID NO: 5, or SEQ ID NO: 7, or a nucleic acid sequence encoding the polypeptide of SEQ ID NO: 4, SEQ ID NO: 6, or SEQ ID NO: 8;

c) a nucleic acid sequence which codes tor a Δ5-desaturase which comprises the nucleic acid sequence of SEQ ID NO: 9, or a nucleic acid sequence encoding the polypeptide of SEQ ID NO: 10; and/or d) a nucleic acid sequence which codes for a ω3-desaturase which comprises the nucleic acid sequence of SEQ ID NO: 23, or a nucleic acid sequence encoding the polypeptide of SEQ ID NO: 24.

29. The transgenic plant cell, plant or part thereof of claim 22, further comprising one or more nucleic acid comprising a) a nucleic acid sequence which codes for a Δ6-desaturase which comprises the nucleic acid sequence of SEQ ID NO: 1, or a nucleic acid sequence encoding the polypeptide of SEQ ID NO: 2, or a nucleic acid having at least 95% identity at the amino acid level with SEQ ID NO: 2;

b) a nucleic acid sequence which codes for a Δ6-elongase which comprises the nucleic acid sequence of SEQ ID NO: 3, SEQ ID NO: 5, or SEQ ID NO: 7, or a nucleic acid sequence encoding the polypeptide of SEQ ID NO: 4, SEQ ID NO: 6, or SEQ ID NO: 8, or a nucleic acid having at least 95% identity at the amino acid level with SEQ ID NO: 4, SEQ ID NO: 6, or SEQ ID NO: 8;

c) a nucleic acid sequence which codes for a Δ6-desaturase which comprises the nucleic acid sequence of SEQ ID NO: 9, or a nucleic acid sequence encoding the polypeptide of SEQ ID NO: 10, or a nucleic acid having at least 95% identity at the amino acid level with SEQ ID NO: 10; and/or d) a nucleic acid sequence which codes for a ω3-desaturase which comprises the nucleic acid sequence of SEQ ID NO: 23, or a nucleic acid sequence encoding the polypeptide of SEQ ID NO: 24, or a nucleic acid having at least 95% identity at the amino acid level with SEQ ID NO: 24.

30. The transgenic plant cell, plant or part thereof of claim 22, further comprising one or more nucleic acid comprising a) a nucleic acid sequence which codes for a Δ6-desaturase which comprises the nucleic acid sequence of SEQ ID NO: 1, or a nucleic acid sequence encoding the polypeptide of SEQ ID NO: 2;

b) a nucleic acid sequence which codes for a Δ6-elongase which comprises the nucleic acid sequence of SEQ ID NO: 3, SEQ ID NO: 5, or SEQ ID NO: 7, or a nucleic acid sequence encoding the polypeptide of SEQ ID NO: 4, SEQ ID NO: 6, or SEQ ID NO: 8;

c) a nucleic acid sequence which codes for a Δ5-desaturase which comprises the nucleic acid sequence of SEQ ID NO: 9, or a nucleic acid sequence encoding the polypeptide of SEQ ID NO: 10; and/or d) a nucleic acid sequence which codes for a ω3-desaturase which comprises the nucleic acid sequence of SEQ ID NO: 23, or a nucleic acid sequence encoding the polypeptide of SEQ ID NO: 24.

* * * * *

UNITED STATES PATENT AND TRADEMARK OFFICE
CERTIFICATE OF CORRECTION

| | |
|---|---|
| PATENT NO. | : 8,049,064 B2 |
| APPLICATION NO. | : 11/886857 |
| DATED | : November 1, 2011 |
| INVENTOR(S) | : Petra Cirpus et al. |

Page 1 of 1

It is certified that error appears in the above-identified patent and that said Letters Patent is hereby corrected as shown below:

In claim 29, at column 130, line number 32, "c) a nucleic acid sequence which codes for a $\Delta$6-desaturase" should read -- c) a nucleic acid sequence which codes for a $\Delta$5-desaturase --

Signed and Sealed this
Thirteenth Day of March, 2012

David J. Kappos
*Director of the United States Patent and Trademark Office*

```
                        SEQUENCE LISTING

<160> NUMBER OF SEQ ID NOS: 55

<210> SEQ ID NO 1
<211> LENGTH: 1371
<212> TYPE: DNA
<213> ORGANISM: Phytophthora sojae
<220> FEATURE:
<221> NAME/KEY: CDS
<222> LOCATION: (1)..(1371)
<223> OTHER INFORMATION: Delta-6 desaturase

<400> SEQUENCE: 1 atg gtg gat ggc ccc aag acc aag cgc ctc atc tcg tgg cag gag atc        48
Met Val Asp Gly Pro Lys Thr Lys Arg Leu Ile Ser Trp Gln Glu Ile
1               5                   10                  15 cag cag cac tcg acg tac gcc aac gcg tgg atc gtc atc cac cac aag        96
Gln Gln His Ser Thr Tyr Ala Asn Ala Trp Ile Val Ile His His Lys
            20                  25                  30 gtc tac gac atc tcc aag tgg gac tcg cac ccg ggc ggc atg gtc atg       144
Val Tyr Asp Ile Ser Lys Trp Asp Ser His Pro Gly Gly Met Val Met
        35                  40                  45 ctc tcg cag gcc ggc gag gac gcc acc gac atc ttc acc gtg tgc cac       192
Leu Ser Gln Ala Gly Glu Asp Ala Thr Asp Ile Phe Thr Val Cys His
    50                  55                  60 ccg acg agc tcc tgg aag ctg ctg gag cag ttc tac atc ggc gac gtg       240
Pro Thr Ser Ser Trp Lys Leu Leu Glu Gln Phe Tyr Ile Gly Asp Val
65                  70                  75                  80 gac gag agc acg gcc ccg ggc acg acc ggc ctc tcg gag gag cag aag       288
Asp Glu Ser Thr Ala Pro Gly Thr Thr Gly Leu Ser Glu Glu Gln Lys
                85                  90                  95 gcc aag aag gcc aag acg aac gag ttc atc agc gcc tac cgc cgc ctg       336
Ala Lys Lys Ala Lys Thr Asn Glu Phe Ile Ser Ala Tyr Arg Arg Leu
            100                 105                 110 cgc atc aag atc aag ggc atg ggc ctc tac gac gcg tcc atg gtc tac       384
Arg Ile Lys Ile Lys Gly Met Gly Leu Tyr Asp Ala Ser Met Val Tyr
        115                 120                 125 tac gcg tgg aag atc ctc agc acc ttc ggc att tgg atg gcc tcc gtg       432
Tyr Ala Trp Lys Ile Leu Ser Thr Phe Gly Ile Trp Met Ala Ser Val
    130                 135                 140 gcg atc tgc tac cac ttc gac agc tgg ccc atg tac atg ctc gcg gcc       480
Ala Ile Cys Tyr His Phe Asp Ser Trp Pro Met Tyr Met Leu Ala Ala
145                 150                 155                 160 tgc gtc atg ggg ctc ttc tgg cag cag tcg ggc tgg ctc gcg cac gac       528
Cys Val Met Gly Leu Phe Trp Gln Gln Ser Gly Trp Leu Ala His Asp
                165                 170                 175 gtg ctg cac cac caa gtg tgg gac aac cac atg atc ggc aac gtc atg       576
```

| | | |
|---|---|---|
| Val Leu His His Gln Val Trp Asp Asn His Met Ile Gly Asn Val Met<br>180                         185                      190 | | |
| ggc gtc atc atc ggc gac gtc tgg atg ggc ttc agc gtg cag tgg tgg<br>Gly Val Ile Ile Gly Asp Val Trp Met Gly Phe Ser Val Gln Trp Trp<br>    195                    200                    205 | 624 |
| aag aac aag cac aac ttc cac cac gcc gtg ccc aac ctc atc ggc gac<br>Lys Asn Lys His Asn Phe His His Ala Val Pro Asn Leu Ile Gly Asp<br>210                         215                      220 | 672 |
| gaa aag acc aag tac ctc ggc gac ccg gac atc gac acc atg ccc ctg<br>Glu Lys Thr Lys Tyr Leu Gly Asp Pro Asp Ile Asp Thr Met Pro Leu<br>225                       230                    235                    240 | 720 |
| ctg gcc tgg agc aag cac atg gcc tcg cgc gcg tac gag tcg tcg tgg<br>Leu Ala Trp Ser Lys His Met Ala Ser Arg Ala Tyr Glu Ser Ser Trp<br>                245                    250                    255 | 768 |
| ggc ccc ttc ttc gtg agc cac cag gcc gtc atc tac ttc ccg ctg ctg<br>Gly Pro Phe Phe Val Ser His Gln Ala Val Ile Tyr Phe Pro Leu Leu<br>            260                    265                    270 | 816 |
| ctc ttc gcg cgc ttc agc tgg ctg ctg cag agc tac tac tac gtc ttc<br>Leu Phe Ala Arg Phe Ser Trp Leu Leu Gln Ser Tyr Tyr Tyr Val Phe<br>    275                    280                    285 | 864 |
| aag ggc ttc gcc ttc ggc aag tac gac ccc gtg gac ctc ccg aac ggc<br>Lys Gly Phe Ala Phe Gly Lys Tyr Asp Pro Val Asp Leu Pro Asn Gly<br>290                       295                    300 | 912 |
| gag aag ctc ggc ctc tcg ctg cac tac ctc tgg aac gtg ctg ctg ccg<br>Glu Lys Leu Gly Leu Ser Leu His Tyr Leu Trp Asn Val Leu Leu Pro<br>305                       310                    315                    320 | 960 |
| gtg ctc acc ggc atg tcg gtg gcc cag ggc ctg gcc ttc ttc atg ctc<br>Val Leu Thr Gly Met Ser Val Ala Gln Gly Leu Ala Phe Phe Met Leu<br>                325                    330                    335 | 1008 |
| tcg cag atg tcg tgc ggc gcc ttc ctg gcc gcc gtc ttc agc gtc ggc<br>Ser Gln Met Ser Cys Gly Ala Phe Leu Ala Ala Val Phe Ser Val Gly<br>            340                    345                    350 | 1056 |
| cac aac ggc atg tcg gtg tac gag cgc gac cag aag ccc gac ttc tgg<br>His Asn Gly Met Ser Val Tyr Glu Arg Asp Gln Lys Pro Asp Phe Trp<br>    355                    360                    365 | 1104 |
| cag ctg cag gtc acc acc acg cgc aac atc acg ccg ggc ttc ttc atg<br>Gln Leu Gln Val Thr Thr Thr Arg Asn Ile Thr Pro Gly Phe Phe Met<br>370                       375                    380 | 1152 |
| gac tgg ttc tgc ggc ggc ctc aac tac cag atc gag cac cac ttg ttc<br>Asp Trp Phe Cys Gly Gly Leu Asn Tyr Gln Ile Glu His His Leu Phe<br>385                       390                    395                    400 | 1200 |
| ccc atg atg ccg cgc cac aac ctg cag aag gtc aac ccg ctc gtc aag<br>Pro Met Met Pro Arg His Asn Leu Gln Lys Val Asn Pro Leu Val Lys<br>                405                    410                    415 | 1248 |
| tcg ctc tgc aag cag tac gac gtc aag ttc cac gag acg ggc ttc tac<br>Ser Leu Cys Lys Gln Tyr Asp Val Lys Phe His Glu Thr Gly Phe Tyr<br>            420                    425                    430 | 1296 |
| cgc gga ctc gtc gag gtc gtg gac gag ctg gcc gac atc agc aag gag<br>Arg Gly Leu Val Glu Val Val Asp Glu Leu Ala Asp Ile Ser Lys Glu<br>    435                    440                    445 | 1344 |
| ttc ctc ctc gag ttc ccg gcc atg taa<br>Phe Leu Leu Glu Phe Pro Ala Met<br>    450                    455 | 1371 |

<210> SEQ ID NO 2
<211> LENGTH: 456
<212> TYPE: PRT
<213> ORGANISM: Phytophthora sojae

<400> SEQUENCE: 2

Met Val Asp Gly Pro Lys Thr Lys Arg Leu Ile Ser Trp Gln Glu Ile

```
              1               5              10              15
Gln Gln His Ser Thr Tyr Ala Asn Ala Trp Ile Val Ile His His Lys
                    20              25              30
Val Tyr Asp Ile Ser Lys Trp Asp Ser His Pro Gly Gly Met Val Met
                35              40              45
Leu Ser Gln Ala Gly Glu Asp Ala Thr Asp Ile Phe Thr Val Cys His
    50              55              60
Pro Thr Ser Ser Trp Lys Leu Leu Glu Gln Phe Tyr Ile Gly Asp Val
65                      70              75              80
Asp Glu Ser Thr Ala Pro Gly Thr Thr Gly Leu Ser Glu Glu Gln Lys
                85              90              95
Ala Lys Lys Ala Lys Thr Asn Glu Phe Ile Ser Ala Tyr Arg Arg Leu
            100             105             110
Arg Ile Lys Ile Lys Gly Met Gly Leu Tyr Asp Ala Ser Met Val Tyr
        115             120             125
Tyr Ala Trp Lys Ile Leu Ser Thr Phe Gly Ile Trp Met Ala Ser Val
    130             135             140
Ala Ile Cys Tyr His Phe Asp Ser Trp Pro Met Tyr Met Leu Ala Ala
145             150             155             160
Cys Val Met Gly Leu Phe Trp Gln Gln Ser Gly Trp Leu Ala His Asp
                165             170             175
Val Leu His His Gln Val Trp Asp Asn His Met Ile Gly Asn Val Met
            180             185             190
Gly Val Ile Ile Gly Asp Val Trp Met Gly Phe Ser Val Gln Trp Trp
        195             200             205
Lys Asn Lys His Asn Phe His His Ala Val Pro Asn Leu Ile Gly Asp
    210             215             220
Glu Lys Thr Lys Tyr Leu Gly Asp Pro Asp Ile Asp Thr Met Pro Leu
225             230             235             240
Leu Ala Trp Ser Lys His Met Ala Ser Arg Ala Tyr Glu Ser Ser Trp
                245             250             255
Gly Pro Phe Phe Val Ser His Gln Ala Val Ile Tyr Phe Pro Leu Leu
            260             265             270
Leu Phe Ala Arg Phe Ser Trp Leu Leu Gln Ser Tyr Tyr Tyr Val Phe
        275             280             285
Lys Gly Phe Ala Phe Gly Lys Tyr Asp Pro Val Asp Leu Pro Asn Gly
    290             295             300
Glu Lys Leu Gly Leu Ser Leu His Tyr Leu Trp Asn Val Leu Leu Pro
305             310             315             320
Val Leu Thr Gly Met Ser Val Ala Gln Gly Leu Ala Phe Phe Met Leu
                325             330             335
Ser Gln Met Ser Cys Gly Ala Phe Leu Ala Ala Val Phe Ser Val Gly
            340             345             350
His Asn Gly Met Ser Val Tyr Glu Arg Asp Gln Lys Pro Asp Phe Trp
        355             360             365
Gln Leu Gln Val Thr Thr Thr Arg Asn Ile Thr Pro Gly Phe Phe Met
    370             375             380
Asp Trp Phe Cys Gly Gly Leu Asn Tyr Gln Ile Glu His His Leu Phe
385             390             395             400
Pro Met Met Pro Arg His Asn Leu Gln Lys Val Asn Pro Leu Val Lys
                405             410             415
Ser Leu Cys Lys Gln Tyr Asp Val Lys Phe His Glu Thr Gly Phe Tyr
            420             425             430
```

-continued

```
                             Arg Gly Leu Val Glu Val Val Asp Glu Leu Ala Asp Ile Ser Lys Glu
                                     435                 440                 445

Phe Leu Leu Glu Phe Pro Ala Met
                                 450                 455

<210> SEQ ID NO 3
<211> LENGTH: 915
<212> TYPE: DNA
<213> ORGANISM: Phytophthora sojae
<220> FEATURE:
<221> NAME/KEY: CDS
<222> LOCATION: (1)..(915)
<223> OTHER INFORMATION: Delta-6 elongase

<400> SEQUENCE: 3 atg gag acg acc ttc gcg cgc acg ccc aag ctg cac gac gag gtg ccg        48
Met Glu Thr Thr Phe Ala Arg Thr Pro Lys Leu His Asp Glu Val Pro
1               5                   10                  15 gcg ctg cgc tgg atg tac ccg tcc cag tac gag cgc gac tgg cta cac        96
Ala Leu Arg Trp Met Tyr Pro Ser Gln Tyr Glu Arg Asp Trp Leu His
                20                  25                  30 tat gcc tgg aac cga cgg ccc act aac ttc tct cgt atc ttc cgc cag       144
Tyr Ala Trp Asn Arg Arg Pro Thr Asn Phe Ser Arg Ile Phe Arg Gln
            35                  40                  45 gcc atc tcg tgg gag ccg ggc ttc tgc atg gag tcg ctg ccc atg gcc       192
Ala Ile Ser Trp Glu Pro Gly Phe Cys Met Glu Ser Leu Pro Met Ala
        50                  55                  60 gtg gcg ctg tgc gcc gcc tac tgc gtg ctg tgc ttc gcc ggc cgc cgc       240
Val Ala Leu Cys Ala Ala Tyr Cys Val Leu Cys Phe Ala Gly Arg Arg
65                  70                  75                  80 gtc atg cgc gac ctc aag ccc ttc aac ctc aaa gtc ccg ctc gcg ctc       288
Val Met Arg Asp Leu Lys Pro Phe Asn Leu Lys Val Pro Leu Ala Leu
                85                  90                  95 tgg aac ctg gcg ctg gcc acg ttc agc gcc atc ggc gcc tcc agg acg       336
Trp Asn Leu Ala Leu Ala Thr Phe Ser Ala Ile Gly Ala Ser Arg Thr
                100                 105                 110 gtg ccc ttc ctc atc aac acc gtc tac cgc cgc ggc gtg tac cac tcg       384
Val Pro Phe Leu Ile Asn Thr Val Tyr Arg Arg Gly Val Tyr His Ser
            115                 120                 125 gtg tgc gcg ccg ccc acg ccg cac tac ggc cac ggc ccc gtg gcg ctc       432
Val Cys Ala Pro Pro Thr Pro His Tyr Gly His Gly Pro Val Ala Leu
        130                 135                 140 tgg gtc atg ctc ttc atc ttc tcc aag gtg ccg gag ctc gtg gac acg       480
Trp Val Met Leu Phe Ile Phe Ser Lys Val Pro Glu Leu Val Asp Thr
145                 150                 155                 160 gcc ttc atc gtg ctg cgc aag aag ccg ctc atc ttc ctg cac tgg tac       528
Ala Phe Ile Val Leu Arg Lys Lys Pro Leu Ile Phe Leu His Trp Tyr
                165                 170                 175 cac cac atc acc gtg ctg ctc ttc tgc tgg cac gcg ttc gcc acg ctc       576
His His Ile Thr Val Leu Leu Phe Cys Trp His Ala Phe Ala Thr Leu
                180                 185                 190 tcg gct agc ggc ctg tac ttc gtg gcc atg aac tac tcg gtg cac gcc       624
Ser Ala Ser Gly Leu Tyr Phe Val Ala Met Asn Tyr Ser Val His Ala
            195                 200                 205 atc atg tac ttc tac tac ttc ctg acg gcg tgc ggc tac cga ccg cgc       672
Ile Met Tyr Phe Tyr Tyr Phe Leu Thr Ala Cys Gly Tyr Arg Pro Arg
        210                 215                 220 tgg gct cgc ctc gtg acg atc ttc cag ctg agc cag atg ggc gtg ggc       720
Trp Ala Arg Leu Val Thr Ile Phe Gln Leu Ser Gln Met Gly Val Gly
225                 230                 235                 240 gtc gcc gtg tgc ggc ctc aac gtg tac tac atg aag cag ggc gcc acg       768
Val Ala Val Cys Gly Leu Asn Val Tyr Tyr Met Lys Gln Gly Ala Thr
```

-continued

```
                    245                 250                 255
tgc agc gtg gac ccg gac aac ctc aag tgg ggc atc atc atg tac tcg      816
Cys Ser Val Asp Pro Asp Asn Leu Lys Trp Gly Ile Ile Met Tyr Ser
        260                 265                 270 agc tac ttt gcg ctc ttc ctc aag ttc ttc atc gag cgc tac ctg ctg      864
Ser Tyr Phe Ala Leu Phe Leu Lys Phe Phe Ile Glu Arg Tyr Leu Leu
    275                 280                 285 cgc agc gcc aag aag ccc gcc gcc gct gcg gtc gcc aag aag acg cag      912
Arg Ser Ala Lys Lys Pro Ala Ala Ala Val Ala Lys Lys Thr Gln
290                 295                 300 taa                                                                   915

<210> SEQ ID NO 4
<211> LENGTH: 304
<212> TYPE: PRT
<213> ORGANISM: Phytophthora sojae

<400> SEQUENCE: 4

Met Glu Thr Thr Phe Ala Arg Thr Pro Lys Leu His Asp Glu Val Pro
1               5                   10                  15

Ala Leu Arg Trp Met Tyr Pro Ser Gln Tyr Glu Arg Asp Trp Leu His
            20                  25                  30

Tyr Ala Trp Asn Arg Arg Pro Thr Asn Phe Ser Arg Ile Phe Arg Gln
        35                  40                  45

Ala Ile Ser Trp Glu Pro Gly Phe Cys Met Glu Ser Leu Pro Met Ala
    50                  55                  60

Val Ala Leu Cys Ala Ala Tyr Cys Val Leu Cys Phe Ala Gly Arg Arg
65                  70                  75                  80

Val Met Arg Asp Leu Lys Pro Phe Asn Leu Lys Val Pro Leu Ala Leu
                85                  90                  95

Trp Asn Leu Ala Leu Ala Thr Phe Ser Ala Ile Gly Ala Ser Arg Thr
            100                 105                 110

Val Pro Phe Leu Ile Asn Thr Val Tyr Arg Arg Gly Val Tyr His Ser
        115                 120                 125

Val Cys Ala Pro Pro Thr Pro His Tyr Gly His Gly Pro Val Ala Leu
    130                 135                 140

Trp Val Met Leu Phe Ile Phe Ser Lys Val Pro Glu Leu Val Asp Thr
145                 150                 155                 160

Ala Phe Ile Val Leu Arg Lys Lys Pro Leu Ile Phe Leu His Trp Tyr
                165                 170                 175

His His Ile Thr Val Leu Leu Phe Cys Trp His Ala Phe Ala Thr Leu
            180                 185                 190

Ser Ala Ser Gly Leu Tyr Phe Val Ala Met Asn Tyr Ser Val His Ala
        195                 200                 205

Ile Met Tyr Phe Tyr Tyr Phe Leu Thr Ala Cys Gly Tyr Arg Pro Arg
    210                 215                 220

Trp Ala Arg Leu Val Thr Ile Phe Gln Leu Ser Gln Met Gly Val Gly
225                 230                 235                 240

Val Ala Val Cys Gly Leu Asn Val Tyr Tyr Met Lys Gln Gly Ala Thr
                245                 250                 255

Cys Ser Val Asp Pro Asp Asn Leu Lys Trp Gly Ile Ile Met Tyr Ser
            260                 265                 270

Ser Tyr Phe Ala Leu Phe Leu Lys Phe Phe Ile Glu Arg Tyr Leu Leu
        275                 280                 285

Arg Ser Ala Lys Lys Pro Ala Ala Ala Val Ala Lys Lys Thr Gln
    290                 295                 300
```

<210> SEQ ID NO 5
<211> LENGTH: 837
<212> TYPE: DNA
<213> ORGANISM: Phytophthora sojae
<220> FEATURE:
<221> NAME/KEY: CDS
<222> LOCATION: (1)..(837)
<223> OTHER INFORMATION: Delta-6 elongase

<400> SEQUENCE: 5

| | | | | | | | | | | | | | | | | |
|---|---|---|---|---|---|---|---|---|---|---|---|---|---|---|---|---|
| atg | gcg | tcg | gag | ctg | ctg | cag | agt | tac | tac | gag | tgg | gcg | aat | gcc | acc | 48 |
| Met | Ala | Ser | Glu | Leu | Leu | Gln | Ser | Tyr | Tyr | Glu | Trp | Ala | Asn | Ala | Thr | |
| 1 | | | | 5 | | | | | 10 | | | | | 15 | | |
| gag | atc | aag | gtg | ctc | gac | tgg | gtg | gac | ccc | gaa | ggc | ggc | tgg | aag | gtc | 96 |
| Glu | Ile | Lys | Val | Leu | Asp | Trp | Val | Asp | Pro | Glu | Gly | Gly | Trp | Lys | Val | |
| | | | 20 | | | | | 25 | | | | | 30 | | | |
| cac | ccc | atg | gcg | gac | tac | ccg | ctc | gcc | aac | ttc | gcc | agc | gtg | ttc | gcc | 144 |
| His | Pro | Met | Ala | Asp | Tyr | Pro | Leu | Ala | Asn | Phe | Ala | Ser | Val | Phe | Ala | |
| | | 35 | | | | | 40 | | | | | 45 | | | | |
| atc | tgc | gtc | ggc | tac | ctg | ctc | ttc | gtc | atc | ttc | ggc | acg | gcc | ctg | atg | 192 |
| Ile | Cys | Val | Gly | Tyr | Leu | Leu | Phe | Val | Ile | Phe | Gly | Thr | Ala | Leu | Met | |
| | 50 | | | | | 55 | | | | | 60 | | | | | |
| aag | atg | ggc | atc | ccc | gcc | atc | aag | acg | agc | ccc | atc | cag | ttc | atc | tac | 240 |
| Lys | Met | Gly | Ile | Pro | Ala | Ile | Lys | Thr | Ser | Pro | Ile | Gln | Phe | Ile | Tyr | |
| 65 | | | | | 70 | | | | | 75 | | | | | 80 | |
| aac | ccc | atc | cag | gtc | atc | gcc | tgc | tcc | tac | atg | ttc | gtg | gag | acc | gcc | 288 |
| Asn | Pro | Ile | Gln | Val | Ile | Ala | Cys | Ser | Tyr | Met | Phe | Val | Glu | Thr | Ala | |
| | | | | 85 | | | | | 90 | | | | | 95 | | |
| atc | cag | gcc | tac | cgc | aat | ggg | tac | tcg | cca | gct | ccg | tgc | aac | gcc | ttc | 336 |
| Ile | Gln | Ala | Tyr | Arg | Asn | Gly | Tyr | Ser | Pro | Ala | Pro | Cys | Asn | Ala | Phe | |
| | | | 100 | | | | | 105 | | | | | 110 | | | |
| aag | acg | gac | gcg | ccc | gtc | atg | ggc | aac | gtg | ctc | tac | ctg | ttc | tac | ctg | 384 |
| Lys | Thr | Asp | Ala | Pro | Val | Met | Gly | Asn | Val | Leu | Tyr | Leu | Phe | Tyr | Leu | |
| | | 115 | | | | | 120 | | | | | 125 | | | | |
| tcc | aag | atg | ctg | gac | ctg | tgc | gac | acc | ttc | ttc | atc | gtc | gtg | ggc | aag | 432 |
| Ser | Lys | Met | Leu | Asp | Leu | Cys | Asp | Thr | Phe | Phe | Ile | Val | Val | Gly | Lys | |
| | 130 | | | | | 135 | | | | | 140 | | | | | |
| aaa | tgg | cgc | cag | ctc | tcg | ttc | ctg | cac | gtg | tac | cac | cac | ctc | tcg | gtg | 480 |
| Lys | Trp | Arg | Gln | Leu | Ser | Phe | Leu | His | Val | Tyr | His | His | Leu | Ser | Val | |
| 145 | | | | | 150 | | | | | 155 | | | | | 160 | |
| ctg | ctc | atg | tac | tac | atc | gtc | ttc | cgc | gtg | gcg | cag | gac | ggc | gac | tcg | 528 |
| Leu | Leu | Met | Tyr | Tyr | Ile | Val | Phe | Arg | Val | Ala | Gln | Asp | Gly | Asp | Ser | |
| | | | | 165 | | | | | 170 | | | | | 175 | | |
| tac | gcg | tcc | gtc | gtg | ctc | aac | ggc | ttc | gtg | cac | acc | atc | atg | tac | acg | 576 |
| Tyr | Ala | Ser | Val | Val | Leu | Asn | Gly | Phe | Val | His | Thr | Ile | Met | Tyr | Thr | |
| | | | 180 | | | | | 185 | | | | | 190 | | | |
| tac | tac | ttc | gtg | agc | gcg | cac | acg | cgg | gac | att | tgg | tgg | aag | cgc | tac | 624 |
| Tyr | Tyr | Phe | Val | Ser | Ala | His | Thr | Arg | Asp | Ile | Trp | Trp | Lys | Arg | Tyr | |
| | | 195 | | | | | 200 | | | | | 205 | | | | |
| ctg | acg | ctc | att | cag | ttg | gtg | cag | ttc | gtg | acc | atg | aac | gtg | cag | ggc | 672 |
| Leu | Thr | Leu | Ile | Gln | Leu | Val | Gln | Phe | Val | Thr | Met | Asn | Val | Gln | Gly | |
| | 210 | | | | | 215 | | | | | 220 | | | | | |
| tac | ctc | atg | tac | tcg | cgc | cag | tgc | cca | ggc | atg | ccg | ccc | aag | atc | ccg | 720 |
| Tyr | Leu | Met | Tyr | Ser | Arg | Gln | Cys | Pro | Gly | Met | Pro | Pro | Lys | Ile | Pro | |
| 225 | | | | | 230 | | | | | 235 | | | | | 240 | |
| ctc | atc | tat | ctg | gcc | tac | gtg | cag | tcg | ctc | ttc | tgg | ctg | ttc | gtc | aac | 768 |
| Leu | Ile | Tyr | Leu | Ala | Tyr | Val | Gln | Ser | Leu | Phe | Trp | Leu | Phe | Val | Asn | |
| | | | | 245 | | | | | 250 | | | | | 255 | | |
| ttc | tac | gtg | cgc | tcg | tac | gtg | ctc | gcc | ccc | aag | aag | acc | aag | gcg | tcc | 816 |
| Phe | Tyr | Val | Arg | Ser | Tyr | Val | Leu | Ala | Pro | Lys | Lys | Thr | Lys | Ala | Ser | |
| | | | 260 | | | | | 265 | | | | | 270 | | | |

```
ccg gcc aag aag aac ctc taa                                          837
Pro Ala Lys Lys Asn Leu
        275
```

<210> SEQ ID NO 6
<211> LENGTH: 278
<212> TYPE: PRT
<213> ORGANISM: Phytophthora sojae

<400> SEQUENCE: 6

```
Met Ala Ser Glu Leu Leu Gln Ser Tyr Tyr Glu Trp Ala Asn Ala Thr
1               5                   10                  15

Glu Ile Lys Val Leu Asp Trp Val Asp Pro Glu Gly Gly Trp Lys Val
            20                  25                  30

His Pro Met Ala Asp Tyr Pro Leu Ala Asn Phe Ala Ser Val Phe Ala
        35                  40                  45

Ile Cys Val Gly Tyr Leu Leu Phe Val Phe Gly Thr Ala Leu Met
    50                  55                  60

Lys Met Gly Ile Pro Ala Ile Lys Thr Ser Pro Ile Gln Phe Ile Tyr
65                  70                  75                  80

Asn Pro Ile Gln Val Ile Ala Cys Ser Tyr Met Phe Val Glu Thr Ala
                85                  90                  95

Ile Gln Ala Tyr Arg Asn Gly Tyr Ser Pro Ala Pro Cys Asn Ala Phe
            100                 105                 110

Lys Thr Asp Ala Pro Val Met Gly Asn Val Leu Tyr Leu Phe Tyr Leu
        115                 120                 125

Ser Lys Met Leu Asp Leu Cys Asp Thr Phe Phe Ile Val Val Gly Lys
    130                 135                 140

Lys Trp Arg Gln Leu Ser Phe Leu His Val Tyr His His Leu Ser Val
145                 150                 155                 160

Leu Leu Met Tyr Tyr Ile Val Phe Arg Val Ala Gln Asp Gly Asp Ser
                165                 170                 175

Tyr Ala Ser Val Val Leu Asn Gly Phe Val His Thr Ile Met Tyr Thr
            180                 185                 190

Tyr Tyr Phe Val Ser Ala His Thr Arg Asp Ile Trp Trp Lys Arg Tyr
        195                 200                 205

Leu Thr Leu Ile Gln Leu Val Gln Phe Val Thr Met Asn Val Gln Gly
    210                 215                 220

Tyr Leu Met Tyr Ser Arg Gln Cys Pro Gly Met Pro Pro Lys Ile Pro
225                 230                 235                 240

Leu Ile Tyr Leu Ala Tyr Val Gln Ser Leu Phe Trp Leu Phe Val Asn
                245                 250                 255

Phe Tyr Val Arg Ser Tyr Val Leu Ala Pro Lys Lys Thr Lys Ala Ser
            260                 265                 270

Pro Ala Lys Lys Asn Leu
        275
```

<210> SEQ ID NO 7
<211> LENGTH: 837
<212> TYPE: DNA
<213> ORGANISM: Phytophthora sojae
<220> FEATURE:
<221> NAME/KEY: CDS
<222> LOCATION: (1)..(837)
<223> OTHER INFORMATION: Delta-6 elongase

<400> SEQUENCE: 7

```
atg tcg gcc gac ctg ctg cag agc tac tac gac tgg acc aac gcc acc        48
```

```
Met Ser Ala Asp Leu Leu Gln Ser Tyr Tyr Asp Trp Thr Asn Ala Thr
1               5                   10                  15 gag gcc aag ctg ctc gac tgg gtg gac ccc gaa ggc ggc tgg aag gtc        96
Glu Ala Lys Leu Leu Asp Trp Val Asp Pro Glu Gly Gly Trp Lys Val
            20                  25                  30 cac ccc atg gcc gac tac ccg ctc gcc aac ttc gcc agc gtc tac gcc       144
His Pro Met Ala Asp Tyr Pro Leu Ala Asn Phe Ala Ser Val Tyr Ala
                35                  40                  45 atc tgc gtc ggc tac ctg ctc ttc gtc atc ttc ggc acg gcc ctg atg       192
Ile Cys Val Gly Tyr Leu Leu Phe Val Ile Phe Gly Thr Ala Leu Met
        50                  55                  60 aag atg ggc atc ccc gcc atc aag acg agc ccc atc cag ttc atc tac       240
Lys Met Gly Ile Pro Ala Ile Lys Thr Ser Pro Ile Gln Phe Ile Tyr
65              70                  75                  80 aac ccc atc cag gtc atc gcc tgc tcc tac atg tgc gtg gag gcc gcc       288
Asn Pro Ile Gln Val Ile Ala Cys Ser Tyr Met Cys Val Glu Ala Ala
                85                  90                  95 atc cag gcc tac cgc aac ggc tac agc gcg gcg ccc tgc aac gcc ttc       336
Ile Gln Ala Tyr Arg Asn Gly Tyr Ser Ala Ala Pro Cys Asn Ala Phe
            100                 105                 110 aag gcg gac gcg ccc gtc atg ggc aac gtg ctc tac ctg ttc tac ctg       384
Lys Ala Asp Ala Pro Val Met Gly Asn Val Leu Tyr Leu Phe Tyr Leu
        115                 120                 125 tcc aag atg ctg gac ctg tgc gac acg gtc ttc atc atc ctc ggc aag       432
Ser Lys Met Leu Asp Leu Cys Asp Thr Val Phe Ile Ile Leu Gly Lys
    130                 135                 140 aag tgg aag cag ctc tcc atc ctg cac gtg tac cac cac ctg acc gtg       480
Lys Trp Lys Gln Leu Ser Ile Leu His Val Tyr His His Leu Thr Val
145                 150                 155                 160 ctc ttc gtc tac tac gtg acg ttc cgc gcc gcc cag gac ggc gac tcg       528
Leu Phe Val Tyr Tyr Val Thr Phe Arg Ala Ala Gln Asp Gly Asp Ser
                165                 170                 175 tac gcc acc atc gtg ctc aac ggc ttc gtg cac acc atc atg tac acg       576
Tyr Ala Thr Ile Val Leu Asn Gly Phe Val His Thr Ile Met Tyr Thr
            180                 185                 190 tac tac ttc gtg agc gcg cac acg cgc aac att tgg tgg aag aag tac       624
Tyr Tyr Phe Val Ser Ala His Thr Arg Asn Ile Trp Trp Lys Lys Tyr
        195                 200                 205 ctc acg cgc atc cag ctc atc cag ttc gtg acc atg aac gtg cag ggc       672
Leu Thr Arg Ile Gln Leu Ile Gln Phe Val Thr Met Asn Val Gln Gly
    210                 215                 220 tac ctg acg tac tcg cgc cag tgc ccg ggc atg ccc ccc aag gtg ccg       720
Tyr Leu Thr Tyr Ser Arg Gln Cys Pro Gly Met Pro Pro Lys Val Pro
225                 230                 235                 240 ctc atg tac ctc gtg tac gtg cag tcg ctc ttc tgg ctc ttc atg aac       768
Leu Met Tyr Leu Val Tyr Val Gln Ser Leu Phe Trp Leu Phe Met Asn
                245                 250                 255 ttc tac atc cgc gcg tac gtc ttc ggc ccc aag aag ccc gcc gtc gag       816
Phe Tyr Ile Arg Ala Tyr Val Phe Gly Pro Lys Lys Pro Ala Val Glu
            260                 265                 270 gac gcc aag aag aag ctc taa                                           837
Asp Ala Lys Lys Lys Leu
        275

<210> SEQ ID NO 8
<211> LENGTH: 278
<212> TYPE: PRT
<213> ORGANISM: Phytophthora sojae

<400> SEQUENCE: 8

Met Ser Ala Asp Leu Leu Gln Ser Tyr Tyr Asp Trp Thr Asn Ala Thr
```

```
                1               5              10              15
            Glu Ala Lys Leu Leu Asp Trp Val Asp Pro Glu Gly Gly Trp Lys Val
                            20                  25                  30

His Pro Met Ala Asp Tyr Pro Leu Ala Asn Phe Ala Ser Val Tyr Ala
                        35                  40                  45

Ile Cys Val Gly Tyr Leu Leu Phe Val Ile Phe Gly Thr Ala Leu Met
             50                  55                  60

Lys Met Gly Ile Pro Ala Ile Lys Thr Ser Pro Ile Gln Phe Ile Tyr
             65                  70                  75                  80

Asn Pro Ile Gln Val Ile Ala Cys Ser Tyr Met Cys Val Glu Ala Ala
                            85                  90                  95

Ile Gln Ala Tyr Arg Asn Gly Tyr Ser Ala Ala Pro Cys Asn Ala Phe
                        100                 105                 110

Lys Ala Asp Ala Pro Val Met Gly Asn Val Leu Tyr Leu Phe Tyr Leu
                    115                 120                 125

Ser Lys Met Leu Asp Leu Cys Asp Thr Val Phe Ile Ile Leu Gly Lys
                130                 135                 140

Lys Trp Lys Gln Leu Ser Ile Leu His Val Tyr His Leu Thr Val
            145                 150                 155                 160

Leu Phe Val Tyr Tyr Val Thr Phe Arg Ala Ala Gln Asp Gly Asp Ser
                            165                 170                 175

Tyr Ala Thr Ile Val Leu Asn Gly Phe Val His Thr Ile Met Tyr Thr
                        180                 185                 190

Tyr Tyr Phe Val Ser Ala His Thr Arg Asn Ile Trp Trp Lys Lys Tyr
                    195                 200                 205

Leu Thr Arg Ile Gln Leu Ile Gln Phe Val Thr Met Asn Val Gln Gly
                210                 215                 220

Tyr Leu Thr Tyr Ser Arg Gln Cys Pro Gly Met Pro Pro Lys Val Pro
            225                 230                 235                 240

Leu Met Tyr Leu Val Tyr Val Gln Ser Leu Phe Trp Leu Phe Met Asn
                            245                 250                 255

Phe Tyr Ile Arg Ala Tyr Val Phe Gly Pro Lys Lys Pro Ala Val Glu
                        260                 265                 270

Asp Ala Lys Lys Lys Leu
                    275

<210> SEQ ID NO 9
<211> LENGTH: 1497
<212> TYPE: DNA
<213> ORGANISM: Phytophthora sojae
<220> FEATURE:
<221> NAME/KEY: CDS
<222> LOCATION: (1)..(1497)
<223> OTHER INFORMATION: Delta-5 desaturase

<400> SEQUENCE: 9 atg gcc ccc atc gag acc gac aag gcc gtg agt gcc aac gag ggc ctg        48
Met Ala Pro Ile Glu Thr Asp Lys Ala Val Ser Ala Asn Glu Gly Leu
 1               5                  10                  15 cac cag cgc aag ggc gcc gcc tcg gcc gac aag gac gcc acc tac acg        96
His Gln Arg Lys Gly Ala Ala Ser Ala Asp Lys Asp Ala Thr Tyr Thr
                20                  25                  30 tgg cag gac gtg gcc aag cac aac acg gcc aag agc gcc tgg gtc atc       144
Trp Gln Asp Val Ala Lys His Asn Thr Ala Lys Ser Ala Trp Val Ile
            35                  40                  45 atc cgc ggc gtc gtc tac gac gtc act gat act ctg aaa aca ccc caa       192
Ile Arg Gly Val Val Tyr Asp Val Thr Asp Thr Leu Lys Thr Pro Gln
        50                  55                  60
```

| | | |
|---|---|---|
| agt aaa atc cta acc tgt tcc tgc gtg atg gca cca cca gaa tgg gcg<br>Ser Lys Ile Leu Thr Cys Ser Cys Val Met Ala Pro Pro Glu Trp Ala<br>65                    70                   75                 80 | 240 |
| gac cgt cac cct ggc ggc cgc gag ctc gtg ctg ctg cac gcc gga cgc<br>Asp Arg His Pro Gly Gly Arg Glu Leu Val Leu Leu His Ala Gly Arg<br>                   85                   90                   95 | 288 |
| gag tgc acg gac acg ttc gac tcg tac cac ccc ttc tcc aac cgc gcc<br>Glu Cys Thr Asp Thr Phe Asp Ser Tyr His Pro Phe Ser Asn Arg Ala<br>               100                    105                110 | 336 |
| gac aag atc ctg gcc aag tac gcc gtt ggt aag ctc gtg ggc ggc tcc<br>Asp Lys Ile Leu Ala Lys Tyr Ala Val Gly Lys Leu Val Gly Gly Ser<br>       115                  120                  125 | 384 |
| gag ttc ccc cag tac aag ccc gac acg ggc ttc tac aag gag tgc tgc<br>Glu Phe Pro Gln Tyr Lys Pro Asp Thr Gly Phe Tyr Lys Glu Cys Cys<br>130                  135                   140 | 432 |
| gag cgc gtg cac cag tac ttt aag gac aac aac ctg gac ccg cgc agc<br>Glu Arg Val His Gln Tyr Phe Lys Asp Asn Asn Leu Asp Pro Arg Ser<br>145                  150                   155             160 | 480 |
| ccg tac tcg ggc atg tgg cgc atg atg atc gtc gct gcg ctc ggc gcc<br>Pro Tyr Ser Gly Met Trp Arg Met Met Ile Val Ala Ala Leu Gly Ala<br>                  165                  170               175 | 528 |
| atc tcg tac ctg ggc atg aac cag ctg ctc tcg gac aac atc tac gcg<br>Ile Ser Tyr Leu Gly Met Asn Gln Leu Leu Ser Asp Asn Ile Tyr Ala<br>               180                    185                190 | 576 |
| cac tac gcg tgg ggc gcc ctc ttc ggc gtg tgc cag gcg ctg ccg ctg<br>His Tyr Ala Trp Gly Ala Leu Phe Gly Val Cys Gln Ala Leu Pro Leu<br>     195                  200                  205 | 624 |
| ctc cac gtg atg cac gac gcg tcg cac gcc gcc atc acc agc agc ccc<br>Leu His Val Met His Asp Ala Ser His Ala Ala Ile Thr Ser Ser Pro<br>210                  215                   220 | 672 |
| acg ggc tgg agg ctc att ggc cgc ttc gcg atg gac tgg gtg gcc ggc<br>Thr Gly Trp Arg Leu Ile Gly Arg Phe Ala Met Asp Trp Val Ala Gly<br>225                  230                   235             240 | 720 |
| gcc aac atg gta tcg tgg ctc aac cag cac gtt gtg ggc cac cac atc<br>Ala Asn Met Val Ser Trp Leu Asn Gln His Val Val Gly His His Ile<br>                  245                  250              255 | 768 |
| tac aca aac gtg gcc ggc gct gac ccc gac ctt ccc gtg gac ttc aag<br>Tyr Thr Asn Val Ala Gly Ala Asp Pro Asp Leu Pro Val Asp Phe Lys<br>               260                    265                270 | 816 |
| agc gac gtg cgc cgc att gtg tac cgt cag gtg ctg ctg ccc atc tac<br>Ser Asp Val Arg Arg Ile Val Tyr Arg Gln Val Leu Leu Pro Ile Tyr<br>       275                  280                  285 | 864 |
| aag ttc cag cac ttg tac ctg ccg ccg ctg tac ggc gtg ctc ggc ctc<br>Lys Phe Gln His Leu Tyr Leu Pro Pro Leu Tyr Gly Val Leu Gly Leu<br>290                  295                   300 | 912 |
| aag ttc cgc gtg cag gac att ttc gag acg ttc atc tcg ctc acg aac<br>Lys Phe Arg Val Gln Asp Ile Phe Glu Thr Phe Ile Ser Leu Thr Asn<br>305                  310                   315             320 | 960 |
| ggt ccg ctg cgc gtg aac ccg cac tca gtc ggc gac tgg gtc gag atg<br>Gly Pro Leu Arg Val Asn Pro His Ser Val Gly Asp Trp Val Glu Met<br>               325                    330                335 | 1008 |
| atc ctg tcc aag gcc ttc tgg gcg ttc tac cgc atc tac atc ccg ctg<br>Ile Leu Ser Lys Ala Phe Trp Ala Phe Tyr Arg Ile Tyr Ile Pro Leu<br>             340                    345                350 | 1056 |
| gtc gtg ctg cag gtg gac tcg tcc cgc ttc tgg ggc gtc ttc ttc ctg<br>Val Val Leu Gln Val Asp Ser Ser Arg Phe Trp Gly Val Phe Phe Leu<br>     355                  360                  365 | 1104 |
| gcc gag ttc atg acg ggc tgg tac ctg gcc ttc aac ttc cag gtg agc<br>Ala Glu Phe Met Thr Gly Trp Tyr Leu Ala Phe Asn Phe Gln Val Ser<br>370                  375                   380 | 1152 |

```
cac gtc tcc acg gcc tgc gaa tac ccg ggc ggt gac gag gag gtg acg      1200
His Val Ser Thr Ala Cys Glu Tyr Pro Gly Gly Asp Glu Glu Val Thr
385                 390                 395                 400 gcc atc gag gac gag tgg gct gtc tcg cag atc aag tcg tcg gtg gac      1248
Ala Ile Glu Asp Glu Trp Ala Val Ser Gln Ile Lys Ser Ser Val Asp
            405                 410                 415 tac ggc cac ggc tcg ttc ctc acg gcg ttc ctc acg ggc gcg ctg aac      1296
Tyr Gly His Gly Ser Phe Leu Thr Ala Phe Leu Thr Gly Ala Leu Asn
        420                 425                 430 tac cag gtg acc cac cac ctc ttc ccg ggc gtc tcg cag tac cac tac      1344
Tyr Gln Val Thr His His Leu Phe Pro Gly Val Ser Gln Tyr His Tyr
    435                 440                 445 ccg gcc atc gcg ccg atc atc atc gac gtg tgc aac aaa tac aag atc      1392
Pro Ala Ile Ala Pro Ile Ile Ile Asp Val Cys Asn Lys Tyr Lys Ile
450                 455                 460 aag tac acg gtg ctc ccc acg ttc acg gag gcg ctg gcc ggc cac ttc      1440
Lys Tyr Thr Val Leu Pro Thr Phe Thr Glu Ala Leu Ala Gly His Phe
465                 470                 475                 480 gac cac ctc gtc gtc atg ggc aag atg ggc aag ccc gtg tcc gtc cac      1488
Asp His Leu Val Val Met Gly Lys Met Gly Lys Pro Val Ser Val His
            485                 490                 495 atg ggc taa                                                          1497
Met Gly
```

<210> SEQ ID NO 10
<211> LENGTH: 498
<212> TYPE: PRT
<213> ORGANISM: Phytophthora sojae

<400> SEQUENCE: 10

```
Met Ala Pro Ile Glu Thr Asp Lys Ala Val Ser Ala Asn Glu Gly Leu
1               5                   10                  15

His Gln Arg Lys Gly Ala Ala Ser Ala Asp Lys Asp Ala Thr Tyr Thr
            20                  25                  30

Trp Gln Asp Val Ala Lys His Asn Thr Ala Lys Ser Ala Trp Val Ile
        35                  40                  45

Ile Arg Gly Val Val Tyr Asp Val Thr Asp Thr Leu Lys Thr Pro Gln
    50                  55                  60

Ser Lys Ile Leu Thr Cys Ser Cys Val Met Ala Pro Pro Glu Trp Ala
65                  70                  75                  80

Asp Arg His Pro Gly Gly Arg Glu Leu Val Leu His Ala Gly Arg
            85                  90                  95

Glu Cys Thr Asp Thr Phe Asp Ser Tyr His Pro Phe Ser Asn Arg Ala
            100                 105                 110

Asp Lys Ile Leu Ala Lys Tyr Ala Val Gly Lys Leu Val Gly Gly Ser
        115                 120                 125

Glu Phe Pro Gln Tyr Lys Pro Asp Thr Gly Phe Tyr Lys Glu Cys Cys
    130                 135                 140

Glu Arg Val His Gln Tyr Phe Lys Asp Asn Asn Leu Asp Pro Arg Ser
145                 150                 155                 160

Pro Tyr Ser Gly Met Trp Arg Met Met Ile Val Ala Ala Leu Gly Ala
                165                 170                 175

Ile Ser Tyr Leu Gly Met Asn Gln Leu Leu Ser Asp Asn Ile Tyr Ala
            180                 185                 190

His Tyr Ala Trp Gly Ala Leu Phe Gly Val Cys Gln Ala Leu Pro Leu
        195                 200                 205

Leu His Val Met His Asp Ala Ser His Ala Ala Ile Thr Ser Ser Pro
```

```
            210                 215                 220
Thr Gly Trp Arg Leu Ile Gly Arg Phe Ala Met Asp Trp Val Ala Gly
225                 230                 235                 240

Ala Asn Met Val Ser Trp Leu Asn Gln His Val Val Gly His His Ile
                245                 250                 255

Tyr Thr Asn Val Ala Gly Ala Asp Pro Asp Leu Pro Val Asp Phe Lys
                260                 265                 270

Ser Asp Val Arg Arg Ile Val Tyr Arg Gln Val Leu Leu Pro Ile Tyr
            275                 280                 285

Lys Phe Gln His Leu Tyr Leu Pro Pro Leu Tyr Gly Val Leu Gly Leu
        290                 295                 300

Lys Phe Arg Val Gln Asp Ile Phe Glu Thr Phe Ile Ser Leu Thr Asn
305                 310                 315                 320

Gly Pro Leu Arg Val Asn Pro His Ser Val Gly Asp Trp Val Glu Met
                325                 330                 335

Ile Leu Ser Lys Ala Phe Trp Ala Phe Tyr Arg Ile Tyr Ile Pro Leu
                340                 345                 350

Val Val Leu Gln Val Asp Ser Ser Arg Phe Trp Gly Val Phe Phe Leu
            355                 360                 365

Ala Glu Phe Met Thr Gly Trp Tyr Leu Ala Phe Asn Phe Gln Val Ser
        370                 375                 380

His Val Ser Thr Ala Cys Glu Tyr Pro Gly Gly Asp Glu Glu Val Thr
385                 390                 395                 400

Ala Ile Glu Asp Glu Trp Ala Val Ser Gln Ile Lys Ser Ser Val Asp
                405                 410                 415

Tyr Gly His Gly Ser Phe Leu Thr Ala Phe Leu Thr Gly Ala Leu Asn
            420                 425                 430

Tyr Gln Val Thr His His Leu Phe Pro Gly Val Ser Gln Tyr His Tyr
        435                 440                 445

Pro Ala Ile Ala Pro Ile Ile Asp Val Cys Asn Lys Tyr Lys Ile
    450                 455                 460

Lys Tyr Thr Val Leu Pro Thr Phe Thr Glu Ala Leu Ala Gly His Phe
465                 470                 475                 480

Asp His Leu Val Val Met Gly Lys Met Gly Lys Pro Val Ser Val His
                485                 490                 495

Met Gly

<210> SEQ ID NO 11
<211> LENGTH: 903
<212> TYPE: DNA
<213> ORGANISM: Ostreococcus tauri
<220> FEATURE:
<221> NAME/KEY: CDS
<222> LOCATION: (1)..(903)
<223> OTHER INFORMATION: Delta-5 elongase

<400> SEQUENCE: 11 atg tct gct tct gga gct ttg ttg cct gct att gct ttc gct gct tac     48
Met Ser Ala Ser Gly Ala Leu Leu Pro Ala Ile Ala Phe Ala Ala Tyr
1               5                   10                  15 gct tac gct acc tac gct tat gct ttc gag tgg tct cat gct aac gga     96
Ala Tyr Ala Thr Tyr Ala Tyr Ala Phe Glu Trp Ser His Ala Asn Gly
                20                  25                  30 atc gat aac gtg gat gct aga gag tgg att gga gct ttg tct ttg aga    144
Ile Asp Asn Val Asp Ala Arg Glu Trp Ile Gly Ala Leu Ser Leu Arg
            35                  40                  45 ctc cct gca att gct acc acc atg tac ctc ttg ttc tgc ctt gtg gga    192
```

```
                                                     -continued

Leu Pro Ala Ile Ala Thr Thr Met Tyr Leu Leu Phe Cys Leu Val Gly
    50                  55                  60 cct aga ttg atg gct aag agg gag gct ttt gat cct aag gga ttc atg      240
Pro Arg Leu Met Ala Lys Arg Glu Ala Phe Asp Pro Lys Gly Phe Met
65                  70                  75                  80 ctc gct tac aac gct tac caa acc gct ttc aac gtt gtg gtg ctc gga      288
Leu Ala Tyr Asn Ala Tyr Gln Thr Ala Phe Asn Val Val Val Leu Gly
                85                  90                  95 atg ttc gct aga gag atc tct gga ttg gga caa cct gtt tgg gga tct      336
Met Phe Ala Arg Glu Ile Ser Gly Leu Gly Gln Pro Val Trp Gly Ser
            100                 105                 110 act atg cct tgg agc gat agg aag tcc ttc aag att ttg ttg gga gtg      384
Thr Met Pro Trp Ser Asp Arg Lys Ser Phe Lys Ile Leu Leu Gly Val
        115                 120                 125 tgg ctc cat tac aac aat aag tac ctc gag ttg ttg gat act gtg ttc      432
Trp Leu His Tyr Asn Asn Lys Tyr Leu Glu Leu Leu Asp Thr Val Phe
    130                 135                 140 atg gtg gct agg aaa aag acc aag cag ctc tct ttc ttg cat gtg tac      480
Met Val Ala Arg Lys Lys Thr Lys Gln Leu Ser Phe Leu His Val Tyr
145                 150                 155                 160 cat cat gct ttg ttg att tgg gct tgg tgg ctt gtt tgt cat ctc atg      528
His His Ala Leu Leu Ile Trp Ala Trp Trp Leu Val Cys His Leu Met
                165                 170                 175 gct acc aac gat tgc atc gat gct tat ttc gga gct gct tgc aac tct      576
Ala Thr Asn Asp Cys Ile Asp Ala Tyr Phe Gly Ala Ala Cys Asn Ser
            180                 185                 190 ttc atc cac atc gtg atg tac tcc tac tac ctc atg tct gct ttg gga      624
Phe Ile His Ile Val Met Tyr Ser Tyr Tyr Leu Met Ser Ala Leu Gly
        195                 200                 205 att aga tgc cct tgg aag aga tat atc acc cag gct cag atg ttg caa      672
Ile Arg Cys Pro Trp Lys Arg Tyr Ile Thr Gln Ala Gln Met Leu Gln
    210                 215                 220 ttc gtg atc gtg ttc gct cat gct gtt ttc gtg ctc aga caa aag cac      720
Phe Val Ile Val Phe Ala His Ala Val Phe Val Leu Arg Gln Lys His
225                 230                 235                 240 tgc cct gtt act ttg cct tgg gca caa atg ttc gtg atg aca aat atg      768
Cys Pro Val Thr Leu Pro Trp Ala Gln Met Phe Val Met Thr Asn Met
                245                 250                 255 ttg gtg ctc ttc gga aac ttc tac ctc aag gct tac tct aac aag tct      816
Leu Val Leu Phe Gly Asn Phe Tyr Leu Lys Ala Tyr Ser Asn Lys Ser
            260                 265                 270 agg gga gat gga gct tct tct gtt aag cct gct gag act act aga gca      864
Arg Gly Asp Gly Ala Ser Ser Val Lys Pro Ala Glu Thr Thr Arg Ala
        275                 280                 285 cct tct gtg aga aga acc agg tcc agg aag atc gat tga                  903
Pro Ser Val Arg Arg Thr Arg Ser Arg Lys Ile Asp
    290                 295                 300

<210> SEQ ID NO 12
<211> LENGTH: 300
<212> TYPE: PRT
<213> ORGANISM: Ostreococcus tauri

<400> SEQUENCE: 12

Met Ser Ala Ser Gly Ala Leu Leu Pro Ala Ile Ala Phe Ala Ala Tyr
1               5                   10                  15

Ala Tyr Ala Thr Tyr Ala Tyr Ala Phe Glu Trp Ser His Ala Asn Gly
                20                  25                  30

Ile Asp Asn Val Asp Ala Arg Glu Trp Ile Gly Ala Leu Ser Leu Arg
            35                  40                  45
```

```
Leu Pro Ala Ile Ala Thr Thr Met Tyr Leu Leu Phe Cys Leu Val Gly
 50                  55                  60

Pro Arg Leu Met Ala Lys Arg Glu Ala Phe Asp Pro Lys Gly Phe Met
 65                  70                  75                  80

Leu Ala Tyr Asn Ala Tyr Gln Thr Ala Phe Asn Val Val Leu Gly
                 85                  90                  95

Met Phe Ala Arg Glu Ile Ser Gly Leu Gly Gln Pro Val Trp Gly Ser
                100                 105                 110

Thr Met Pro Trp Ser Asp Arg Lys Ser Phe Lys Ile Leu Leu Gly Val
                115                 120                 125

Trp Leu His Tyr Asn Asn Lys Tyr Leu Glu Leu Asp Thr Val Phe
                130                 135                 140

Met Val Ala Arg Lys Lys Thr Lys Gln Leu Ser Phe Leu His Val Tyr
145                 150                 155                 160

His His Ala Leu Leu Ile Trp Ala Trp Trp Leu Val Cys His Leu Met
                165                 170                 175

Ala Thr Asn Asp Cys Ile Asp Ala Tyr Phe Gly Ala Ala Cys Asn Ser
                180                 185                 190

Phe Ile His Ile Val Met Tyr Ser Tyr Tyr Leu Met Ser Ala Leu Gly
                195                 200                 205

Ile Arg Cys Pro Trp Lys Arg Tyr Ile Thr Gln Ala Gln Met Leu Gln
                210                 215                 220

Phe Val Ile Val Phe Ala His Ala Val Phe Val Leu Arg Gln Lys His
225                 230                 235                 240

Cys Pro Val Thr Leu Pro Trp Ala Gln Met Phe Val Met Thr Asn Met
                245                 250                 255

Leu Val Leu Phe Gly Asn Phe Tyr Leu Lys Ala Tyr Ser Asn Lys Ser
                260                 265                 270

Arg Gly Asp Gly Ala Ser Ser Val Lys Pro Ala Glu Thr Thr Arg Ala
                275                 280                 285

Pro Ser Val Arg Arg Thr Arg Ser Arg Lys Ile Asp
                290                 295                 300

<210> SEQ ID NO 13
<211> LENGTH: 903
<212> TYPE: DNA
<213> ORGANISM: Ostreococcus tauri
<220> FEATURE:
<221> NAME/KEY: CDS
<222> LOCATION: (1)..(903)
<223> OTHER INFORMATION: Delta-5 elongase

<400> SEQUENCE: 13 atg agc gcc tcc ggt gcg ctg ctg ccc gcg atc gcg ttc gcc gcg tac     48
Met Ser Ala Ser Gly Ala Leu Leu Pro Ala Ile Ala Phe Ala Ala Tyr
  1               5                  10                  15 gcg tac gcg acg tac gcc tac gcc ttt gag tgg tcg cac gcg aat ggc     96
Ala Tyr Ala Thr Tyr Ala Tyr Ala Phe Glu Trp Ser His Ala Asn Gly
                 20                  25                  30 atc gac aac gtc gac gcg cgc gag tgg atc ggt gcg ctg tcg ttg agg    144
Ile Asp Asn Val Asp Ala Arg Glu Trp Ile Gly Ala Leu Ser Leu Arg
             35                  40                  45 ctc ccg gcg atc gcg acg acg atg tac ctg ttg ttc tgc ctg gtc gga    192
Leu Pro Ala Ile Ala Thr Thr Met Tyr Leu Leu Phe Cys Leu Val Gly
 50                  55                  60 ccg agg ttg atg gcg aag cgc gag gcg ttc gac ccg aag ggg ttc atg    240
Pro Arg Leu Met Ala Lys Arg Glu Ala Phe Asp Pro Lys Gly Phe Met
 65                  70                  75                  80
```

| | | |
|---|---|---|
| ctg gcg tac aat gcg tat cag acg gcg ttc aac gtc gtc gtg ctc ggg<br>Leu Ala Tyr Asn Ala Tyr Gln Thr Ala Phe Asn Val Val Val Leu Gly<br>                85                            90                            95 | 288 |
| atg ttc gcg cga gag atc tcg ggg ctg ggg cag ccc gtg tgg ggg tca<br>Met Phe Ala Arg Glu Ile Ser Gly Leu Gly Gln Pro Val Trp Gly Ser<br>               100                          105                        110 | 336 |
| acc atg ccg tgg agc gat aga aaa tcg ttt aag atc ctc ctc ggg gtg<br>Thr Met Pro Trp Ser Asp Arg Lys Ser Phe Lys Ile Leu Leu Gly Val<br>        115                          120                          125 | 384 |
| tgg ttg cac tac aac aac aaa tat ttg gag cta ttg gac act gtg ttc<br>Trp Leu His Tyr Asn Asn Lys Tyr Leu Glu Leu Leu Asp Thr Val Phe<br>130                            135                          140 | 432 |
| atg gtt gcg cgc aag aag acg aag cag ttg agc ttc ttg cac gtt tat<br>Met Val Ala Arg Lys Lys Thr Lys Gln Leu Ser Phe Leu His Val Tyr<br>145                          150                          155                        160 | 480 |
| cat cac gcc ctg ttg atc tgg gcg tgg tgg ttg gtg tgt cac ttg atg<br>His His Ala Leu Leu Ile Trp Ala Trp Trp Leu Val Cys His Leu Met<br>               165                          170                        175 | 528 |
| gcc acg aac gat tgt atc gat gcc tac ttc ggc gcg gcg tgc aac tcg<br>Ala Thr Asn Asp Cys Ile Asp Ala Tyr Phe Gly Ala Ala Cys Asn Ser<br>        180                          185                          190 | 576 |
| ttc att cac atc gtg atg tac tcg tat tat ctc atg tcg gcg ctc ggc<br>Phe Ile His Ile Val Met Tyr Ser Tyr Tyr Leu Met Ser Ala Leu Gly<br>               195                          200                        205 | 624 |
| att cga tgc ccg tgg aag cga tac atc acc cag gct caa atg ctc caa<br>Ile Arg Cys Pro Trp Lys Arg Tyr Ile Thr Gln Ala Gln Met Leu Gln<br>210                            215                          220 | 672 |
| ttc gtc att gtc ttc gcg cac gcc gtg ttc gtg ctg cgt cag aag cac<br>Phe Val Ile Val Phe Ala His Ala Val Phe Val Leu Arg Gln Lys His<br>225                          230                          235                        240 | 720 |
| tgc ccg gtc acc ctt cct tgg gcg caa atg ttc gtc atg acg aac atg<br>Cys Pro Val Thr Leu Pro Trp Ala Gln Met Phe Val Met Thr Asn Met<br>                     245                          250                        255 | 768 |
| ctc gtg ctc ttc ggg aac ttc tac ctc aag gcg tac tcg aac aag tcg<br>Leu Val Leu Phe Gly Asn Phe Tyr Leu Lys Ala Tyr Ser Asn Lys Ser<br>                   260                          265                        270 | 816 |
| cgc ggc gac ggc gcg agt tcc gtg aaa cca gcc gag acc acg cgc gcg<br>Arg Gly Asp Gly Ala Ser Ser Val Lys Pro Ala Glu Thr Thr Arg Ala<br>        275                          280                          285 | 864 |
| ccc agc gtg cga cgc acg cga tct cga aaa att gac taa<br>Pro Ser Val Arg Arg Thr Arg Ser Arg Lys Ile Asp<br>290                          295                        300 | 903 |

```
<210> SEQ ID NO 14
<211> LENGTH: 300
<212> TYPE: PRT
<213> ORGANISM: Ostreococcus tauri

<400> SEQUENCE: 14
```

Met Ser Ala Ser Gly Ala Leu Leu Pro Ala Ile Ala Phe Ala Ala Tyr
1                 5                       10                       15

Ala Tyr Ala Thr Tyr Ala Tyr Ala Phe Glu Trp Ser His Ala Asn Gly
                 20                        25                        30

Ile Asp Asn Val Asp Ala Arg Glu Trp Ile Gly Ala Leu Ser Leu Arg
                35                        40                       45

Leu Pro Ala Ile Ala Thr Thr Met Tyr Leu Leu Phe Cys Leu Val Gly
        50                          55                          60

Pro Arg Leu Met Ala Lys Arg Glu Ala Phe Asp Pro Lys Gly Phe Met
65                         70                       75                       80

Leu Ala Tyr Asn Ala Tyr Gln Thr Ala Phe Asn Val Val Val Leu Gly

```
                            85                   90                   95
Met Phe Ala Arg Glu Ile Ser Gly Leu Gly Gln Pro Val Trp Gly Ser
                100                 105                 110

Thr Met Pro Trp Ser Asp Arg Lys Ser Phe Lys Ile Leu Leu Gly Val
            115                 120                 125

Trp Leu His Tyr Asn Asn Lys Tyr Leu Glu Leu Leu Asp Thr Val Phe
        130                 135                 140

Met Val Ala Arg Lys Lys Thr Lys Gln Leu Ser Phe Leu His Val Tyr
145                 150                 155                 160

His His Ala Leu Leu Ile Trp Ala Trp Trp Leu Val Cys His Leu Met
                165                 170                 175

Ala Thr Asn Asp Cys Ile Asp Ala Tyr Phe Gly Ala Ala Cys Asn Ser
            180                 185                 190

Phe Ile His Ile Val Met Tyr Ser Tyr Tyr Leu Met Ser Ala Leu Gly
        195                 200                 205

Ile Arg Cys Pro Trp Lys Arg Tyr Ile Thr Gln Ala Gln Met Leu Gln
    210                 215                 220

Phe Val Ile Val Phe Ala His Ala Val Phe Leu Arg Gln Lys His
225                 230                 235                 240

Cys Pro Val Thr Leu Pro Trp Ala Gln Met Phe Val Met Thr Asn Met
                245                 250                 255

Leu Val Leu Phe Gly Asn Phe Tyr Leu Lys Ala Tyr Ser Asn Lys Ser
            260                 265                 270

Arg Gly Asp Gly Ala Ser Ser Val Lys Pro Ala Glu Thr Thr Arg Ala
        275                 280                 285

Pro Ser Val Arg Arg Thr Arg Ser Arg Lys Ile Asp
    290                 295                 300

<210> SEQ ID NO 15
<211> LENGTH: 1512
<212> TYPE: DNA
<213> ORGANISM: Thalassiosira pseudonana
<220> FEATURE:
<221> NAME/KEY: CDS
<222> LOCATION: (1)..(1512)
<223> OTHER INFORMATION: Delta-4 desaturase

<400> SEQUENCE: 15 atg tgc aac ggc aac ctc cca gca tcc acc gca cag ctc aag tcc acc    48
Met Cys Asn Gly Asn Leu Pro Ala Ser Thr Ala Gln Leu Lys Ser Thr
1               5                   10                  15 tcg aag ccc cag cag caa cat gag cat cgc acc atc tcc aag tcc gag    96
Ser Lys Pro Gln Gln Gln His Glu His Arg Thr Ile Ser Lys Ser Glu
            20                  25                  30 ctc gcc caa cac aac acg ccc aaa tca gca tgg tgt gcc gtc cac tcc   144
Leu Ala Gln His Asn Thr Pro Lys Ser Ala Trp Cys Ala Val His Ser
        35                  40                  45 act ccc gcc acc gac cca tcc cac tcc aac aac aaa caa cac gca cac   192
Thr Pro Ala Thr Asp Pro Ser His Ser Asn Asn Lys Gln His Ala His
    50                  55                  60 cta gtc ctc gac att acc gac ttt gcg tcc cgc cat cca ggg gga gac   240
Leu Val Leu Asp Ile Thr Asp Phe Ala Ser Arg His Pro Gly Gly Asp
65                  70                  75                  80 ctc atc ctc ctc gct tcc ggc aaa gac gcc tcg gtg ctg ttt gaa aca   288
Leu Ile Leu Leu Ala Ser Gly Lys Asp Ala Ser Val Leu Phe Glu Thr
                85                  90                  95 tac cat cca cgt gga gtt ccg acg tct ctc att caa aag ctg cag att   336
Tyr His Pro Arg Gly Val Pro Thr Ser Leu Ile Gln Lys Leu Gln Ile
            100                 105                 110
```

```
gga gtg atg gag gag gag gcg ttt cgg gat tcg ttt tac agt tgg act      384
Gly Val Met Glu Glu Glu Ala Phe Arg Asp Ser Phe Tyr Ser Trp Thr
        115                 120                 125 gat tct gac ttt tat act gtg ttg aag agg agg gtt gtg gag cgg ttg      432
Asp Ser Asp Phe Tyr Thr Val Leu Lys Arg Arg Val Val Glu Arg Leu
130                 135                 140 gag gag agg ggg ttg gac agg agg gga tcg aaa gag att tgg atc aag      480
Glu Glu Arg Gly Leu Asp Arg Arg Gly Ser Lys Glu Ile Trp Ile Lys
145                 150                 155                 160 gct ttg ttc ttg ttg gtt gga ttt tgg tac tgt ttg tac aag atg tat      528
Ala Leu Phe Leu Leu Val Gly Phe Trp Tyr Cys Leu Tyr Lys Met Tyr
                165                 170                 175 act acg tcg gat atc gat cag tac ggt att gcc att gcc tat tct att      576
Thr Thr Ser Asp Ile Asp Gln Tyr Gly Ile Ala Ile Ala Tyr Ser Ile
            180                 185                 190 gga atg gga acc ttt gcg gca ttc atc ggc acg tgt att caa cac gat      624
Gly Met Gly Thr Phe Ala Ala Phe Ile Gly Thr Cys Ile Gln His Asp
        195                 200                 205 gga aat cac ggt gca ttc gct cag aac aag tta ctc aac aag ttg gct      672
Gly Asn His Gly Ala Phe Ala Gln Asn Lys Leu Leu Asn Lys Leu Ala
210                 215                 220 ggg tgg acg ttg gat atg att ggt gcg agt gcg ttt acg tgg gag ctt      720
Gly Trp Thr Leu Asp Met Ile Gly Ala Ser Ala Phe Thr Trp Glu Leu
225                 230                 235                 240 cag cac atg ctg ggg cat cat cca tat acg aat gtg ttg gat ggg gtg      768
Gln His Met Leu Gly His His Pro Tyr Thr Asn Val Leu Asp Gly Val
                245                 250                 255 gag gag gag agg aag gag agg ggg gag gat gtt gct ttg gaa gaa aag      816
Glu Glu Glu Arg Lys Glu Arg Gly Glu Asp Val Ala Leu Glu Glu Lys
            260                 265                 270 gat cag gat ttt gaa gtt gcc aca tcc gga cga tta tat cat att gat      864
Asp Gln Asp Phe Glu Val Ala Thr Ser Gly Arg Leu Tyr His Ile Asp
        275                 280                 285 gcc aat gta cgt tat ggt tcg gta tgg aat gtc atg agg ttt tgg gct      912
Ala Asn Val Arg Tyr Gly Ser Val Trp Asn Val Met Arg Phe Trp Ala
290                 295                 300 atg aag gtc att acg atg gga tat atg atg gga tta cca atc tac ttt      960
Met Lys Val Ile Thr Met Gly Tyr Met Met Gly Leu Pro Ile Tyr Phe
305                 310                 315                 320 cat gga gta ctg agg gga gtt gga ttg ttt gtt att ggg cat ttg gcg     1008
His Gly Val Leu Arg Gly Val Gly Leu Phe Val Ile Gly His Leu Ala
                325                 330                 335 tgt gga gag ttg ttg gcg acg atg ttt att gtg aat cac gtc att gag     1056
Cys Gly Glu Leu Leu Ala Thr Met Phe Ile Val Asn His Val Ile Glu
            340                 345                 350 ggt gtg agt tat gga acg aag gat ttg gtt ggt ggt gcg agt cat gta     1104
Gly Val Ser Tyr Gly Thr Lys Asp Leu Val Gly Gly Ala Ser His Val
        355                 360                 365 gat gag aag aag att gtc aag cca acg act gta ttg gga gat aca cca     1152
Asp Glu Lys Lys Ile Val Lys Pro Thr Thr Val Leu Gly Asp Thr Pro
370                 375                 380 atg gta aag act cgc gag gag gca ttg aaa agc aac agc aat aac aac     1200
Met Val Lys Thr Arg Glu Glu Ala Leu Lys Ser Asn Ser Asn Asn Asn
385                 390                 395                 400 aag aag aag gga gag aag aac tcg gta cca tcc gtt cca ttc aac gac     1248
Lys Lys Lys Gly Glu Lys Asn Ser Val Pro Ser Val Pro Phe Asn Asp
                405                 410                 415 tgg gca gca gtc caa tgc cag acc tcc gtg aat tgg tct cca ggc tca     1296
Trp Ala Ala Val Gln Cys Gln Thr Ser Val Asn Trp Ser Pro Gly Ser
            420                 425                 430
```

```
tgg ttc tgg aat cac ttt tct ggg gga ctc tct cat cag att gag cat    1344
Trp Phe Trp Asn His Phe Ser Gly Gly Leu Ser His Gln Ile Glu His
        435                 440                 445 cac ttg ttc ccc agc att tgt cat aca aac tac tgt cat atc cag gat    1392
His Leu Phe Pro Ser Ile Cys His Thr Asn Tyr Cys His Ile Gln Asp
    450                 455                 460 gtt gtg gag agt acg tgt gct gag tac gga gtt ccg tat cag agt gag    1440
Val Val Glu Ser Thr Cys Ala Glu Tyr Gly Val Pro Tyr Gln Ser Glu
465                 470                 475                 480 agt aat ttg ttt gtt gct tat gga aag atg att agt cat ttg aag ttt    1488
Ser Asn Leu Phe Val Ala Tyr Gly Lys Met Ile Ser His Leu Lys Phe
                485                 490                 495 ttg ggt aaa gcc aag tgt gag tag                                    1512
Leu Gly Lys Ala Lys Cys Glu
                500
```

<210> SEQ ID NO 16
<211> LENGTH: 503
<212> TYPE: PRT
<213> ORGANISM: Thalassiosira pseudonana

<400> SEQUENCE: 16

```
Met Cys Asn Gly Asn Leu Pro Ala Ser Thr Ala Gln Leu Lys Ser Thr
1               5                   10                  15

Ser Lys Pro Gln Gln His Glu His Arg Thr Ile Ser Lys Ser Glu
            20                  25                  30

Leu Ala Gln His Asn Thr Pro Lys Ser Ala Trp Cys Ala Val His Ser
        35                  40                  45

Thr Pro Ala Thr Asp Pro Ser His Ser Asn Asn Lys Gln His Ala His
    50                  55                  60

Leu Val Leu Asp Ile Thr Asp Phe Ala Ser Arg His Pro Gly Gly Asp
65                  70                  75                  80

Leu Ile Leu Leu Ala Ser Gly Lys Asp Ala Ser Val Leu Phe Glu Thr
                85                  90                  95

Tyr His Pro Arg Gly Val Pro Thr Ser Leu Ile Gln Lys Leu Gln Ile
            100                 105                 110

Gly Val Met Glu Glu Glu Ala Phe Arg Asp Ser Phe Tyr Ser Trp Thr
        115                 120                 125

Asp Ser Asp Phe Tyr Thr Val Leu Lys Arg Arg Val Glu Arg Leu
    130                 135                 140

Glu Glu Arg Gly Leu Asp Arg Arg Gly Ser Lys Glu Ile Trp Ile Lys
145                 150                 155                 160

Ala Leu Phe Leu Leu Val Gly Phe Trp Tyr Cys Leu Tyr Lys Met Tyr
                165                 170                 175

Thr Thr Ser Asp Ile Asp Gln Tyr Gly Ile Ala Ile Ala Tyr Ser Ile
            180                 185                 190

Gly Met Gly Thr Phe Ala Ala Phe Ile Gly Thr Cys Ile Gln His Asp
        195                 200                 205

Gly Asn His Gly Ala Phe Ala Gln Asn Lys Leu Leu Asn Lys Leu Ala
    210                 215                 220

Gly Trp Thr Leu Asp Met Ile Gly Ala Ser Ala Phe Thr Trp Glu Leu
225                 230                 235                 240

Gln His Met Leu Gly His His Pro Tyr Thr Asn Val Leu Asp Gly Val
                245                 250                 255

Glu Glu Glu Arg Lys Glu Arg Gly Glu Asp Val Ala Leu Glu Glu Lys
            260                 265                 270
```

```
Asp Gln Asp Phe Glu Val Ala Thr Ser Gly Arg Leu Tyr His Ile Asp
        275                 280                 285

Ala Asn Val Arg Tyr Gly Ser Val Trp Asn Val Met Arg Phe Trp Ala
    290                 295                 300

Met Lys Val Ile Thr Met Gly Tyr Met Met Gly Leu Pro Ile Tyr Phe
305                 310                 315                 320

His Gly Val Leu Arg Gly Val Gly Leu Phe Val Ile Gly His Leu Ala
                325                 330                 335

Cys Gly Glu Leu Leu Ala Thr Met Phe Ile Val Asn His Val Ile Glu
                340                 345                 350

Gly Val Ser Tyr Gly Thr Lys Asp Leu Val Gly Ala Ser His Val
                355                 360                 365

Asp Glu Lys Lys Ile Val Lys Pro Thr Thr Val Leu Gly Asp Thr Pro
    370                 375                 380

Met Val Lys Thr Arg Glu Glu Ala Leu Lys Ser Asn Ser Asn Asn
385                 390                 395                 400

Lys Lys Lys Gly Glu Lys Asn Ser Val Pro Ser Val Pro Phe Asn Asp
                405                 410                 415

Trp Ala Val Gln Cys Gln Thr Ser Val Asn Trp Ser Pro Gly Ser
                420                 425                 430

Trp Phe Trp Asn His Phe Ser Gly Gly Leu Ser His Gln Ile Glu His
            435                 440                 445

His Leu Phe Pro Ser Ile Cys His Thr Asn Tyr Cys His Ile Gln Asp
            450                 455                 460

Val Val Glu Ser Thr Cys Ala Glu Tyr Gly Val Pro Tyr Gln Ser Glu
465                 470                 475                 480

Ser Asn Leu Phe Val Ala Tyr Gly Lys Met Ile Ser His Leu Lys Phe
                485                 490                 495

Leu Gly Lys Ala Lys Cys Glu
            500

<210> SEQ ID NO 17
<211> LENGTH: 1611
<212> TYPE: DNA
<213> ORGANISM: Ostreococcus tauri
<220> FEATURE:
<221> NAME/KEY: CDS
<222> LOCATION: (1)..(1611)
<223> OTHER INFORMATION: Delta-4 desaturase

<400> SEQUENCE: 17 atg tac ctc gga cgc ggc cgt ctc gag agc ggg acg acg cga ggg atg     48
Met Tyr Leu Gly Arg Gly Arg Leu Glu Ser Gly Thr Thr Arg Gly Met
1               5                   10                  15 atg cgg acg cac gcg cgg cga ccg tcg acg acg tcg aat ccg tgc gcg     96
Met Arg Thr His Ala Arg Arg Pro Ser Thr Thr Ser Asn Pro Cys Ala
                20                  25                  30 cgg tca cgc gtg cgt aag acg acg gag cga tcg ctc gcg cga gtg cga    144
Arg Ser Arg Val Arg Lys Thr Thr Glu Arg Ser Leu Ala Arg Val Arg
            35                  40                  45 cga tcg acg agt gag aag gga agc gcg ctc gtg ctc gag cga gag agc    192
Arg Ser Thr Ser Glu Lys Gly Ser Ala Leu Val Leu Glu Arg Glu Ser
        50                  55                  60 gaa cgg gag aag gag gag gga ggg aaa gcg cga gcg gag gga ttg cga    240
Glu Arg Glu Lys Glu Glu Gly Gly Lys Ala Arg Ala Glu Gly Leu Arg
65                  70                  75                  80 ttc caa cgc ccg gac gtc gcc gcg ccg ggg gga gcg gat cct tgg aac    288
Phe Gln Arg Pro Asp Val Ala Ala Pro Gly Gly Ala Asp Pro Trp Asn
                85                  90                  95
```

|   |   |   |   |   |   |   |   |   |   |   |   |   |   |   |   |   |
|---|---|---|---|---|---|---|---|---|---|---|---|---|---|---|---|---|
| gac | gag | aag | tgg | aca | aag | acc | aag | tgg | acg | gta | ttc | aga | gac | gtc | gcg | 336 |
| Asp | Glu | Lys | Trp | Thr | Lys | Thr | Lys | Trp | Thr | Val | Phe | Arg | Asp | Val | Ala | |
| | | | | 100 | | | | 105 | | | | | 110 | | | |
| tac | gat | ctc | gat | cct | ttc | ttc | gct | cga | cac | ccc | gga | gga | gac | tgg | ctc | 384 |
| Tyr | Asp | Leu | Asp | Pro | Phe | Phe | Ala | Arg | His | Pro | Gly | Gly | Asp | Trp | Leu | |
| | | | 115 | | | | | 120 | | | | | 125 | | | |
| ctg | aac | ttg | gcc | gtg | gga | cga | gac | tgc | acc | gcg | ctc | atc | gaa | tcc | tat | 432 |
| Leu | Asn | Leu | Ala | Val | Gly | Arg | Asp | Cys | Thr | Ala | Leu | Ile | Glu | Ser | Tyr | |
| | | | 130 | | | | | 135 | | | | | 140 | | | |
| cac | ttg | cga | cca | gag | gtg | gcg | acg | gct | cgt | ttc | aga | atg | ctg | ccc | aaa | 480 |
| His | Leu | Arg | Pro | Glu | Val | Ala | Thr | Ala | Arg | Phe | Arg | Met | Leu | Pro | Lys | |
| 145 | | | | | 150 | | | | | 155 | | | | | 160 | |
| ctc | gag | gat | ttt | ccc | gtc | gag | gcc | gtg | ccc | aag | tcc | ccg | aga | ccg | aac | 528 |
| Leu | Glu | Asp | Phe | Pro | Val | Glu | Ala | Val | Pro | Lys | Ser | Pro | Arg | Pro | Asn | |
| | | | | 165 | | | | | 170 | | | | | 175 | | |
| gat | tcg | ccg | tta | tac | aac | aac | att | cgc | aac | cga | gtc | cgc | gaa | gag | ctc | 576 |
| Asp | Ser | Pro | Leu | Tyr | Asn | Asn | Ile | Arg | Asn | Arg | Val | Arg | Glu | Glu | Leu | |
| | | | 180 | | | | | 185 | | | | | 190 | | | |
| ttc | cca | gag | gag | gga | aag | aat | atg | cac | aga | cag | ggc | ggc | gac | cac | ggc | 624 |
| Phe | Pro | Glu | Glu | Gly | Lys | Asn | Met | His | Arg | Gln | Gly | Gly | Asp | His | Gly | |
| | | | 195 | | | | | 200 | | | | | 205 | | | |
| gac | ggt | gac | gat | tct | ggg | ttt | cgc | cgc | ctt | ttg | ctt | atg | ccg | tgt | acc | 672 |
| Asp | Gly | Asp | Asp | Ser | Gly | Phe | Arg | Arg | Leu | Leu | Leu | Met | Pro | Cys | Thr | |
| | | 210 | | | | | 215 | | | | | 220 | | | | |
| tat | tcc | ctt | ccg | ggg | gtt | cct | ttc | cgg | ctg | cct | cct | cgg | gtc | tcg | cgg | 720 |
| Tyr | Ser | Leu | Pro | Gly | Val | Pro | Phe | Arg | Leu | Pro | Pro | Arg | Val | Ser | Arg | |
| 225 | | | | | 230 | | | | | 235 | | | | | 240 | |
| ggg | cgt | gga | ttg | gtc | tca | cga | ttc | agg | cac | tgc | gcc | aac | cac | ggc | gcg | 768 |
| Gly | Arg | Gly | Leu | Val | Ser | Arg | Phe | Arg | His | Cys | Ala | Asn | His | Gly | Ala | |
| | | | | 245 | | | | | 250 | | | | | 255 | | |
| atg | tct | cct | tcg | ccg | gcc | gtt | aac | ggc | gtc | ctc | ggt | ttg | acg | aac | gat | 816 |
| Met | Ser | Pro | Ser | Pro | Ala | Val | Asn | Gly | Val | Leu | Gly | Leu | Thr | Asn | Asp | |
| | | | 260 | | | | | 265 | | | | | 270 | | | |
| ctc | atc | ggc | ggc | tcg | tcc | ttg | atg | tgg | aga | tat | cac | cac | caa | gtc | agc | 864 |
| Leu | Ile | Gly | Gly | Ser | Ser | Leu | Met | Trp | Arg | Tyr | His | His | Gln | Val | Ser | |
| | | | 275 | | | | | 280 | | | | | 285 | | | |
| cac | cac | att | cat | tgc | aac | gac | aac | gcc | atg | gat | caa | gac | gtg | tac | acg | 912 |
| His | His | Ile | His | Cys | Asn | Asp | Asn | Ala | Met | Asp | Gln | Asp | Val | Tyr | Thr | |
| | | 290 | | | | | 295 | | | | | 300 | | | | |
| gcg | atg | cca | tta | ttg | cgt | ttc | gac | gct | cgc | cgg | ccc | aag | tcc | tgg | tac | 960 |
| Ala | Met | Pro | Leu | Leu | Arg | Phe | Asp | Ala | Arg | Arg | Pro | Lys | Ser | Trp | Tyr | |
| 305 | | | | | 310 | | | | | 315 | | | | | 320 | |
| cat | cgc | ttc | cag | cag | tgg | tac | atg | ttt | tta | gcg | ttc | ccg | ttg | ttg | cag | 1008 |
| His | Arg | Phe | Gln | Gln | Trp | Tyr | Met | Phe | Leu | Ala | Phe | Pro | Leu | Leu | Gln | |
| | | | | 325 | | | | | 330 | | | | | 335 | | |
| gtt | gcc | ttc | caa | gtc | gga | gac | att | gcc | gca | ctg | ttc | acg | cgt | gat | acc | 1056 |
| Val | Ala | Phe | Gln | Val | Gly | Asp | Ile | Ala | Ala | Leu | Phe | Thr | Arg | Asp | Thr | |
| | | | 340 | | | | | 345 | | | | | 350 | | | |
| gaa | ggc | gct | aag | ctt | cac | ggg | gcg | acg | acg | tgg | gag | ctt | acc | acg | gtt | 1104 |
| Glu | Gly | Ala | Lys | Leu | His | Gly | Ala | Thr | Thr | Trp | Glu | Leu | Thr | Thr | Val | |
| | | | 355 | | | | | 360 | | | | | 365 | | | |
| gtc | ctc | ggt | aag | att | gtg | cac | ttc | ggt | ctt | ttg | ttg | ggg | ccg | ttg | atg | 1152 |
| Val | Leu | Gly | Lys | Ile | Val | His | Phe | Gly | Leu | Leu | Leu | Gly | Pro | Leu | Met | |
| | 370 | | | | | 375 | | | | | 380 | | | | | |
| aac | cac | gcg | gtg | agt | tct | gtt | ttg | ctg | ggg | atc | gtc | ggt | ttc | atg | gcg | 1200 |
| Asn | His | Ala | Val | Ser | Ser | Val | Leu | Leu | Gly | Ile | Val | Gly | Phe | Met | Ala | |
| 385 | | | | | 390 | | | | | 395 | | | | | 400 | |
| tgc | caa | ggt | ata | gtt | ctg | gcg | tgc | acg | ttt | gct | gtg | agt | cac | aat | gtc | 1248 |
| Cys | Gln | Gly | Ile | Val | Leu | Ala | Cys | Thr | Phe | Ala | Val | Ser | His | Asn | Val | |
| | | | | 405 | | | | | 410 | | | | | 415 | | |

```
gcg gag gcg aag ata cct gag gac acc gga gga gaa gcc tgg gag aga    1296
Ala Glu Ala Lys Ile Pro Glu Asp Thr Gly Gly Glu Ala Trp Glu Arg
        420                 425                 430 gat tgg ggt gtc cag cag ttg gtg act agc gcc gac tgg ggt gga aag    1344
Asp Trp Gly Val Gln Gln Leu Val Thr Ser Ala Asp Trp Gly Gly Lys
    435                 440                 445 ata ggt aac ttc ttc acg ggt ggc ctc aac ttg caa gtt gag cac cac    1392
Ile Gly Asn Phe Phe Thr Gly Gly Leu Asn Leu Gln Val Glu His His
450                 455                 460 ttg ttt ccg gcg att tgc ttc gtc cac tac ccg gac atc gcg aag atc    1440
Leu Phe Pro Ala Ile Cys Phe Val His Tyr Pro Asp Ile Ala Lys Ile
465                 470                 475                 480 gtg aag gaa gaa gcg gcc aag ctc aac atc cct tac gcg tct tac agg    1488
Val Lys Glu Glu Ala Ala Lys Leu Asn Ile Pro Tyr Ala Ser Tyr Arg
                485                 490                 495 act ctt cct ggt att ttc gtc caa ttc tgg aga ttt atg aag gac atg    1536
Thr Leu Pro Gly Ile Phe Val Gln Phe Trp Arg Phe Met Lys Asp Met
            500                 505                 510 ggc acg gct gag caa att ggt gaa gtt cca ttg ccg aag att ccc aac    1584
Gly Thr Ala Glu Gln Ile Gly Glu Val Pro Leu Pro Lys Ile Pro Asn
        515                 520                 525 ccg cag ctc gcg ccg aag ctc gct tag                                1611
Pro Gln Leu Ala Pro Lys Leu Ala
    530                 535

<210> SEQ ID NO 18
<211> LENGTH: 536
<212> TYPE: PRT
<213> ORGANISM: Ostreococcus tauri

<400> SEQUENCE: 18

Met Tyr Leu Gly Arg Gly Arg Leu Glu Ser Gly Thr Thr Arg Gly Met
1               5                   10                  15

Met Arg Thr His Ala Arg Arg Pro Ser Thr Thr Ser Asn Pro Cys Ala
            20                  25                  30

Arg Ser Arg Val Arg Lys Thr Thr Glu Arg Ser Leu Ala Arg Val Arg
        35                  40                  45

Arg Ser Thr Ser Glu Lys Gly Ser Ala Leu Val Leu Glu Arg Glu Ser
    50                  55                  60

Glu Arg Glu Lys Glu Gly Gly Lys Ala Arg Ala Glu Gly Leu Arg
65                  70                  75                  80

Phe Gln Arg Pro Asp Val Ala Pro Gly Gly Ala Asp Pro Trp Asn
                85                  90                  95

Asp Glu Lys Trp Thr Lys Thr Lys Trp Thr Val Phe Arg Asp Val Ala
            100                 105                 110

Tyr Asp Leu Asp Pro Phe Phe Ala Arg His Pro Gly Gly Asp Trp Leu
        115                 120                 125

Leu Asn Leu Ala Val Gly Arg Asp Cys Thr Ala Leu Ile Glu Ser Tyr
    130                 135                 140

His Leu Arg Pro Glu Val Ala Thr Ala Arg Phe Arg Met Leu Pro Lys
145                 150                 155                 160

Leu Glu Asp Phe Pro Val Glu Ala Val Pro Lys Ser Pro Arg Pro Asn
                165                 170                 175

Asp Ser Pro Leu Tyr Asn Asn Ile Arg Asn Arg Val Arg Glu Glu Leu
            180                 185                 190

Phe Pro Glu Glu Gly Lys Asn Met His Arg Gln Gly Gly Asp His Gly
        195                 200                 205
```

-continued

Asp Gly Asp Asp Ser Gly Phe Arg Arg Leu Leu Leu Met Pro Cys Thr
        210                 215                 220

Tyr Ser Leu Pro Gly Val Pro Phe Arg Leu Pro Pro Arg Val Ser Arg
225                 230                 235                 240

Gly Arg Gly Leu Val Ser Arg Phe Arg His Cys Ala Asn His Gly Ala
                245                 250                 255

Met Ser Pro Ser Pro Ala Val Asn Gly Val Leu Gly Leu Thr Asn Asp
            260                 265                 270

Leu Ile Gly Gly Ser Ser Leu Met Trp Arg Tyr His His Gln Val Ser
        275                 280                 285

His His Ile His Cys Asn Asp Asn Ala Met Asp Gln Asp Val Tyr Thr
    290                 295                 300

Ala Met Pro Leu Leu Arg Phe Asp Ala Arg Arg Pro Lys Ser Trp Tyr
305                 310                 315                 320

His Arg Phe Gln Gln Trp Tyr Met Phe Leu Ala Phe Pro Leu Leu Gln
                325                 330                 335

Val Ala Phe Gln Val Gly Asp Ile Ala Ala Leu Phe Thr Arg Asp Thr
            340                 345                 350

Glu Gly Ala Lys Leu His Gly Ala Thr Thr Trp Glu Leu Thr Thr Val
        355                 360                 365

Val Leu Gly Lys Ile Val His Phe Gly Leu Leu Gly Pro Leu Met
370                 375                 380

Asn His Ala Val Ser Ser Val Leu Leu Gly Ile Val Gly Phe Met Ala
385                 390                 395                 400

Cys Gln Gly Ile Val Leu Ala Cys Thr Phe Ala Val Ser His Asn Val
                405                 410                 415

Ala Glu Ala Lys Ile Pro Glu Asp Thr Gly Gly Glu Ala Trp Glu Arg
            420                 425                 430

Asp Trp Gly Val Gln Gln Leu Val Thr Ser Ala Asp Trp Gly Gly Lys
        435                 440                 445

Ile Gly Asn Phe Phe Thr Gly Gly Leu Asn Leu Gln Val Glu His His
    450                 455                 460

Leu Phe Pro Ala Ile Cys Phe Val His Tyr Pro Asp Ile Ala Lys Ile
465                 470                 475                 480

Val Lys Glu Glu Ala Ala Lys Leu Asn Ile Pro Tyr Ala Ser Tyr Arg
                485                 490                 495

Thr Leu Pro Gly Ile Phe Val Gln Phe Trp Arg Phe Met Lys Asp Met
            500                 505                 510

Gly Thr Ala Glu Gln Ile Gly Glu Val Pro Leu Pro Lys Ile Pro Asn
        515                 520                 525

Pro Gln Leu Ala Pro Lys Leu Ala
    530                 535

<210> SEQ ID NO 19
<211> LENGTH: 1548
<212> TYPE: DNA
<213> ORGANISM: Thraustochytrium
<220> FEATURE:
<221> NAME/KEY: CDS
<222> LOCATION: (1)..(1548)
<223> OTHER INFORMATION: Delta-4 desaturase

<400> SEQUENCE: 19 atg acg gtc ggg ttt gac gaa acg gtg act atg gac acg gtc cgc aac     48
Met Thr Val Gly Phe Asp Glu Thr Val Thr Met Asp Thr Val Arg Asn
1               5                   10                  15 cac aac atg ccg gac gac gcc tgg tgc gcg atc cac ggc acc gtg tac     96

-continued

|  |  |  |  |  |  |  |  |  |  |  |  |  |  |
|--|--|--|--|--|--|--|--|--|--|--|--|--|--|
| His | Asn | Met | Pro | Asp | Asp | Ala | Trp | Cys | Ala | Ile | His | Gly | Thr | Val | Tyr |
|  |  |  | 20 |  |  |  | 25 |  |  |  |  | 30 |  |  |  |

```
gac atc acc aag ttc agc aag gtg cac ccc ggc ggg gac atc atc atg      144
Asp Ile Thr Lys Phe Ser Lys Val His Pro Gly Gly Asp Ile Ile Met
        35              40              45 ctg gcc gct ggc aag gag gcc acc atc ctg ttc gag acc tac cac atc      192
Leu Ala Ala Gly Lys Glu Ala Thr Ile Leu Phe Glu Thr Tyr His Ile
    50              55              60 aag ggc gtc ccg gac gcg gtg ctg cgc aag tac aag gtc ggc aag ctc      240
Lys Gly Val Pro Asp Ala Val Leu Arg Lys Tyr Lys Val Gly Lys Leu
65              70              75              80 ccc cag ggc aag aag ggc gaa acg agc cac atg ccc acc ggg ctc gac      288
Pro Gln Gly Lys Lys Gly Glu Thr Ser His Met Pro Thr Gly Leu Asp
            85              90              95 tcg gcc tcc tac tac tcg tgg gac agc gag ttt tac agg gtg ctc cgc      336
Ser Ala Ser Tyr Tyr Ser Trp Asp Ser Glu Phe Tyr Arg Val Leu Arg
        100             105             110 gag cgc gtc gcc aag aag ctg gcc gag ccc ggc ctc atg cag cgc gcg      384
Glu Arg Val Ala Lys Lys Leu Ala Glu Pro Gly Leu Met Gln Arg Ala
    115             120             125 cgc atg gag ctc tgg gcc aag gcg atc ttc ctc ctg gca ggt ttc tgg      432
Arg Met Glu Leu Trp Ala Lys Ala Ile Phe Leu Leu Ala Gly Phe Trp
130             135             140 ggc tcc ctt tac gcc atg tgc gtg cta gac ccg cac ggc ggt gcc atg      480
Gly Ser Leu Tyr Ala Met Cys Val Leu Asp Pro His Gly Gly Ala Met
145             150             155             160 gta gcc gcc gtt acg ctc ggc gtg ttc gct gcc ttt gtc gga act tgc      528
Val Ala Ala Val Thr Leu Gly Val Phe Ala Ala Phe Val Gly Thr Cys
            165             170             175 atc cag cac gac ggc agc cac ggc gcc ttc tcc aag tcg cga ttc atg      576
Ile Gln His Asp Gly Ser His Gly Ala Phe Ser Lys Ser Arg Phe Met
        180             185             190 aac aag gcg gcg ggc tgg acc ctc gac atg atc ggc gcg agt gcg atg      624
Asn Lys Ala Ala Gly Trp Thr Leu Asp Met Ile Gly Ala Ser Ala Met
    195             200             205 acc tgg gag atg cag cac gtt ctt ggc cac cac ccg tac acc aac ctc      672
Thr Trp Glu Met Gln His Val Leu Gly His His Pro Tyr Thr Asn Leu
210             215             220 atc gag atg gag aac ggt ttg gcc aag gtc aag ggc gcc gac gtc gac      720
Ile Glu Met Glu Asn Gly Leu Ala Lys Val Lys Gly Ala Asp Val Asp
225             230             235             240 ccg aag aag gtc gac cag gag agc gac ccg gac gtc ttc agt acg tac      768
Pro Lys Lys Val Asp Gln Glu Ser Asp Pro Asp Val Phe Ser Thr Tyr
            245             250             255 ccg atg ctt cgc ctg cac ccg tgg cac cgc cag cgg ttt tac cac aag      816
Pro Met Leu Arg Leu His Pro Trp His Arg Gln Arg Phe Tyr His Lys
        260             265             270 ttc cag cac ctg tac gcc ccg ttt atc ttt ggg tct atg acg att aac      864
Phe Gln His Leu Tyr Ala Pro Phe Ile Phe Gly Ser Met Thr Ile Asn
    275             280             285 aag gtg att tcc cag gat gtc ggg gtt gtg ctg cgc aag cgc ctg ttc      912
Lys Val Ile Ser Gln Asp Val Gly Val Val Leu Arg Lys Arg Leu Phe
290             295             300 cag atc gac gcc aac tgc cgg tat ggc agc ccc tgg tac gtg gcc cgc      960
Gln Ile Asp Ala Asn Cys Arg Tyr Gly Ser Pro Trp Tyr Val Ala Arg
305             310             315             320 ttc tgg atc atg aag ctc ctc acc acg ctc tac atg gtg gcg ctt ccc     1008
Phe Trp Ile Met Lys Leu Leu Thr Thr Leu Tyr Met Val Ala Leu Pro
            325             330             335 atg tac atg cag ggg cct gct cag ggc ttg aag ctt ttc ttc atg gcc     1056
```

```
Met Tyr Met Gln Gly Pro Ala Gln Gly Leu Lys Leu Phe Met Ala
            340                 345                 350 cac ttc acc tgc gga gag gtc ctc gcc acc atg ttt att gtc aac cac    1104
His Phe Thr Cys Gly Glu Val Leu Ala Thr Met Phe Ile Val Asn His
        355                 360                 365 atc atc gag ggc gtc agc tac gct tcc aag gac gcg gtc aag ggc gtc    1152
Ile Ile Glu Gly Val Ser Tyr Ala Ser Lys Asp Ala Val Lys Gly Val
370                 375                 380 atg gct ccg ccg cgc act gtg cac ggt gtc acc ccg atg cag gtg acg    1200
Met Ala Pro Pro Arg Thr Val His Gly Val Thr Pro Met Gln Val Thr
385                 390                 395                 400 caa aag gcg ctc agt gcg gcc gag tcg gcc aag tcg gac gcc gac aag    1248
Gln Lys Ala Leu Ser Ala Ala Glu Ser Ala Lys Ser Asp Ala Asp Lys
                405                 410                 415 acg acc atg atc ccc ctc aac gac tgg gcc gct gtg cag tgc cag acc    1296
Thr Thr Met Ile Pro Leu Asn Asp Trp Ala Ala Val Gln Cys Gln Thr
            420                 425                 430 tct gtg aac tgg gct gtc ggg tcg tgg ttt tgg aac cac ttt tcg ggc    1344
Ser Val Asn Trp Ala Val Gly Ser Trp Phe Trp Asn His Phe Ser Gly
        435                 440                 445 ggc ctc aac cac cag att gag cac cac tgc ttc ccc caa aac ccc cac    1392
Gly Leu Asn His Gln Ile Glu His His Cys Phe Pro Gln Asn Pro His
    450                 455                 460 acg gtc aac gtc tac atc tcg ggc atc gtc aag gag acc tgc gaa gaa    1440
Thr Val Asn Val Tyr Ile Ser Gly Ile Val Lys Glu Thr Cys Glu Glu
465                 470                 475                 480 tac ggc gtg ccg tac cag gct gag atc agc ctc ttc tct gcc tat ttc    1488
Tyr Gly Val Pro Tyr Gln Ala Glu Ile Ser Leu Phe Ser Ala Tyr Phe
                485                 490                 495 aag atg ctg tcg cac ctc cgc acg ctc ggc aac gag gac ctc acg gcc    1536
Lys Met Leu Ser His Leu Arg Thr Leu Gly Asn Glu Asp Leu Thr Ala
            500                 505                 510 tgg tcc acg tga                                                     1548
Trp Ser Thr
        515

<210> SEQ ID NO 20
<211> LENGTH: 515
<212> TYPE: PRT
<213> ORGANISM: Thraustochytrium

<400> SEQUENCE: 20

Met Thr Val Gly Phe Asp Glu Thr Val Thr Met Asp Thr Val Arg Asn
1               5                   10                  15

His Asn Met Pro Asp Asp Ala Trp Cys Ala Ile His Gly Thr Val Tyr
            20                  25                  30

Asp Ile Thr Lys Phe Ser Lys Val His Pro Gly Gly Asp Ile Ile Met
        35                  40                  45

Leu Ala Ala Gly Lys Glu Ala Thr Ile Leu Phe Glu Thr Tyr His Ile
    50                  55                  60

Lys Gly Val Pro Asp Ala Val Leu Arg Lys Tyr Val Gly Lys Leu
65                  70                  75                  80

Pro Gln Gly Lys Lys Gly Glu Thr Ser His Met Pro Thr Gly Leu Asp
                85                  90                  95

Ser Ala Ser Tyr Tyr Ser Trp Asp Ser Glu Phe Tyr Arg Val Leu Arg
            100                 105                 110

Glu Arg Val Ala Lys Lys Leu Ala Glu Pro Gly Leu Met Gln Arg Ala
        115                 120                 125

Arg Met Glu Leu Trp Ala Lys Ala Ile Phe Leu Leu Ala Gly Phe Trp
```

```
             130                 135                 140
Gly Ser Leu Tyr Ala Met Cys Val Leu Asp Pro His Gly Gly Ala Met
145                 150                 155                 160
Val Ala Val Thr Leu Gly Val Phe Ala Phe Val Gly Thr Cys
                165                 170                 175
Ile Gln His Asp Gly Ser His Gly Ala Phe Ser Lys Ser Arg Phe Met
                180                 185                 190
Asn Lys Ala Ala Gly Trp Thr Leu Asp Met Ile Gly Ala Ser Ala Met
                195                 200                 205
Thr Trp Glu Met Gln His Val Leu Gly His His Pro Tyr Thr Asn Leu
210                 215                 220
Ile Glu Met Glu Asn Gly Leu Ala Lys Val Lys Gly Ala Asp Val Asp
225                 230                 235                 240
Pro Lys Lys Val Asp Gln Glu Ser Asp Pro Asp Val Phe Ser Thr Tyr
                245                 250                 255
Pro Met Leu Arg Leu His Pro Trp His Arg Gln Arg Phe Tyr His Lys
                260                 265                 270
Phe Gln His Leu Tyr Ala Pro Phe Ile Phe Gly Ser Met Thr Ile Asn
                275                 280                 285
Lys Val Ile Ser Gln Asp Val Gly Val Val Leu Arg Lys Arg Leu Phe
                290                 295                 300
Gln Ile Asp Ala Asn Cys Arg Tyr Gly Ser Pro Trp Tyr Val Ala Arg
305                 310                 315                 320
Phe Trp Ile Met Lys Leu Leu Thr Thr Leu Tyr Met Val Ala Leu Pro
                325                 330                 335
Met Tyr Met Gln Gly Pro Ala Gln Gly Leu Lys Leu Phe Phe Met Ala
                340                 345                 350
His Phe Thr Cys Gly Glu Val Leu Ala Thr Met Phe Ile Val Asn His
                355                 360                 365
Ile Ile Glu Gly Val Ser Tyr Ala Ser Lys Asp Ala Val Lys Gly Val
370                 375                 380
Met Ala Pro Pro Arg Thr Val His Gly Val Thr Pro Met Gln Val Thr
385                 390                 395                 400
Gln Lys Ala Leu Ser Ala Ala Glu Ser Ala Lys Ser Asp Ala Asp Lys
                405                 410                 415
Thr Thr Met Ile Pro Leu Asn Asp Trp Ala Ala Val Gln Cys Gln Thr
                420                 425                 430
Ser Val Asn Trp Ala Val Gly Ser Trp Phe Trp Asn His Phe Ser Gly
                435                 440                 445
Gly Leu Asn His Gln Ile Glu His His Cys Phe Pro Gln Asn Pro His
                450                 455                 460
Thr Val Asn Val Tyr Ile Ser Gly Ile Val Lys Glu Thr Cys Glu Glu
465                 470                 475                 480
Tyr Gly Val Pro Tyr Gln Ala Glu Ile Ser Leu Phe Ser Ala Tyr Phe
                485                 490                 495
Lys Met Leu Ser His Leu Arg Thr Leu Gly Asn Glu Asp Leu Thr Ala
                500                 505                 510
Trp Ser Thr
        515

<210> SEQ ID NO 21
<211> LENGTH: 1626
<212> TYPE: DNA
<213> ORGANISM: Euglena gracilis
<220> FEATURE:
```

```
<221> NAME/KEY: CDS
<222> LOCATION: (1)..(1626)
<223> OTHER INFORMATION: Delta-4 desaturase

<400> SEQUENCE: 21 atg ttg gtg ctg ttt ggc aat ttc tat gtc aag caa tac tcc caa aag      48
Met Leu Val Leu Phe Gly Asn Phe Tyr Val Lys Gln Tyr Ser Gln Lys
1               5                   10                  15 aac ggc aag ccg gag aac gga gcc acc cct gag aac gga gcg aag ccg      96
Asn Gly Lys Pro Glu Asn Gly Ala Thr Pro Glu Asn Gly Ala Lys Pro
                20                  25                  30 caa cct tgc gag aac ggc acg gtg gaa aag cga gag aat gac acc gcc     144
Gln Pro Cys Glu Asn Gly Thr Val Glu Lys Arg Glu Asn Asp Thr Ala
            35                  40                  45 aac gtt cgg ccc acc cgt cca gct gga ccc ccg ccg gcc acg tac tac     192
Asn Val Arg Pro Thr Arg Pro Ala Gly Pro Pro Pro Ala Thr Tyr Tyr
        50                  55                  60 gac tcc ctg gca gtg tcg ggg cag ggc aag gag cgg ctg ttc acc acc     240
Asp Ser Leu Ala Val Ser Gly Gln Gly Lys Glu Arg Leu Phe Thr Thr
65                  70                  75                  80 gat gag gtg agg cgg cac atc ctc ccc acc gat ggc tgg ctg acg tgc     288
Asp Glu Val Arg Arg His Ile Leu Pro Thr Asp Gly Trp Leu Thr Cys
                85                  90                  95 cac gaa gga gtc tac gat gtc act gat ttc ctt gcc aag cac cct ggt     336
His Glu Gly Val Tyr Asp Val Thr Asp Phe Leu Ala Lys His Pro Gly
                100                 105                 110 ggc ggt gtc atc acg ctg ggc ctt gga agg gac tgc aca atc ctc atc     384
Gly Gly Val Ile Thr Leu Gly Leu Gly Arg Asp Cys Thr Ile Leu Ile
            115                 120                 125 gag tca tac cac cct gct ggg cgc ccg gac aag gtg atg gag aag tac     432
Glu Ser Tyr His Pro Ala Gly Arg Pro Asp Lys Val Met Glu Lys Tyr
130                 135                 140 cgc att ggt acg ctg cag gac ccc aag acg ttc tat gct tgg gga gag     480
Arg Ile Gly Thr Leu Gln Asp Pro Lys Thr Phe Tyr Ala Trp Gly Glu
145                 150                 155                 160 tcc gat ttc tac cct gag ttg aag cgc cgg gcc ctt gca agg ctg aag     528
Ser Asp Phe Tyr Pro Glu Leu Lys Arg Arg Ala Leu Ala Arg Leu Lys
                165                 170                 175 gag gct ggt cag gcg cgg cgc ggc ggc ctt ggg gtg aag gcc ctc ctg     576
Glu Ala Gly Gln Ala Arg Arg Gly Gly Leu Gly Val Lys Ala Leu Leu
            180                 185                 190 gtg ctc acc ctc ttc ttc gtg tcg tgg tac atg tgg gtg gcc cac aag     624
Val Leu Thr Leu Phe Phe Val Ser Trp Tyr Met Trp Val Ala His Lys
        195                 200                 205 tcc ttc ctc tgg gcc gcc gtc tgg ggc ttc gcc ggc tcc cac gtc ggg     672
Ser Phe Leu Trp Ala Ala Val Trp Gly Phe Ala Gly Ser His Val Gly
210                 215                 220 ctg agc atc cag cac gat ggc aac cac ggc gcg ttc agc cgc aac aca     720
Leu Ser Ile Gln His Asp Gly Asn His Gly Ala Phe Ser Arg Asn Thr
225                 230                 235                 240 ctg gtg aac cgc ctg gcg ggg tgg ggc atg gac ttg atc ggc gcg tcg     768
Leu Val Asn Arg Leu Ala Gly Trp Gly Met Asp Leu Ile Gly Ala Ser
                245                 250                 255 tcc acg gtg tgg gag tac cag cac gtc atc ggc cac cac cag tac acc     816
Ser Thr Val Trp Glu Tyr Gln His Val Ile Gly His His Gln Tyr Thr
            260                 265                 270 aac ctc gtg tcg gac acg cta ttc agt ctg cct gag aac gat ccg gac     864
Asn Leu Val Ser Asp Thr Leu Phe Ser Leu Pro Glu Asn Asp Pro Asp
        275                 280                 285 gtc ttc tcc agc tac ccg ctg atg cgc atg cac ccg gat acg gcg tgg     912
Val Phe Ser Ser Tyr Pro Leu Met Arg Met His Pro Asp Thr Ala Trp
```

```
                290                 295                 300
cag ccg cac cac cgc ttc cag cac ctg ttc gcg ttc cca ctg ttc gcc    960
Gln Pro His His Arg Phe Gln His Leu Phe Ala Phe Pro Leu Phe Ala
305                 310                 315                 320 ctg atg aca atc agc aag gtg ctg acc agc gat ttc gct gtc tgc ctc   1008
Leu Met Thr Ile Ser Lys Val Leu Thr Ser Asp Phe Ala Val Cys Leu
            325                 330                 335 agc atg aag aag ggg tcc atc gac tgc tcc tcc agg ctc gtc cca ctg   1056
Ser Met Lys Lys Gly Ser Ile Asp Cys Ser Ser Arg Leu Val Pro Leu
        340                 345                 350 gag ggg cag ctg ctg ttc tgg ggg gcc aag ctg gcg aac ttc ctg ttg   1104
Glu Gly Gln Leu Leu Phe Trp Gly Ala Lys Leu Ala Asn Phe Leu Leu
    355                 360                 365 cag att gtg ttg cca tgc tac ctc cac ggg aca gct atg ggc ctg gcc   1152
Gln Ile Val Leu Pro Cys Tyr Leu His Gly Thr Ala Met Gly Leu Ala
370                 375                 380 ctc ttc tct gtt gct cac ctt gtg tcg ggg gag tac ctc gcg atc tgc   1200
Leu Phe Ser Val Ala His Leu Val Ser Gly Glu Tyr Leu Ala Ile Cys
385                 390                 395                 400 ttc atc atc aac cac atc agc gag tct tgt gag ttt atg aat aca agc   1248
Phe Ile Ile Asn His Ile Ser Glu Ser Cys Glu Phe Met Asn Thr Ser
            405                 410                 415 ttt caa acc gcc gcc cgg agg aca gag atg ctt cag gca gca cat cag   1296
Phe Gln Thr Ala Ala Arg Arg Thr Glu Met Leu Gln Ala Ala His Gln
        420                 425                 430 gca gcg gag gcc aag aag gtg aag ccc acc cct cca ccg aac gat tgg   1344
Ala Ala Glu Ala Lys Lys Val Lys Pro Thr Pro Pro Pro Asn Asp Trp
    435                 440                 445 gct gtg aca cag gtc caa tgc tgc gtg aat tgg aga tca ggt ggc gtg   1392
Ala Val Thr Gln Val Gln Cys Cys Val Asn Trp Arg Ser Gly Gly Val
450                 455                 460 ttg gcc aat cac ctc tct gga ggc ttg aac cac cag atc gag cat cat   1440
Leu Ala Asn His Leu Ser Gly Gly Leu Asn His Gln Ile Glu His His
465                 470                 475                 480 ctg ttc ccc agc atc tcg cat gcc aac tac ccc acc atc gcc cct gtt   1488
Leu Phe Pro Ser Ile Ser His Ala Asn Tyr Pro Thr Ile Ala Pro Val
            485                 490                 495 gtg aag gag gtg tgc gag gag tac ggg ttg ccg tac aag aat tac gtc   1536
Val Lys Glu Val Cys Glu Glu Tyr Gly Leu Pro Tyr Lys Asn Tyr Val
        500                 505                 510 acg ttc tgg gat gca gtc tgt ggc atg gtt cag cac ctc cgg ttg atg   1584
Thr Phe Trp Asp Ala Val Cys Gly Met Val Gln His Leu Arg Leu Met
    515                 520                 525 ggt gct cca ccg gtg cca acg aac ggg gac aaa aag tca taa           1626
Gly Ala Pro Pro Val Pro Thr Asn Gly Asp Lys Lys Ser
530                 535                 540

<210> SEQ ID NO 22
<211> LENGTH: 541
<212> TYPE: PRT
<213> ORGANISM: Euglena gracilis

<400> SEQUENCE: 22

Met Leu Val Leu Phe Gly Asn Phe Tyr Val Lys Gln Tyr Ser Gln Lys
1               5                   10                  15

Asn Gly Lys Pro Glu Asn Gly Ala Thr Pro Glu Asn Gly Ala Lys Pro
            20                  25                  30

Gln Pro Cys Glu Asn Gly Thr Val Glu Lys Arg Glu Asn Asp Thr Ala
        35                  40                  45

Asn Val Arg Pro Thr Arg Pro Ala Gly Pro Pro Ala Thr Tyr Tyr
```

-continued

```
            50                  55                  60
Asp Ser Leu Ala Val Ser Gly Gln Gly Lys Glu Arg Leu Phe Thr Thr
 65                  70                  75                  80

Asp Glu Val Arg Arg His Ile Leu Pro Thr Asp Gly Trp Leu Thr Cys
                     85                  90                  95

His Glu Gly Val Tyr Asp Val Thr Asp Phe Leu Ala Lys His Pro Gly
                100                 105                 110

Gly Gly Val Ile Thr Leu Gly Leu Gly Arg Asp Cys Thr Ile Leu Ile
                115                 120                 125

Glu Ser Tyr His Pro Ala Gly Arg Pro Asp Lys Val Met Glu Lys Tyr
                130                 135                 140

Arg Ile Gly Thr Leu Gln Asp Pro Lys Thr Phe Tyr Ala Trp Gly Glu
145                 150                 155                 160

Ser Asp Phe Tyr Pro Glu Leu Lys Arg Arg Ala Leu Ala Arg Leu Lys
                165                 170                 175

Glu Ala Gly Gln Ala Arg Arg Gly Gly Leu Gly Val Lys Ala Leu Leu
                180                 185                 190

Val Leu Thr Leu Phe Phe Val Ser Trp Tyr Met Trp Val Ala His Lys
                195                 200                 205

Ser Phe Leu Trp Ala Ala Val Trp Gly Phe Ala Gly Ser His Val Gly
                210                 215                 220

Leu Ser Ile Gln His Asp Gly Asn His Gly Ala Phe Ser Arg Asn Thr
225                 230                 235                 240

Leu Val Asn Arg Leu Ala Gly Trp Gly Met Asp Leu Ile Gly Ala Ser
                245                 250                 255

Ser Thr Val Trp Glu Tyr Gln His Val Ile Gly His His Gln Tyr Thr
                260                 265                 270

Asn Leu Val Ser Asp Thr Leu Phe Ser Leu Pro Glu Asn Asp Pro Asp
                275                 280                 285

Val Phe Ser Ser Tyr Pro Leu Met Arg Met His Pro Asp Thr Ala Trp
                290                 295                 300

Gln Pro His His Arg Phe Gln His Leu Phe Ala Phe Pro Leu Phe Ala
305                 310                 315                 320

Leu Met Thr Ile Ser Lys Val Leu Thr Ser Asp Phe Ala Val Cys Leu
                325                 330                 335

Ser Met Lys Lys Gly Ser Ile Asp Cys Ser Ser Arg Leu Val Pro Leu
                340                 345                 350

Glu Gly Gln Leu Leu Phe Trp Gly Ala Lys Leu Ala Asn Phe Leu Leu
                355                 360                 365

Gln Ile Val Leu Pro Cys Tyr Leu His Gly Thr Ala Met Gly Leu Ala
370                 375                 380

Leu Phe Ser Val Ala His Leu Val Ser Gly Glu Tyr Leu Ala Ile Cys
385                 390                 395                 400

Phe Ile Ile Asn His Ile Ser Glu Ser Cys Glu Phe Met Asn Thr Ser
                405                 410                 415

Phe Gln Thr Ala Ala Arg Arg Thr Glu Met Leu Gln Ala Ala His Gln
                420                 425                 430

Ala Ala Glu Ala Lys Lys Val Lys Pro Thr Pro Pro Asn Asp Trp
                435                 440                 445

Ala Val Thr Gln Val Gln Cys Cys Val Asn Trp Arg Ser Gly Gly Val
                450                 455                 460

Leu Ala Asn His Leu Ser Gly Gly Leu Asn His Gln Ile Glu His His
465                 470                 475                 480
```

```
                 -continued

Leu Phe Pro Ser Ile Ser His Ala Asn Tyr Pro Thr Ile Ala Pro Val
                485                 490                 495

Val Lys Glu Val Cys Glu Glu Tyr Gly Leu Pro Tyr Lys Asn Tyr Val
            500                 505                 510

Thr Phe Trp Asp Ala Val Cys Gly Met Val Gln His Leu Arg Leu Met
        515                 520                 525

Gly Ala Pro Pro Val Pro Thr Asn Gly Asp Lys Lys Ser
    530                 535                 540

<210> SEQ ID NO 23
<211> LENGTH: 1092
<212> TYPE: DNA
<213> ORGANISM: Phytophthora sojae
<220> FEATURE:
<221> NAME/KEY: CDS
<222> LOCATION: (1)..(1092)
<223> OTHER INFORMATION: Omega-3 desaturase

<400> SEQUENCE: 23 atg gcg tcc aag cag gag cag ccg tac cag ttc ccg acg ctg acg gag      48
Met Ala Ser Lys Gln Glu Gln Pro Tyr Gln Phe Pro Thr Leu Thr Glu
1               5                   10                  15 atc aag cgc tcg ctg ccc agc gag tgt ttc gag gcg tcc gtg ccg ctc      96
Ile Lys Arg Ser Leu Pro Ser Glu Cys Phe Glu Ala Ser Val Pro Leu
            20                  25                  30 tcg ctc tac tac acg gtg cgc tgc ctg gtg atc gcc gtg tcg ctg gcc     144
Ser Leu Tyr Tyr Thr Val Arg Cys Leu Val Ile Ala Val Ser Leu Ala
        35                  40                  45 ttc ggg ctc cac cac gcg cgc tcg ctg ccc gtg gtc gag ggc ctc tgg     192
Phe Gly Leu His His Ala Arg Ser Leu Pro Val Val Glu Gly Leu Trp
    50                  55                  60 gcg ctg gac gcc gcg ctc tgc acg ggc tac gtg ctg ctg cag ggc atc     240
Ala Leu Asp Ala Ala Leu Cys Thr Gly Tyr Val Leu Leu Gln Gly Ile
65                  70                  75                  80 gtg ttc tgg ggc ttc ttc acc gtg ggc cat gac gcc ggc cac ggc gcc     288
Val Phe Trp Gly Phe Phe Thr Val Gly His Asp Ala Gly His Gly Ala
                85                  90                  95 ttc tcg cgc tac cac ctg ctc aac ttc gtg atc ggc acc ttc atc cac     336
Phe Ser Arg Tyr His Leu Leu Asn Phe Val Ile Gly Thr Phe Ile His
            100                 105                 110 tcg ctc atc ctg acg ccc ttc gag tcg tgg aag ctc acg cac cgc cac     384
Ser Leu Ile Leu Thr Pro Phe Glu Ser Trp Lys Leu Thr His Arg His
        115                 120                 125 cac cac aag aac acg ggc aac atc gac cgc gac gag atc ttc tac ccg     432
His His Lys Asn Thr Gly Asn Ile Asp Arg Asp Glu Ile Phe Tyr Pro
    130                 135                 140 cag cgc aag gcc gac gac cac ccg ctc tcg cgt aac ctc atc ctg gcg     480
Gln Arg Lys Ala Asp Asp His Pro Leu Ser Arg Asn Leu Ile Leu Ala
145                 150                 155                 160 ctg ggc gcc gcg tgg ttc gcc tac ctg gtc gag ggc ttc ccg ccg cgc     528
Leu Gly Ala Ala Trp Phe Ala Tyr Leu Val Glu Gly Phe Pro Pro Arg
                165                 170                 175 aag gtc aac cac ttc aac ccg ttc gag ccg ctg ttc gtc cgc cag gtg     576
Lys Val Asn His Phe Asn Pro Phe Glu Pro Leu Phe Val Arg Gln Val
            180                 185                 190 tcc gcc gtg gtc atc tcg ctg gcc gcg cac ttc ggc gtg gcc gcg ctg     624
Ser Ala Val Val Ile Ser Leu Ala Ala His Phe Gly Val Ala Ala Leu
        195                 200                 205 tcc atc tac ctg agc ctg cag ttc ggc ttc aag acc atg gct atc tac     672
Ser Ile Tyr Leu Ser Leu Gln Phe Gly Phe Lys Thr Met Ala Ile Tyr
    210                 215                 220
```

```
tac tac ggg ccc gtg ttc gtg ttc ggc agc atg ctg gtc atc acc acc       720
Tyr Tyr Gly Pro Val Phe Val Phe Gly Ser Met Leu Val Ile Thr Thr
225                 230                 235                 240 ttc ctg cac cac aac gac gag gag acc ccc tgg tac gcc gac tcg gag       768
Phe Leu His His Asn Asp Glu Glu Thr Pro Trp Tyr Ala Asp Ser Glu
                245                 250                 255 tgg acc tac gtc aag ggc aac ctc tcg tcg gtc gac cgc tcc tac ggc       816
Trp Thr Tyr Val Lys Gly Asn Leu Ser Ser Val Asp Arg Ser Tyr Gly
        260                 265                 270 gcg ctc atc gac aac ctg agc cac aac atc ggc acg cac cag atc cac       864
Ala Leu Ile Asp Asn Leu Ser His Asn Ile Gly Thr His Gln Ile His
    275                 280                 285 cac ctc ttc ccc atc atc ccg cac tat aag ctc aag cgc gcc acc gag       912
His Leu Phe Pro Ile Ile Pro His Tyr Lys Leu Lys Arg Ala Thr Glu
290                 295                 300 gcc ttc cac cag gcg ttc ccc gag ctc gtg cgc aag agc gac gag ccc       960
Ala Phe His Gln Ala Phe Pro Glu Leu Val Arg Lys Ser Asp Glu Pro
305                 310                 315                 320 atc att aag gcc ttc ttc cgc gtc ggc cgc ctc tac gcc aac tac ggc      1008
Ile Ile Lys Ala Phe Phe Arg Val Gly Arg Leu Tyr Ala Asn Tyr Gly
                325                 330                 335 gtc gtg gac tcg gac gcc aag ctc ttc acg ctc aag gag gcc aag gcc      1056
Val Val Asp Ser Asp Ala Lys Leu Phe Thr Leu Lys Glu Ala Lys Ala
                340                 345                 350 gtg tcc gag gcg gcg acc aag act aag gcc aac tga                      1092
Val Ser Glu Ala Ala Thr Lys Thr Lys Ala Asn
        355                 360
```

<210> SEQ ID NO 24
<211> LENGTH: 363
<212> TYPE: PRT
<213> ORGANISM: Phytophthora sojae

<400> SEQUENCE: 24

```
Met Ala Ser Lys Gln Glu Gln Pro Tyr Gln Phe Pro Thr Leu Thr Glu
1               5                   10                  15

Ile Lys Arg Ser Leu Pro Ser Glu Cys Phe Glu Ala Ser Val Pro Leu
            20                  25                  30

Ser Leu Tyr Tyr Thr Val Arg Cys Leu Val Ile Ala Val Ser Leu Ala
        35                  40                  45

Phe Gly Leu His His Ala Arg Ser Leu Pro Val Val Glu Gly Leu Trp
    50                  55                  60

Ala Leu Asp Ala Ala Leu Cys Thr Gly Tyr Val Leu Leu Gln Gly Ile
65                  70                  75                  80

Val Phe Trp Gly Phe Phe Thr Val Gly His Asp Ala Gly His Gly Ala
                85                  90                  95

Phe Ser Arg Tyr His Leu Leu Asn Phe Val Ile Gly Thr Phe Ile His
            100                 105                 110

Ser Leu Ile Leu Thr Pro Phe Glu Ser Trp Lys Leu Thr His Arg His
        115                 120                 125

His His Lys Asn Thr Gly Asn Ile Asp Arg Asp Glu Ile Phe Tyr Pro
    130                 135                 140

Gln Arg Lys Ala Asp Asp His Pro Leu Ser Arg Asn Leu Ile Leu Ala
145                 150                 155                 160

Leu Gly Ala Ala Trp Phe Ala Tyr Leu Val Glu Gly Phe Pro Pro Arg
                165                 170                 175

Lys Val Asn His Phe Asn Pro Phe Glu Pro Leu Phe Val Arg Gln Val
            180                 185                 190
```

```
Ser Ala Val Val Ile Ser Leu Ala Ala His Phe Gly Val Ala Ala Leu
        195                 200                 205

Ser Ile Tyr Leu Ser Leu Gln Phe Gly Phe Lys Thr Met Ala Ile Tyr
    210                 215                 220

Tyr Tyr Gly Pro Val Phe Val Phe Gly Ser Met Leu Val Ile Thr Thr
225                 230                 235                 240

Phe Leu His His Asn Asp Glu Glu Thr Pro Trp Tyr Ala Asp Ser Glu
                245                 250                 255

Trp Thr Tyr Val Lys Gly Asn Leu Ser Ser Val Asp Arg Ser Tyr Gly
                260                 265                 270

Ala Leu Ile Asp Asn Leu Ser His Asn Ile Gly Thr His Gln Ile His
            275                 280                 285

His Leu Phe Pro Ile Ile Pro His Tyr Lys Leu Lys Arg Ala Thr Glu
        290                 295                 300

Ala Phe His Gln Ala Phe Pro Glu Leu Val Arg Lys Ser Asp Glu Pro
305                 310                 315                 320

Ile Ile Lys Ala Phe Phe Arg Val Gly Arg Leu Tyr Ala Asn Tyr Gly
                325                 330                 335

Val Val Asp Ser Asp Ala Lys Leu Phe Thr Leu Lys Glu Ala Lys Ala
            340                 345                 350

Val Ser Glu Ala Ala Thr Lys Thr Lys Ala Asn
        355                 360

<210> SEQ ID NO 25
<211> LENGTH: 1197
<212> TYPE: DNA
<213> ORGANISM: Phytophthora sojae
<220> FEATURE:
<221> NAME/KEY: CDS
<222> LOCATION: (1)..(1197)
<223> OTHER INFORMATION: Delta-12 desaturase

<400> SEQUENCE: 25 atg gcg atc ctg aac ccg gag gcc gac tcg gcc gcc aat ctg gcc acc    48
Met Ala Ile Leu Asn Pro Glu Ala Asp Ser Ala Ala Asn Leu Ala Thr
1               5                   10                  15 gac agc gag gcc aag cag cgc cag ctc gcg gag gcc ggc tac acg cac    96
Asp Ser Glu Ala Lys Gln Arg Gln Leu Ala Glu Ala Gly Tyr Thr His
            20                  25                  30 gtg gag ggc gcg ccg gcg cca ctg ccg ctg gag ctg ccg cac ttc tcg   144
Val Glu Gly Ala Pro Ala Pro Leu Pro Leu Glu Leu Pro His Phe Ser
        35                  40                  45 ctg cgc gac ctg cgc gcc gcc atc ccc aag cac tgc ttc gag cgc tcg   192
Leu Arg Asp Leu Arg Ala Ala Ile Pro Lys His Cys Phe Glu Arg Ser
    50                  55                  60 ttc gtc acg tcc acg tac tac atg atc aag aac gtg ctc acg tgc gcc   240
Phe Val Thr Ser Thr Tyr Tyr Met Ile Lys Asn Val Leu Thr Cys Ala
65                  70                  75                  80 gcg ctc ttc tac gcg gcc acc ttc atc gac cgc gcg ggc gcc gcc gcc   288
Ala Leu Phe Tyr Ala Ala Thr Phe Ile Asp Arg Ala Gly Ala Ala Ala
                85                  90                  95 tac gtg ctg tgg ccc gtg tac tgg ttc ttc cag ggc agc tac ctc acg   336
Tyr Val Leu Trp Pro Val Tyr Trp Phe Phe Gln Gly Ser Tyr Leu Thr
            100                 105                 110 ggc gtc tgg gtc atc gcg cac gag tgt ggc cac cag gcc tac tgc tcg   384
Gly Val Trp Val Ile Ala His Glu Cys Gly His Gln Ala Tyr Cys Ser
        115                 120                 125 agc gag gtc gtc aac aac ctc atc ggc ctc gta ctg cac tcg gcg ctg   432
Ser Glu Val Val Asn Asn Leu Ile Gly Leu Val Leu His Ser Ala Leu
    130                 135                 140
```

```
ctt gtg ccg tac cac agc tgg cgc atc tcg cac cgc aag cac cac tcc    480
Leu Val Pro Tyr His Ser Trp Arg Ile Ser His Arg Lys His His Ser
145                 150                 155                 160 aac acg ggc agc tgc gag aac gac gag gtg ttc gtg ccc gtc acc cgc    528
Asn Thr Gly Ser Cys Glu Asn Asp Glu Val Phe Val Pro Val Thr Arg
                165                 170                 175 tcg gtg ctc gcc agc tcc tgg aac gag acg ctc gag gac tcg ccg ctc    576
Ser Val Leu Ala Ser Ser Trp Asn Glu Thr Leu Glu Asp Ser Pro Leu
            180                 185                 190 tac cag ctc tac cgc atc gtg tac atg ctg gtc gtg ggc tgg atg ccc    624
Tyr Gln Leu Tyr Arg Ile Val Tyr Met Leu Val Val Gly Trp Met Pro
        195                 200                 205 ggc tac ctc ttc ttc aac gcc acg ggc ccg acc aag tac tgg ggc aag    672
Gly Tyr Leu Phe Phe Asn Ala Thr Gly Pro Thr Lys Tyr Trp Gly Lys
    210                 215                 220 tcg cgc agc cac ttc aac ccg tac tcg gcc atc tac gcc gac cgc gag    720
Ser Arg Ser His Phe Asn Pro Tyr Ser Ala Ile Tyr Ala Asp Arg Glu
225                 230                 235                 240 cgc tgg atg atc gtg ctg agc gac atc ttc ctc gtg gcc atg ctg gcc    768
Arg Trp Met Ile Val Leu Ser Asp Ile Phe Leu Val Ala Met Leu Ala
                245                 250                 255 gtg ctg gcc gcg ctc gtg cac acc ttc tcc ttc aac acc atg gtc aag    816
Val Leu Ala Ala Leu Val His Thr Phe Ser Phe Asn Thr Met Val Lys
                260                 265                 270 ttc tac gtc gtg ccc tac ttc atc gtc aac gcc tac ctc gtg ctt atc    864
Phe Tyr Val Val Pro Tyr Phe Ile Val Asn Ala Tyr Leu Val Leu Ile
            275                 280                 285 acg tac ctg cag cac acg gac acg tac atc ccg cac ttc cgc gag ggc    912
Thr Tyr Leu Gln His Thr Asp Thr Tyr Ile Pro His Phe Arg Glu Gly
        290                 295                 300 gag tgg aac tgg ctg cgc ggc gcg ctt tgc acg gtg gac cgg tcg ttc    960
Glu Trp Asn Trp Leu Arg Gly Ala Leu Cys Thr Val Asp Arg Ser Phe
305                 310                 315                 320 ggc ccg ttc ctc gac tcg gtg gtg cac cgc atc gtg gac acg cac gtg    1008
Gly Pro Phe Leu Asp Ser Val Val His Arg Ile Val Asp Thr His Val
                325                 330                 335 tgc cac cac atc ttc tcc aag atg ccg ttc tac cac tgc gag gag gcc    1056
Cys His His Ile Phe Ser Lys Met Pro Phe Tyr His Cys Glu Glu Ala
                340                 345                 350 acg aac gcc atc aag ccg ctg ctg ggc aag ttc tac ctc aag gac acg    1104
Thr Asn Ala Ile Lys Pro Leu Leu Gly Lys Phe Tyr Leu Lys Asp Thr
            355                 360                 365 acg ccc gtg ccc gtc gcg ctc tgg cgg tcc tac acg cac tgc aag ttc    1152
Thr Pro Val Pro Val Ala Leu Trp Arg Ser Tyr Thr His Cys Lys Phe
        370                 375                 380 gtc gag gac gac ggc aag gtc gtc ttc tac aag aac aag ctc taa        1197
Val Glu Asp Asp Gly Lys Val Val Phe Tyr Lys Asn Lys Leu
385                 390                 395

<210> SEQ ID NO 26
<211> LENGTH: 398
<212> TYPE: PRT
<213> ORGANISM: Phytophthora sojae

<400> SEQUENCE: 26

Met Ala Ile Leu Asn Pro Glu Ala Asp Ser Ala Asn Leu Ala Thr
1               5                   10                  15

Asp Ser Glu Ala Lys Gln Arg Gln Leu Ala Glu Ala Gly Tyr Thr His
                20                  25                  30

Val Glu Gly Ala Pro Ala Pro Leu Pro Leu Glu Leu Pro His Phe Ser
```

```
                35                  40                  45
Leu Arg Asp Leu Arg Ala Ala Ile Pro Lys His Cys Phe Glu Arg Ser
 50                  55                  60

Phe Val Thr Ser Thr Tyr Tyr Met Ile Lys Asn Val Leu Thr Cys Ala
 65                  70                  75                  80

Ala Leu Phe Tyr Ala Ala Thr Phe Ile Asp Arg Ala Gly Ala Ala Ala
                 85                  90                  95

Tyr Val Leu Trp Pro Val Tyr Trp Phe Gln Gly Ser Tyr Leu Thr
                100                 105                 110

Gly Val Trp Val Ile Ala His Glu Cys Gly His Gln Ala Tyr Cys Ser
                115                 120                 125

Ser Glu Val Val Asn Asn Leu Ile Gly Leu Val Leu His Ser Ala Leu
130                 135                 140

Leu Val Pro Tyr His Ser Trp Arg Ile Ser His Arg Lys His His Ser
145                 150                 155                 160

Asn Thr Gly Ser Cys Glu Asn Asp Glu Val Phe Val Pro Val Thr Arg
                165                 170                 175

Ser Val Leu Ala Ser Ser Trp Asn Glu Thr Leu Glu Asp Ser Pro Leu
                180                 185                 190

Tyr Gln Leu Tyr Arg Ile Val Tyr Met Leu Val Val Gly Trp Met Pro
                195                 200                 205

Gly Tyr Leu Phe Phe Asn Ala Thr Gly Pro Thr Lys Tyr Trp Gly Lys
                210                 215                 220

Ser Arg Ser His Phe Asn Pro Tyr Ser Ala Ile Tyr Ala Asp Arg Glu
225                 230                 235                 240

Arg Trp Met Ile Val Leu Ser Asp Ile Phe Leu Val Ala Met Leu Ala
                245                 250                 255

Val Leu Ala Ala Leu Val His Thr Phe Ser Phe Asn Thr Met Val Lys
                260                 265                 270

Phe Tyr Val Val Pro Tyr Phe Ile Val Asn Ala Tyr Leu Val Leu Ile
                275                 280                 285

Thr Tyr Leu Gln His Thr Asp Thr Tyr Ile Pro His Phe Arg Glu Gly
                290                 295                 300

Glu Trp Asn Trp Leu Arg Gly Ala Leu Cys Thr Val Asp Arg Ser Phe
305                 310                 315                 320

Gly Pro Phe Leu Asp Ser Val Val His Arg Ile Val Asp Thr His Val
                325                 330                 335

Cys His His Ile Phe Ser Lys Met Pro Phe Tyr His Cys Glu Glu Ala
                340                 345                 350

Thr Asn Ala Ile Lys Pro Leu Leu Gly Lys Phe Tyr Leu Lys Asp Thr
                355                 360                 365

Thr Pro Val Pro Val Ala Leu Trp Arg Ser Tyr Thr His Cys Lys Phe
                370                 375                 380

Val Glu Asp Asp Gly Lys Val Val Phe Tyr Lys Asn Lys Leu
385                 390                 395

<210> SEQ ID NO 27
<211> LENGTH: 24
<212> TYPE: DNA
<213> ORGANISM: unknown
<220> FEATURE:
<223> OTHER INFORMATION: artificial sequence
<220> FEATURE:
<221> NAME/KEY: misc_feature
<222> LOCATION: (1)..(24)
<223> OTHER INFORMATION: primer
```

```
<400> SEQUENCE: 27
gccatggccc ccatcgagac cgac                                          24

<210> SEQ ID NO 28
<211> LENGTH: 20
<212> TYPE: DNA
<213> ORGANISM: unknown
<220> FEATURE:
<223> OTHER INFORMATION: artificial sequence

<400> SEQUENCE: 28
ttagcccatg tggacggaca                                               20

<210> SEQ ID NO 29
<211> LENGTH: 25
<212> TYPE: DNA
<213> ORGANISM: unknown
<220> FEATURE:
<223> OTHER INFORMATION: artificial sequence
<220> FEATURE:
<221> NAME/KEY: misc_feature
<222> LOCATION: (1)..(25)
<223> OTHER INFORMATION: primer

<400> SEQUENCE: 29
accatggtgg atggccccaa gacca                                         25

<210> SEQ ID NO 30
<211> LENGTH: 25
<212> TYPE: DNA
<213> ORGANISM: unknown
<220> FEATURE:
<223> OTHER INFORMATION: artificial sequence
<220> FEATURE:
<221> NAME/KEY: misc_feature
<222> LOCATION: (1)..(25)
<223> OTHER INFORMATION: primer

<400> SEQUENCE: 30
ttacatggcc gggaactcga gcagg                                         25

<210> SEQ ID NO 31
<211> LENGTH: 22
<212> TYPE: DNA
<213> ORGANISM: unknown
<220> FEATURE:
<223> OTHER INFORMATION: artificial sequence
<220> FEATURE:
<221> NAME/KEY: misc_feature
<222> LOCATION: (1)..(22)
<223> OTHER INFORMATION: primer

<400> SEQUENCE: 31
gccatggcga tcctgaaccc gg                                            22

<210> SEQ ID NO 32
<211> LENGTH: 19
<212> TYPE: DNA
<213> ORGANISM: unknown
<220> FEATURE:
<223> OTHER INFORMATION: artificial sequence
<220> FEATURE:
<221> NAME/KEY: misc_feature
<222> LOCATION: (1)..(19)
<223> OTHER INFORMATION: primer

<400> SEQUENCE: 32
tagagcttgt tcttgtaga                                                19
```

```
<210> SEQ ID NO 33
<211> LENGTH: 23
<212> TYPE: DNA
<213> ORGANISM: unknown
<220> FEATURE:
<223> OTHER INFORMATION: artificial sequence
<220> FEATURE:
<221> NAME/KEY: misc_feature
<222> LOCATION: (1)..(23)
<223> OTHER INFORMATION: primer

<400> SEQUENCE: 33
gccatggcgt ccaagcagga gca                                              23

<210> SEQ ID NO 34
<211> LENGTH: 25
<212> TYPE: DNA
<213> ORGANISM: unknown
<220> FEATURE:
<223> OTHER INFORMATION: artificial sequence
<220> FEATURE:
<221> NAME/KEY: misc_feature
<222> LOCATION: (1)..(25)
<223> OTHER INFORMATION: primer

<400> SEQUENCE: 34
tcagttggcc ttagtcttgg tcgcc                                            25

<210> SEQ ID NO 35
<211> LENGTH: 24
<212> TYPE: DNA
<213> ORGANISM: unknown
<220> FEATURE:
<223> OTHER INFORMATION: artificial sequence
<220> FEATURE:
<221> NAME/KEY: misc_feature
<222> LOCATION: (1)..(24)
<223> OTHER INFORMATION: primer

<400> SEQUENCE: 35
aagatggaga cgaccttcgc gcgc                                             24

<210> SEQ ID NO 36
<211> LENGTH: 28
<212> TYPE: DNA
<213> ORGANISM: unknown
<220> FEATURE:
<223> OTHER INFORMATION: artificial sequence
<220> FEATURE:
<221> NAME/KEY: misc_feature
<222> LOCATION: (1)..(28)
<223> OTHER INFORMATION: primer

<400> SEQUENCE: 36
ttactgcgtc ttcttggcga ccgcagcg                                         28

<210> SEQ ID NO 37
<211> LENGTH: 23
<212> TYPE: DNA
<213> ORGANISM: unknown
<220> FEATURE:
<223> OTHER INFORMATION: artificial sequence
<220> FEATURE:
<221> NAME/KEY: misc_feature
<222> LOCATION: (1)..(23)
<223> OTHER INFORMATION: primer

<400> SEQUENCE: 37
gccatggcgt cggagctgct gca                                              23
```

```
<210> SEQ ID NO 38
<211> LENGTH: 21
<212> TYPE: DNA
<213> ORGANISM: unknown
<220> FEATURE:
<223> OTHER INFORMATION: artificial sequence
<220> FEATURE:
<221> NAME/KEY: misc_feature
<222> LOCATION: (1)..(21)
<223> OTHER INFORMATION: primer

<400> SEQUENCE: 38
ttagaggttc ttcttggccg g                                              21

<210> SEQ ID NO 39
<211> LENGTH: 22
<212> TYPE: DNA
<213> ORGANISM: unknown
<220> FEATURE:
<223> OTHER INFORMATION: artificial sequence
<220> FEATURE:
<221> NAME/KEY: misc_feature
<222> LOCATION: (1)..(22)
<223> OTHER INFORMATION: primer

<400> SEQUENCE: 39
accatgtcgg ccgacctgct gc                                             22

<210> SEQ ID NO 40
<211> LENGTH: 18
<212> TYPE: DNA
<213> ORGANISM: unknown
<220> FEATURE:
<223> OTHER INFORMATION: artificial sequence
<220> FEATURE:
<221> NAME/KEY: misc_feature
<222> LOCATION: (1)..(18)
<223> OTHER INFORMATION: primer

<400> SEQUENCE: 40
ttagagcttc ttcttggc                                                  18

<210> SEQ ID NO 41
<211> LENGTH: 32
<212> TYPE: DNA
<213> ORGANISM: unknown
<220> FEATURE:
<223> OTHER INFORMATION: artificial sequence
<220> FEATURE:
<221> NAME/KEY: misc_feature
<222> LOCATION: (1)..(32)
<223> OTHER INFORMATION: primer

<400> SEQUENCE: 41
gcggccgcgc catggccccc atcgagaccg ac                                  32

<210> SEQ ID NO 42
<211> LENGTH: 28
<212> TYPE: DNA
<213> ORGANISM: unknown
<220> FEATURE:
<223> OTHER INFORMATION: artificial sequence
<220> FEATURE:
<221> NAME/KEY: misc_feature
<222> LOCATION: (1)..(28)
<223> OTHER INFORMATION: primer

<400> SEQUENCE: 42
gcggccgctt agcccatgtg gacggaca                                       28
```

```
<210> SEQ ID NO 43
<211> LENGTH: 33
<212> TYPE: DNA
<213> ORGANISM: unknown
<220> FEATURE:
<223> OTHER INFORMATION: artificial sequence
<220> FEATURE:
<221> NAME/KEY: misc_feature
<222> LOCATION: (1)..(33)
<223> OTHER INFORMATION: primer

<400> SEQUENCE: 43
gcggccgcac catggtggat ggccccaaga cca                          33

<210> SEQ ID NO 44
<211> LENGTH: 33
<212> TYPE: DNA
<213> ORGANISM: unknown
<220> FEATURE:
<223> OTHER INFORMATION: artificial sequence
<220> FEATURE:
<221> NAME/KEY: misc_feature
<222> LOCATION: (1)..(33)
<223> OTHER INFORMATION: primer

<400> SEQUENCE: 44
gcggccgctt acatggccgg gaactcgagc agg                          33

<210> SEQ ID NO 45
<211> LENGTH: 30
<212> TYPE: DNA
<213> ORGANISM: unknown
<220> FEATURE:
<223> OTHER INFORMATION: artificial sequence
<220> FEATURE:
<221> NAME/KEY: misc_feature
<222> LOCATION: (1)..(30)
<223> OTHER INFORMATION: primer

<400> SEQUENCE: 45
gcggccgcgc catggcgatc ctgaacccgg                              30

<210> SEQ ID NO 46
<211> LENGTH: 27
<212> TYPE: DNA
<213> ORGANISM: unknown
<220> FEATURE:
<223> OTHER INFORMATION: artificial sequence
<220> FEATURE:
<221> NAME/KEY: misc_feature
<222> LOCATION: (1)..(27)
<223> OTHER INFORMATION: primer

<400> SEQUENCE: 46
gcggccgcta gagcttgttc ttgtaga                                 27

<210> SEQ ID NO 47
<211> LENGTH: 31
<212> TYPE: DNA
<213> ORGANISM: unknown
<220> FEATURE:
<223> OTHER INFORMATION: artificial sequence
<220> FEATURE:
<221> NAME/KEY: misc_feature
<222> LOCATION: (1)..(31)
<223> OTHER INFORMATION: primer

<400> SEQUENCE: 47
gcggccgcgc catggcgtcc aagcaggagc a                            31
```

```
<210> SEQ ID NO 48
<211> LENGTH: 33
<212> TYPE: DNA
<213> ORGANISM: unknown
<220> FEATURE:
<223> OTHER INFORMATION: artificial sequence
<220> FEATURE:
<221> NAME/KEY: misc_feature
<222> LOCATION: (1)..(33)
<223> OTHER INFORMATION: primer

<400> SEQUENCE: 48
gcggccgctc agttggcctt agtcttggtc gcc                              33

<210> SEQ ID NO 49
<211> LENGTH: 32
<212> TYPE: DNA
<213> ORGANISM: unknown
<220> FEATURE:
<223> OTHER INFORMATION: artificial sequence
<220> FEATURE:
<221> NAME/KEY: misc_feature
<222> LOCATION: (1)..(32)
<223> OTHER INFORMATION: primer

<400> SEQUENCE: 49
gcggccgcaa gatggagacg accttcgcgc gc                               32

<210> SEQ ID NO 50
<211> LENGTH: 36
<212> TYPE: DNA
<213> ORGANISM: unknown
<220> FEATURE:
<223> OTHER INFORMATION: artificial sequence
<220> FEATURE:
<221> NAME/KEY: misc_feature
<222> LOCATION: (1)..(36)
<223> OTHER INFORMATION: primer

<400> SEQUENCE: 50
gcggccgctt actgcgtctt cttggcgacc gcagcg                           36

<210> SEQ ID NO 51
<211> LENGTH: 31
<212> TYPE: DNA
<213> ORGANISM: unknown
<220> FEATURE:
<223> OTHER INFORMATION: artificial sequence
<220> FEATURE:
<221> NAME/KEY: misc_feature
<222> LOCATION: (1)..(31)
<223> OTHER INFORMATION: primer

<400> SEQUENCE: 51
gcggccgcgc catggcgtcg gagctgctgc a                                31

<210> SEQ ID NO 52
<211> LENGTH: 29
<212> TYPE: DNA
<213> ORGANISM: unknown
<220> FEATURE:
<223> OTHER INFORMATION: artificial sequence
<220> FEATURE:
<221> NAME/KEY: misc_feature
<222> LOCATION: (1)..(29)
<223> OTHER INFORMATION: primer

<400> SEQUENCE: 52
gcggccgctt agaggttctt cttggccgg                                   29
```

```
<210> SEQ ID NO 53
<211> LENGTH: 30
<212> TYPE: DNA
<213> ORGANISM: unknown
<220> FEATURE:
<223> OTHER INFORMATION: artificial sequence
<220> FEATURE:
<221> NAME/KEY: misc_feature
<222> LOCATION: (1)..(30)
<223> OTHER INFORMATION: primer

<400> SEQUENCE: 53
gcggccgcac catgtcggcc gacctgctgc                                    30

<210> SEQ ID NO 54
<211> LENGTH: 26
<212> TYPE: DNA
<213> ORGANISM: unknown
<220> FEATURE:
<223> OTHER INFORMATION: artificial sequence
<220> FEATURE:
<221> NAME/KEY: misc_feature
<222> LOCATION: (1)..(26)
<223> OTHER INFORMATION: primer

<400> SEQUENCE: 54
gcggccgctt agagcttctt cttggc                                        26

<210> SEQ ID NO 55
<211> LENGTH: 60
<212> TYPE: DNA
<213> ORGANISM: unknown
<220> FEATURE:
<223> OTHER INFORMATION: artificial sequence
<220> FEATURE:
<221> NAME/KEY: misc_feature
<222> LOCATION: (1)..(60)
<223> OTHER INFORMATION: primer

<400> SEQUENCE: 55
gtcgacccgc ggactagtgg gccctctaga cccgggggat ccggatctgc tggctatgaa   60
```